(12) United States Patent
Cheng et al.

(10) Patent No.: US 11,020,409 B2
(45) Date of Patent: Jun. 1, 2021

(54) BROAD ANTIVIRAL THERAPY WITH MEMBRANE MODIFYING OXYSTEROLS

(71) Applicant: The Regents of the University of California, Oakland, CA (US)

(72) Inventors: Genhong Cheng, Los Angeles, CA (US); Su-Yang Liu, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/988,988

(22) Filed: May 24, 2018

(65) Prior Publication Data

US 2019/0015426 A1 Jan. 17, 2019

Related U.S. Application Data

(63) Continuation of application No. 14/398,865, filed as application No. PCT/US2013/039748 on May 6, 2013, now abandoned.

(60) Provisional application No. 61/643,110, filed on May 4, 2012.

(51) Int. Cl.
*A61K 31/575* (2006.01)
*A61K 47/40* (2006.01)

(52) U.S. Cl.
CPC ............ *A61K 31/575* (2013.01); *A61K 47/40* (2013.01)

(58) Field of Classification Search
CPC ............................... A61K 31/575; A61K 47/40
See application file for complete search history.

(56) References Cited

U.S. PATENT DOCUMENTS

| 5,041,543 A * | 8/1991 | Shaver | C07H 19/06 536/28.2 |
| 2002/0010128 A1* | 1/2002 | Parks | A61K 9/0014 424/70.1 |

OTHER PUBLICATIONS

Abdool Karin et al. in Science 329(5996): 1168-1174 (2010) (Year: 2010).*
Moog et al. in Antiviral Chemistry & Chemotherapy 9(6), 491-496 (1998) (Year: 1998).*
Delang et al. in Hepatology: 50:6-16 (2009) (Year: 2009).*
Pezacki et al. in BMC Chemical Biology 9:2, 1-15 (2009) (Year: 2009).*
Andrew J, and Jessup, W. (1999). Oxysterols and atherosclerosis. Atherosclerosis 142, 1-28.
Bauman, D. R., Bitmansour, A D., McDonald, J. G., Thompson, B. M., Liang, G., and Russell, D. W. (2009). 25-Hydroxycholesterol secreted by macrophages in response to Toll-like receptor activation suppresses immunoglobulin A production. Proceedings of the National Academy of Sciences 106, 16764-16769.
Brass, A. L., Huang, I.-C., Benita, Y., John, S. P., Krishnan, M. N., Feeley, E. M., Ryan, B. J., Weyer, J. L., van der Weyden, L., Fikrig, E., et al. (2009). The IFITM Proteins Mediate Cellular Resistance to Influenza A H1N1 Virus, West Nile Virus, and Dengue Virus. Cell 139, 1243-1254.
Butler, S. L., Hansen, M. S. T., and Bushman, F. D. (2001). A quantitative assay for HIV DNA integration in vivo. Nat Med 7, 631-634.
Cavrois, M., de Noronha, C., and Greene, W. C. (2002). A sensitive and specific enzyme-based assay detecting HIV-1 virion fusion in primary T lymphocytes. Nat Biotech 20, 1151-1154.
Degols, G., Eldin, P., and Mechti, N. (Jun.). ISG20, an actor of the innate immune response. Biochimie 89, 831-835.
Gale, S. E., Westover, E. J., Dudley, N., Krishnan, K., Merlin, S., Scherrer, D. E., Han, X., Zhai, X., Brockman, H. L., Brown, R. E., et al. (2009). Side Chain Oxygenated Cholesterol Regulates Cellular Cholesterol Homeostasis through Direct Sterol-Membrane Interactions. Journal of Biological Chemistry 284, 1755-1764.
Garcia, M. A., Gil, J., Ventoso, I., Guerra, S., Domingo, E., Rivas, C., and Esteban, M. (2006). Impact of Protein Kinase PKR in Cell Biology: from Antiviral to Antiproliferative Action. Microbiology and Molecular Biology Reviews 70, 1032-1060.
Holmes, R., VandeBerg, J., and Cox, L. (2011). Genomics and proteomics of vertebrate cholesterol ester lipase (LIPA) and cholesterol 25-hydroxylase (CH25H). 3 Biotech 1, 99-109.
Janowski, B. A., Grogan, M. J., Jones, S. A., Wisely, G. B., Kliewer, S. A., Corey, E. J., and Mangelsdorf, D. J. (1999). Structural requirements of ligands for the oxysterol liver X receptors LXRα and LXRβ. Proceedings of the National Academy of Sciences 96, 266-271.
Kandutsch, A., Chen, H., and Heiniger, H. (1978). Biological activity of some oxygenated sterols. Science 201, 498-501.
Kielian, M. and Rey, F. A. (2006). Virus membrane-fusion proteins: more than one way to make a hairpin. Nat Rev Micro 4, 67-76.
Korin, Y. D., and Zack, J. A. (1999). Nonproductive Human Immunodeficiency Virus Type 1 Infection in Nucleoside-Treated GO Lymphocytes. Journal of Virology 73, 6526-6532.
Lange, Y., Ye, J., and Steck, T. L. (2004). How cholesterol homeostasis is regulated by plasma membrane cholesterol in excess of phospholipids. Proceedings of the National Academy of Sciences of the United States of America 101, 11664-11667.
Liu, S.-Y., Sanchez, D. J., Aliyari, R., Lu, S., and Cheng, G. (2012). Systematic identification of type I and type II interferon-induced antiviral factors. Proceedings of the National Academy of Sciences 109, 4239-4244.

(Continued)

*Primary Examiner* — Dennis Heyer
(74) *Attorney, Agent, or Firm* — Venable LLP; Keith G. Haddaway; Miguel A. Lopez

(57) ABSTRACT

This invention relates, e.g., to a method for inhibiting the growth and/or proliferation and/or infectivity of a virus in a cell, such as a mammalian cell (e.g. for inhibiting entry of the virus into the cell), comprising administering, or causing to be administered, to the cell, 25-hydroxycholesterol (25HC) in an amount sufficient to inhibit the growth and/or proliferation and/or infectivity of the vines in the cell. The method can be carried out in vivo or in vitro. Among the viruses that can be inhibited are, e.g., VSV, HSV, MHV68, HCV, HIV, EBOV, RVFV, RSSEV and Nipah virus. In one embodiment of the invention, the 25HC is administered topically, e.g. to a mucosal surface.

14 Claims, 30 Drawing Sheets

Specification includes a Sequence Listing.

(56) References Cited

OTHER PUBLICATIONS

Moog, C., Aubertin, A., Kim, A., and Luu, B. (1998). Oxysterols, but not cholesterol, inhibit human immunodeficiency virus replication in vitro. Antiviral Chemistry & Chemotherapy 9, 491-496.

Mortazavi, A., Williams, B. A., McCue, K., Schaeffer, L., and Wold, B. (2008). Mapping and quantifying mammalian transcriptomes by RNA-Seq. Nat Meth 5, 621-628.

Negrete, O. A., Wolf, M. C., Aguilar, H. C., Enterlein, S., Wang, W., Mithlberger, E., Su, S. V., Bertolotti-Ciarlet, A., Flick, R., and Lee, B. (2006). Two Key Residues in EphrinB3 Are Critical for Its Use as an Alternative Receptor for Nipah Virus. PLoS Pathog 2, e7.

Olsen, B. N., Schlesinger, P. H., Ory, D. S., and Baker, N. A. (2011). 25-Hydroxycholesterol Increases the Availability of Cholesterol in Phospholipid Membranes. Biophysical Journal 100, 948-956.

Palleroni, A. V., Varesio, L., Wright, R. B., and Brunda, M. J. (1991). Tumoricidal alveolar macrophage and tumor infiltrating macrophage cell lines. Int. J. Cancer 49, 296-302.

Park, K., and Scott, A. L. (2010). Cholesterol 25-hydroxylase production by dendritic cells and macrophages is regulated by type I interferons. Journal of Leukocyte Biology 88, 1081-1087.

Pècheur, E.-I., Sainte-Marie, J., Bienvenüe, A., and Hoekstra, D. (1998). Lipid Headgroup Spacing and Peptide Penetration, but Not Peptide Oligomerization, Modulate Peptide-Induced Fusion †. Biochemistry 38, 364-373.

Perez-Caballero, D., Zang, T., Ebrahimi, A., McNatt, M. W., Gregory, D. A., Johnson, M. C., and Bieniasz, P. D. (2009). Tetherin Inhibits HIV-1 Release by Directly Tethering Virions to Cells. Cell 139, 499-511.

Pezacki, J., Sagan, S., Tonary, A., Rouleau, Y., Belanger, S., Supekova, L., and Su, A. (2009). Transcriptional profiling of the effects of 25-hydroxycholesterol on human hepatocyte metabolism and the antiviral state it conveys against the hepatitis C virus. BMC Chemical Biology 9, 2.

Radhakrishnan, A., Ikeda, Y., Kwon, H. J., Brown, M. S., and Goldstein, J. L. (2007). Sterol-regulated transport of SREBPs from endoplasmic reticulum to Golgi: Oxysterols block transport by binding to Insig. Proceedings of the National Academy of Sciences 104, 6511-6518.

Scherle, P. A., Dorshkind, K., and Witte, O. N. (1990). Clonal lymphoid progenitor cell lines expressing the BCR/ABL oncogene retain full differentiative function. Proceedings of the National Academy of Sciences 87, 1908-1912.

Takada, A., Robison, C., Goto, H., Sanchez, A., Murti, K. G., Whitt, M. A., and Kawaoka, Y. (1997). A system for functional analysis of Ebola virus glycoprotein. Proceedings of the National Academy of Sciences 94, 14764-14769.

Teissier, É., and Pécheur, E.-I. (2007). Lipids as modulators of membrane fusion mediated by viral fusion proteins. European Biophysics Journal 36, 887-899.

Vaney, M.-C., and Rey, F. A. (2011). Class II enveloped viruses. Cellular Microbiology 13, 1451-1459.

Wang, F., Xia, W., Liu, F., Li, J., Wang, G., and Gu, J. (2012). Interferon regulator factor 1/retinoic inducible gene I (IRF1/RIG-I) axis mediates 25-hydroxycholesterol-induced interleukin-8 production in atherosclerosis. Cardiovascular Research 93, 190-199.

Wang, L., Feng, Z., Wang, X., Wang, X., and Zhang, X. (2010). DEGseq: an R package for identifying differentially expressed genes from RNA-seq data. Bioinformatics 26, 136-138.

Weidner, J. M., Jiang, D., Pan, X.-B., Chang, J., Block, T. M., and Guo, J.-T. (2010). Interferon-Induced Cell Membrane Proteins, IFITM3 and Tetherin, Inhibit Vesicular Stomatitis Virus Infection via Distinct Mechanisms. Journal of Virology 84, 12646-12657.

Wolf, M., Wang, Y., Freiberg, A., Aguilar, H., Holbrook, M., and Lee, B. (2009). A catalytically and genetically optimized beta-lactamase-matrix based assay for sensitive, specific, and higher throughput analysis of native henipavirus entry characteristics. Virology Journal 6, 119.

Zhang, L., Jiang, Q., Li, G., Jeffrey, J., Kovalev, G. I., and Su, L. (2011). Efficient infection and impairment of pDC in the bone marrow and peripheral lymphoid organs during early HIV-1 infection in humanized rag2-/-γC-/- mice in vivo. Blood.

Zhang, L., Kovalev, G. I., and Su, L. (2006). HIV-1 infection and pathogenesis in a novel humanized mouse model. Blood.

Zlokarnik, G., Negulescu, P. A., Knapp, T. E., Mere, L., Burres, N., Feng, L., Whitney, M.,Roemer, K., and Tsien, R. Y. (1998). Quantitation of Transcription and Clonal Selection of Single Living Cells with β-Lactamase as Reporter. Science 279, 84-88.

Zou, T., Garifulin, O., Berland, R., and Boyartchuk, V. L. (2011). Listeria monocytogenes Infection Induces Prosurvival Metabolic Signaling in Macrophages. Infection and Immunity 79, 1526-1535.

Liu, X. V., Ho, S. S. W., Tan, J. J., Kamran, N., and Gasser, S. (2012). Ras Activation Induces Expression of Raet1 Family NK Receptor Ligands. The Journal of Immunology 189, 1826-1834.

Miller, B. T., Ueta, C. B., Lau, V., Jacomino, K. G., Wasserman, L. M., and Kim, B. W. (2012). Statins and Downstream Inhibitors of the Isoprenylation Pathway Increase Type 2 Iodothyronine Deiodinase Activity. Endocrinology 153, 4039-4048.

Wilson, A. L., Erdman, R. A., Castellano, F., and Maltese, W. A. (1998). Prenylation of Rab8 GTPase by type I and type II geranylgeranyl transferases. Biochem. J. 333, 497-504.

Wolf, M. C., Freiberg, A. N., Zhang, T., Akyol-Ataman, Z., Grock, A., Hong, P. W., Li, J., Watson, N. F., Fang, A. Q., Aguilar, H. C., et al. (2010). A broad-spectrum antiviral targeting entry of enveloped viruses. Proceedings of the National Academy of Sciences 107, 3157-3162.

\* cited by examiner

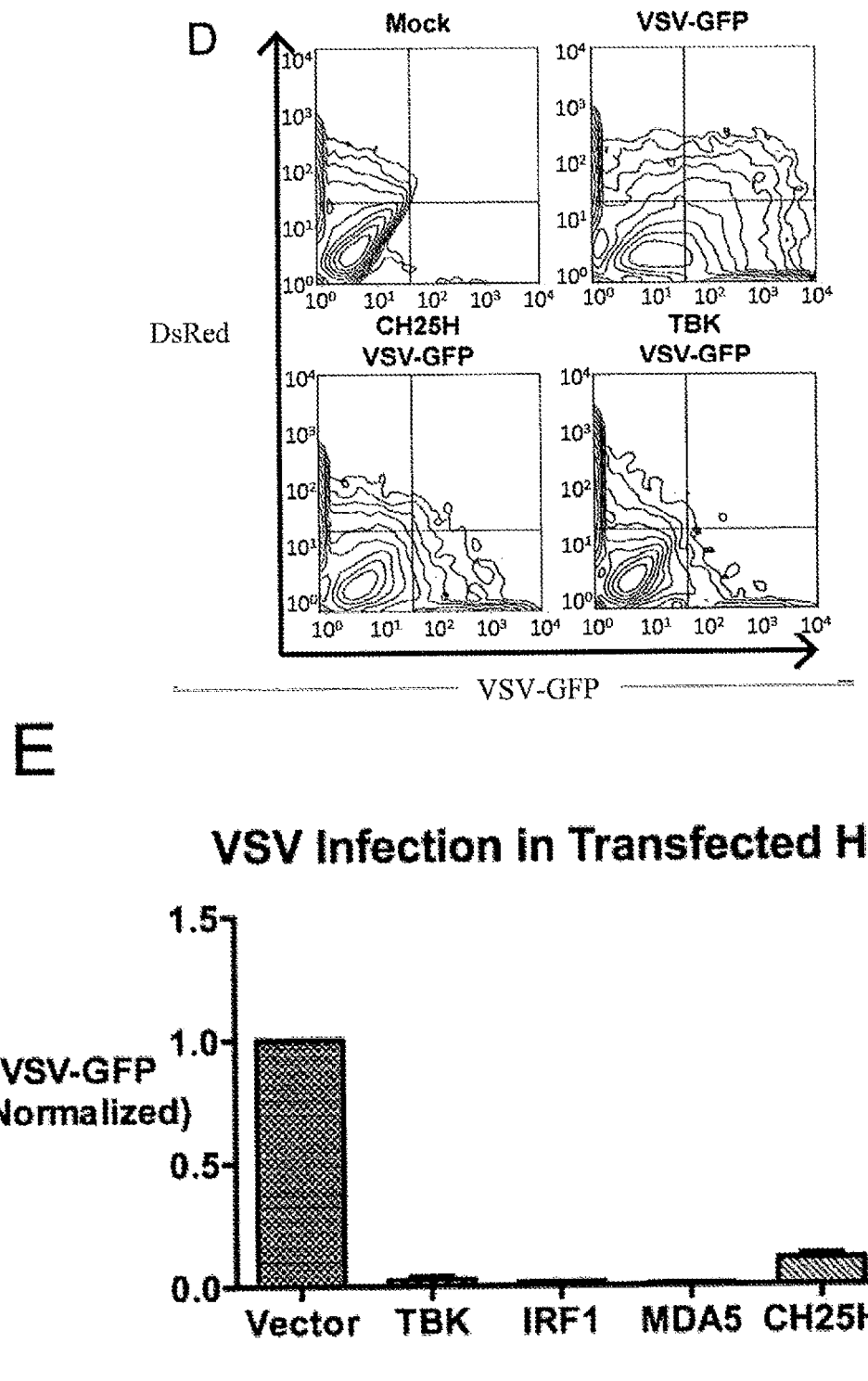
Fig. 1, cont'd

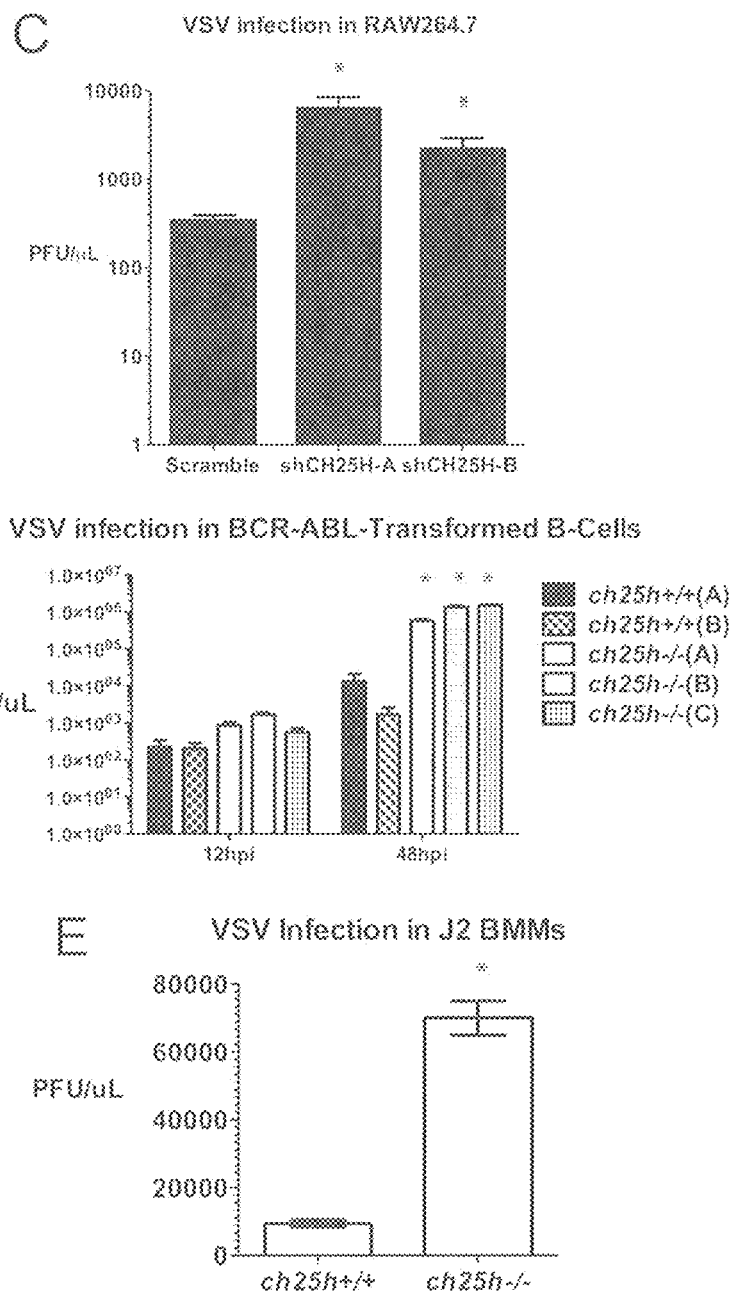
Fig. 2, cont'd.

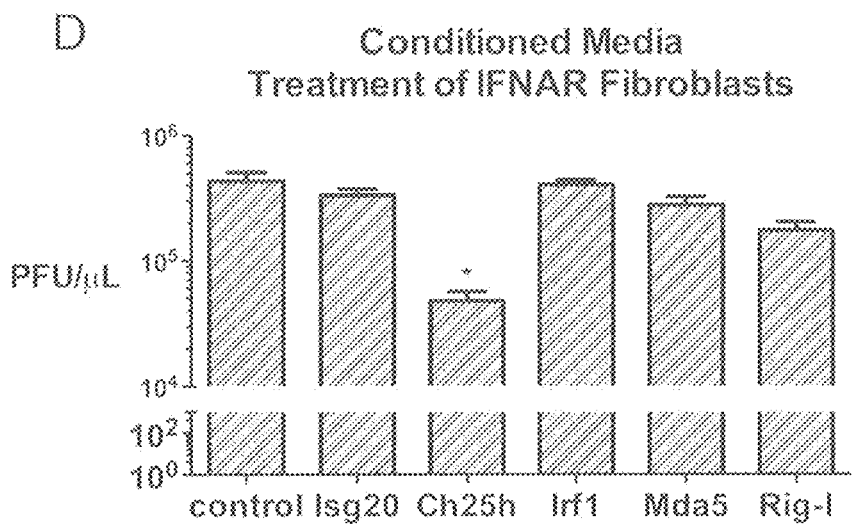
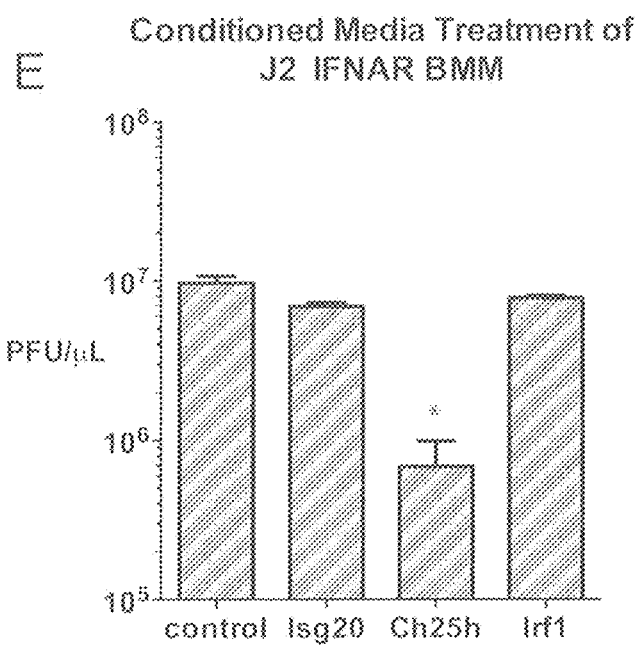
*Fig. 3, cont'd.*

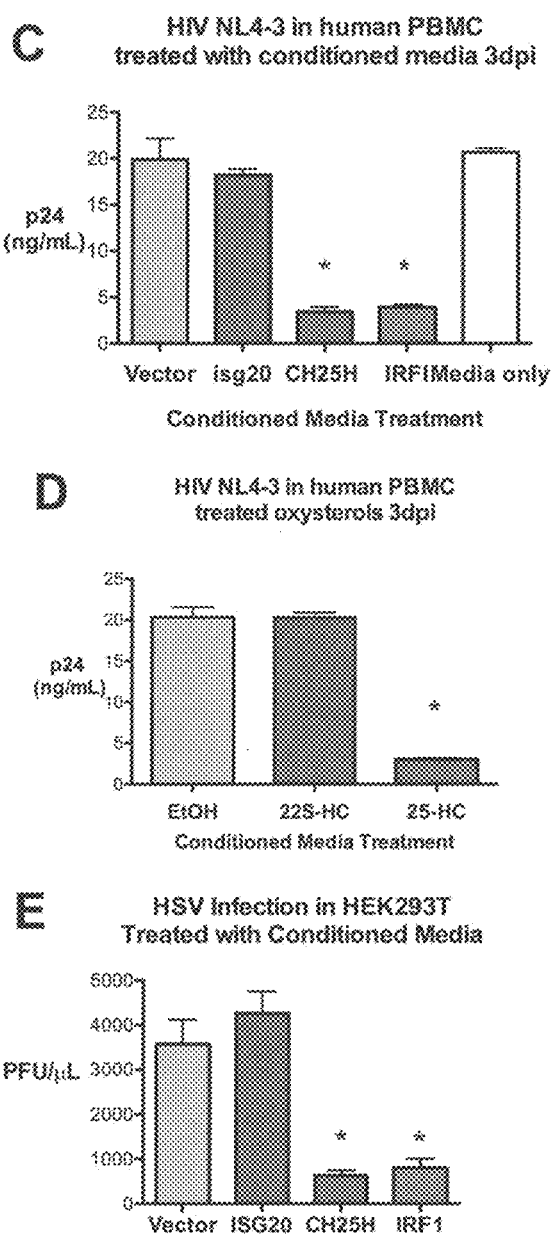
Fig. 4, cont'd.

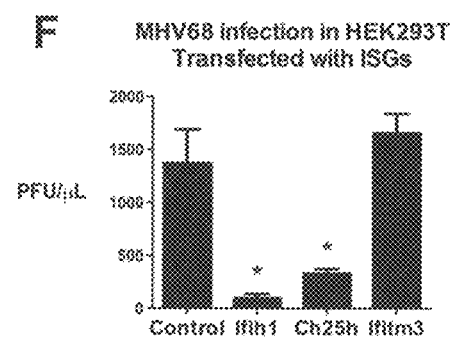
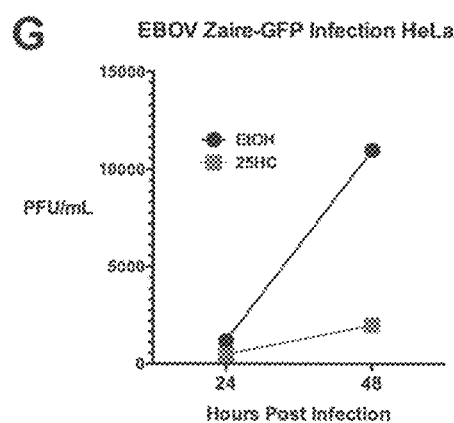
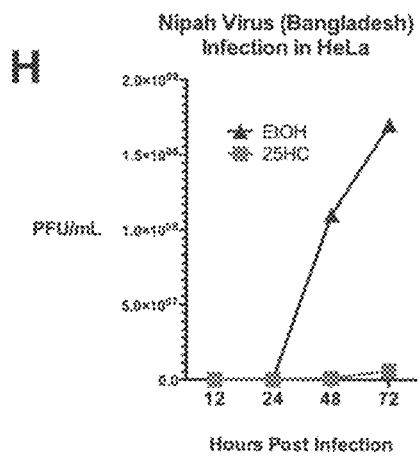
*Fig. 4, cont'd.*

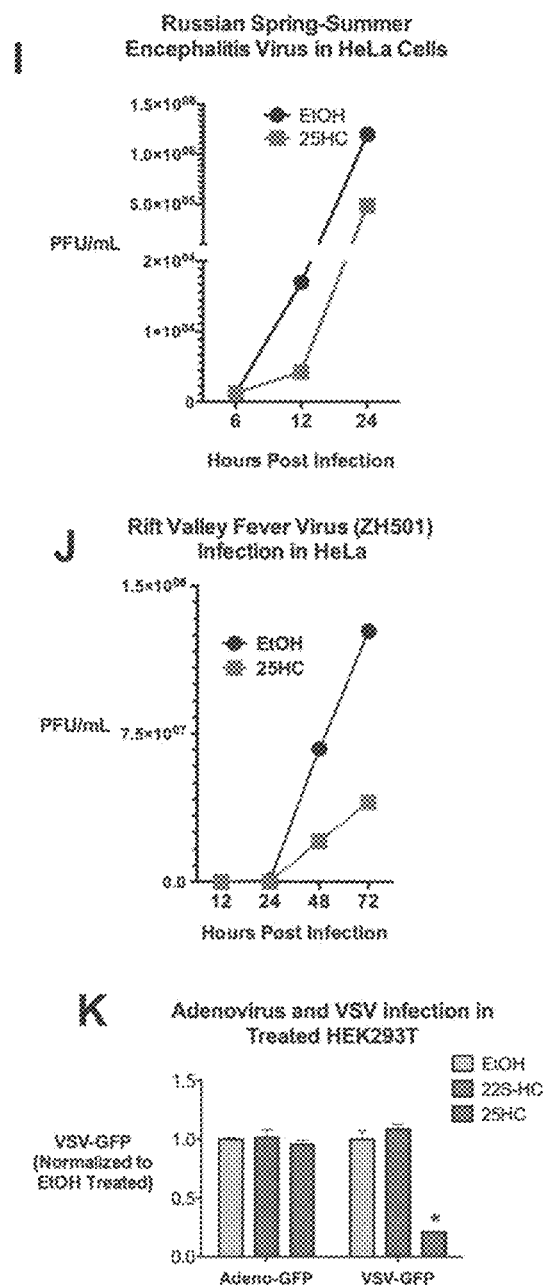
Fig. 4, cont'd.

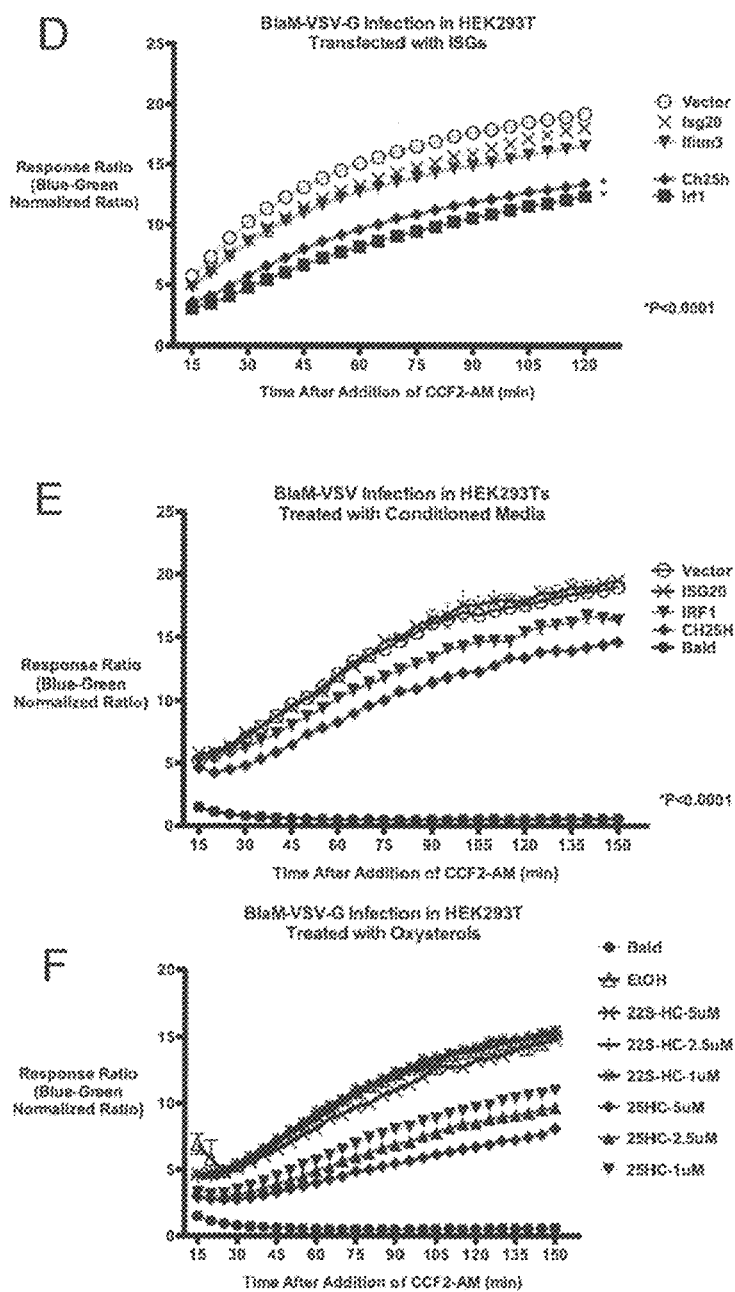
*Fig. 5, cont'd.*

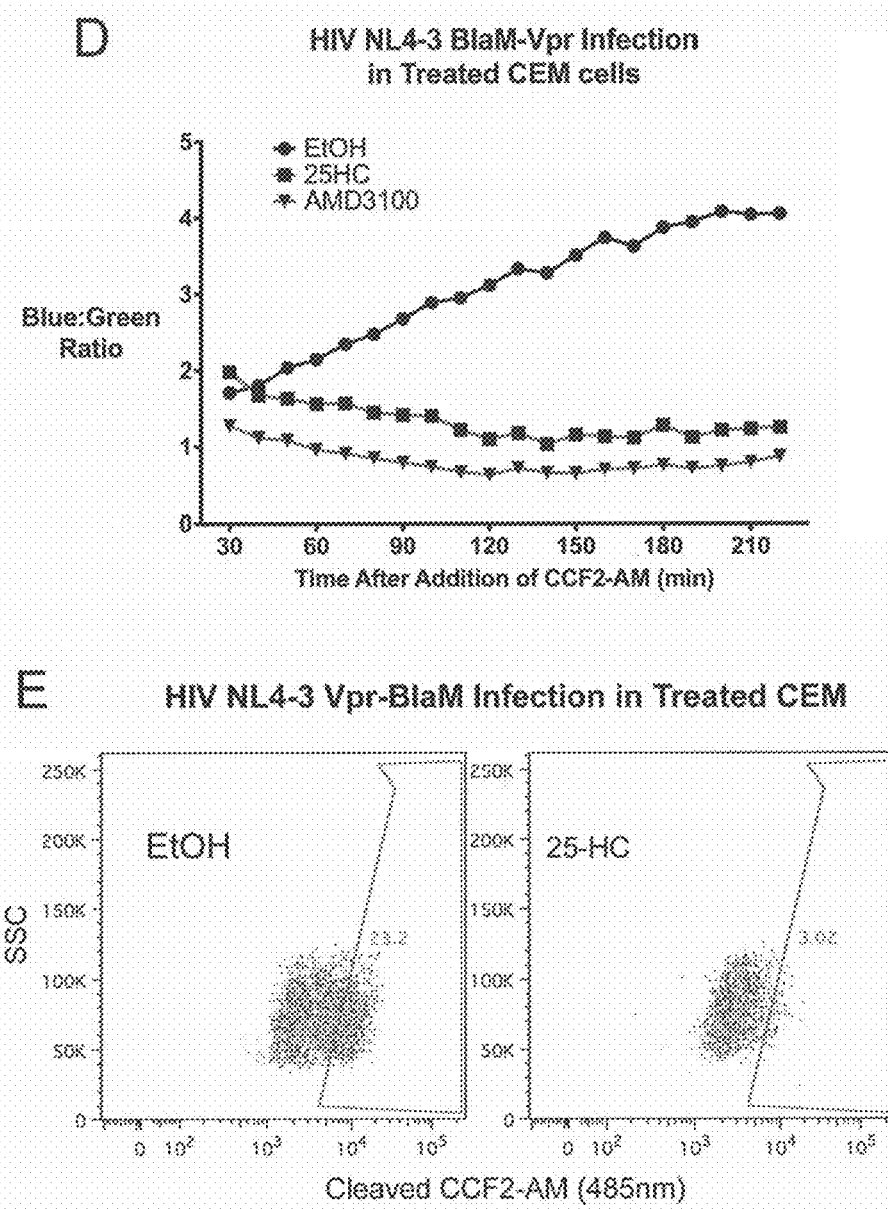
Fig. 6, cont'd.

Fig. 6, cont'd.

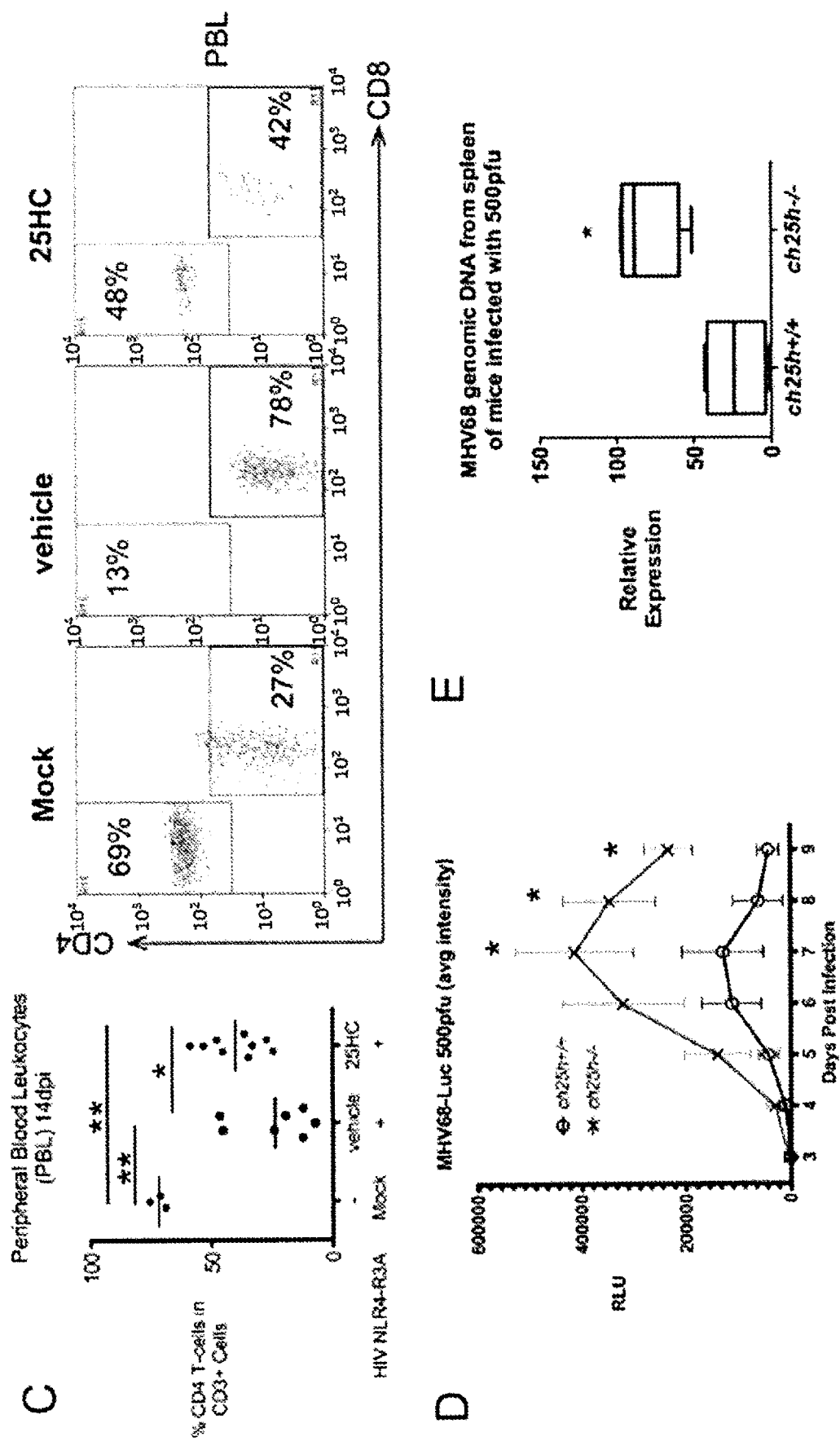
Fig. 7, cont'd

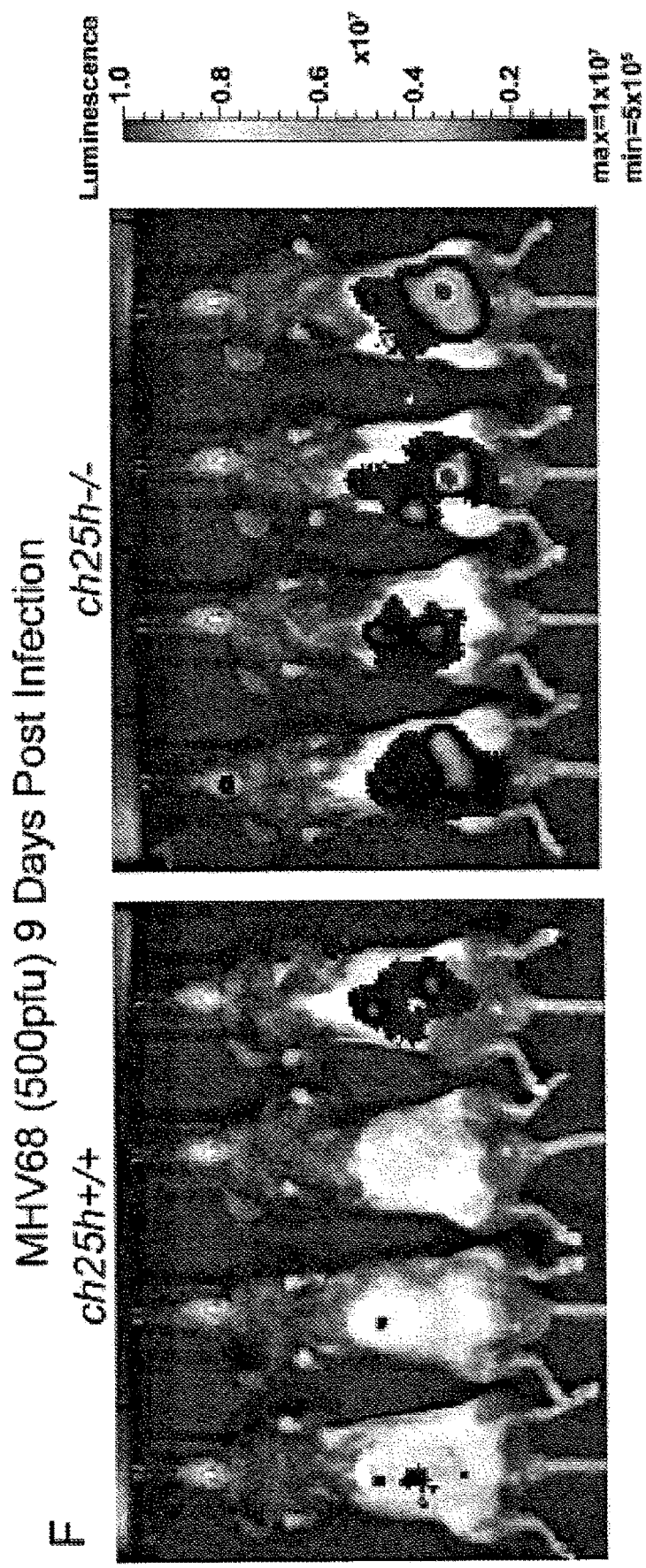
Fig. 7, cont'd

Fig. 11

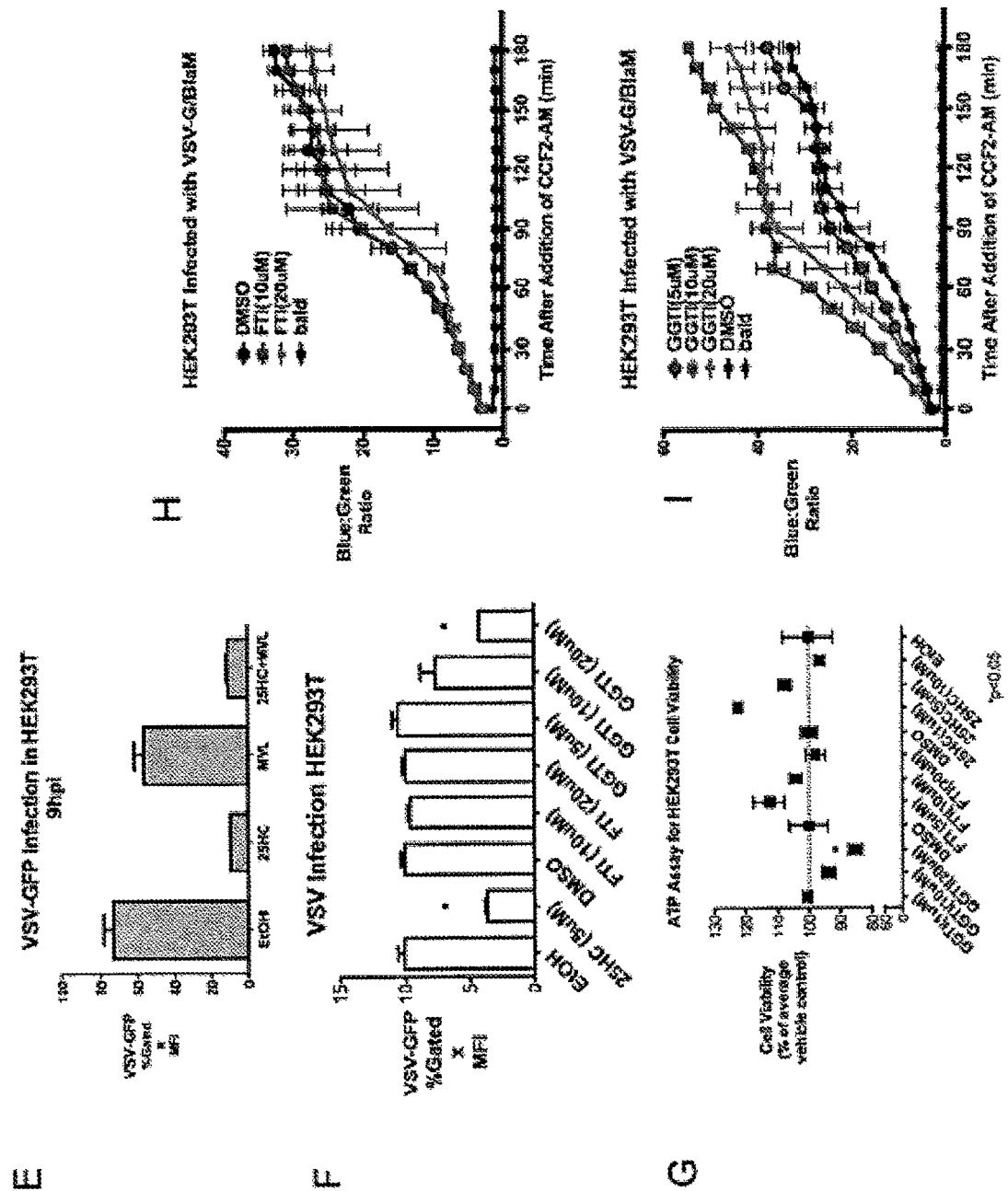
Fig. 17, cont'd

SEQUENCE LISTING

```
<160> NUMBER OF SEQ ID NOS: 13

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tgctacaacg gttcggagc                                                    19

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
agaagcccac gtaagtgatg at                                                22

<210> SEQ ID NO 3
<211> LENGTH: 19
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 3
aagcgaaact ggcggaaac                                                      19

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
taaccgatgt tgggcatcag                                                     20

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gatagtaccg gaggattgac gacta                                               25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gatagtaccg gaggattgac gacta                                               25

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tcaaaccatc cgagccattc                                                     20

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' FAM
<220> FEATURE:
<223> OTHER INFORMATION: 3' TAMRA

<400> SEQUENCE: 8
tgcaccgcca caaggcagag a                                                   21

<210> SEQ ID NO 9
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tgtgtgcccg tctgttgtgt                                                    20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gagtcctgcg tcgagagagc                                                    20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' FAM
<220> FEATURE:
<223> OTHER INFORMATION: 3' TAMRA

<400> SEQUENCE: 11
cagtggcgcc cgaacaggga                                                    20

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
acccactccc tcttagccaa tatt                                               24

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gtagggctag gcccaccg                                                      18
```

BROAD ANTIVIRAL THERAPY WITH MEMBRANE MODIFYING OXYSTEROLS

This application claims the benefit of the filing date of U.S. Provisional application 61/643,110, filed May 4, 2012, which is incorporated by reference herein in its entirely.

SEQUENCE LISTING

The instant application contains a Sequence Listing which has been submitted in ASCII format via EFS-Web and is hereby incorporated by reference in its entirety. Said ASCII copy, created on May 3, 2013, is named 58086-347965_SL.txt and is 3,313 bytes in size.

BACKGROUND INFORMATION

Viruses are obligate intracellular pathogens that—despite having unique structure and function—undergo lifecycle stages of entry, replication, protein synthesis, assembly, and egress. Upon specific binding to cell surface molecules, non-enveloped virus can enter the cell directly while enveloped viruses undergo fusion process that requires specific interactions between the viral and cellular receptors and membranes. After entry, viral components are released into the cytoplasm and may enter the nucleus. Although incipient viral proteins may be sufficient to initiate early lifecycle processes, full viral replication, transcription and translation require utilization of cellular factors. The newly synthesized viral proteins and genome are then coordinately assembled into virions, which then exit the cell by lysis or budding.

While viruses exploit host factors to successfully replicate, the innate immune system produces interferons (IFN), essential antiviral cytokines that induce wide array of antiviral effectors. Individually, many of these IFN-stimulated genes (ISGs) work to inhibit virus at particular stages of its lifecycle. IFITM proteins block viral entry and ISG20, a 3-5' exonuclease, degrades single stranded viral RNA; PKR inhibits viral translation through suppression of eIF2a elongation factors and tetherin prevents release of virions from the cell (Degols et al., June; Garcia et al., 2006; Brass et al., 2009; Perez-Caballero et al., 2009). These ISGs exemplify only a few of the hundreds of confirmed ISGs; most of them are uncharacterized.

Cholesterol-25-hydroxylase (Ch25h) is an ISG conserved across many species, including mammalian species. The intronless gene encodes an endoplasmic-reticulum-associated enzyme that catalyzes oxidation of cholesterol to 25-hydroxycholesterol ("25HC") (Holmes et al., 2011). 25HC belongs to a diverse class of endogenous oxysterols, the oxidation products of cholesterol. It is widely understood as a soluble factor that control sterol biosynthesis through regulation sterol-responsive element binding proteins (SREBP) and nuclear receptors (Kandutsch et al., 1978; Janowski et al., 1999). While oxysterols have unique roles in metabolism, studies have implicated their importance in immunity. Macrophages and B-cells express Ch25h robustly in response to various toll-like receptor (TLR) ligands and IFN (Bauman et al., 2009; Park and Scott, 2010). Ch25h suppresses IgA production in B-Cells and may promote intracellular bacterial growth by induction of prosurvival factors in macrophages (Bauman et al., 2009; Zou et al., 2011). Like immune mediators, dysregulation of 25HC is associated with immune pathology such as atherosclerosis (Andrew J and Jessup, 1999), partly attributed to its induction of inflammatory cytokine, IL-8 (Wang et al., 2012). Although these studies support a conserved immunological role of Ch25h and 25HC, their roles in the immune system remain elusive.

Antiviral therapies have been reported which act as viral entry blockers; these are generally specific for particular viruses because they block specific cellular or viral receptors required for entry. These are exemplified, e.g., by HIV entry inhibitors AMD3100 (see, e.g., Briz et al. J. Antimicrob. Chemother. (April 2006) 57(4): 619-62). A few broad viral entry inhibitors have been reported which work by modification of viral membrane (see, e.g., Wolf et al. PNAS 2010 107 (7) 3157-3162). There is a need for new viral inhibitors which can act generally against a broad range of viruses.

Figure 6:
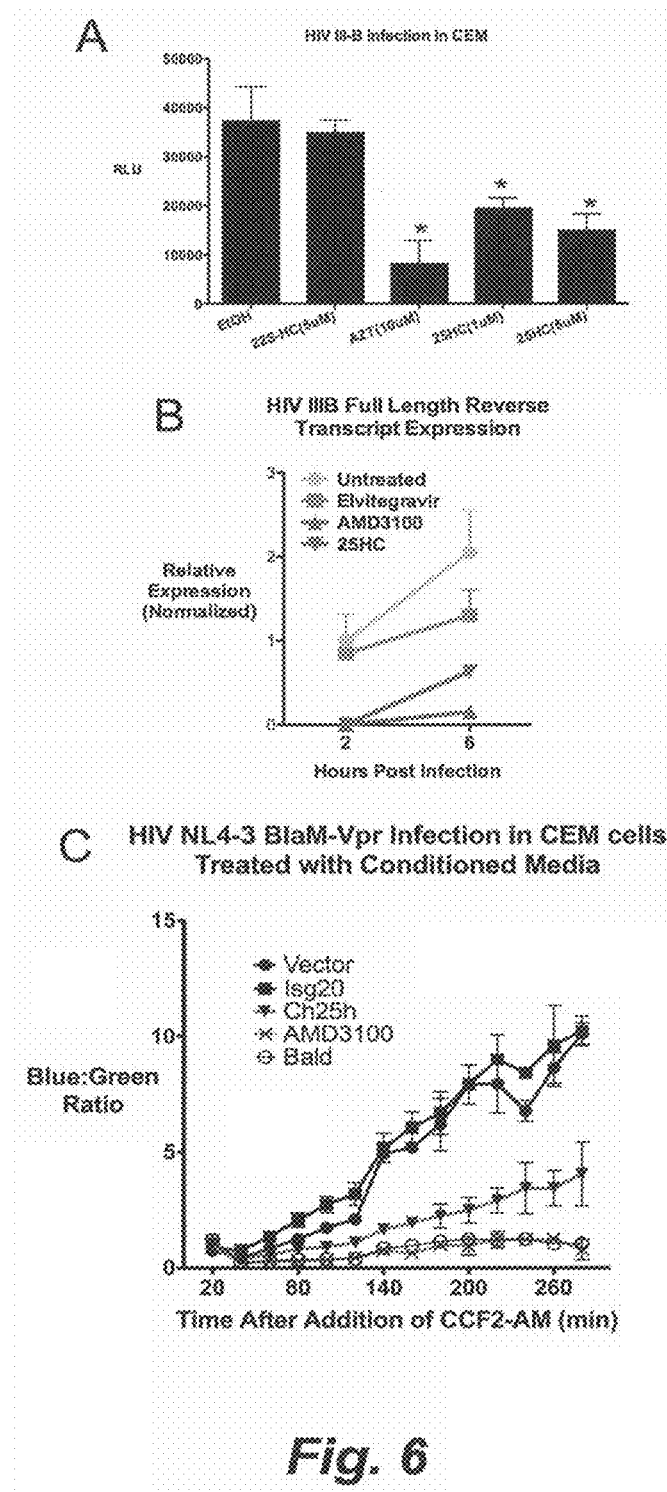
FIG. 6. (A) CEM cells were treated as indicated for 12 h and infected with HIV-IIIB coexpressing luciferase, which can only undergo single-round infection. Cell lysates were collected after 24 h and measured for luciferase activity. Relative Light Units (RLU) is represented as Mean±SD *P<0.05. (B) CEM cells were treated with Integration inhibitor, elvitegravir, AMD3100 (10 µM), 25HC (1 µM), and vehicle (EtOH) for 12 h and infected with HIV III-B pseudovirus. At 2 and 6 hpi, total cellular DNA was collected and HIV full-length late reverse transcript (LateRT) was quantified by qRT-PCR with Taqman probe. (C) CEM cells were treated with indicated conditioned media for 8 h and infected with HIV NL4-3 encoding Vpr-BlaM (NL4-3/BlaM) in duplicates. AMD3100 serve as positive control for entry inhibition. Beta-lactamase activity was measured by cleavage of CCF2-AM by fluorescence plate reader. *P<0.01. (D) CEM cells were treated with indicated 25HC (5 µM) and vehicle (EtOH) for 8 h and infected with HIV NL4-3 encoding Vpr-BlaM (NL4-3/BlaM). AMD3100 serve as positive control for entry inhibition. Beta-lactamase activity was measured by cleavage of CCF2-AM. (E) Similar to FIG. 6E. CCF2-AM cleavage was confirmed by FACs. Numbers represent percentage cells expressing cleaved form of CCF2AM (485 nm). (F) Vero cells were transfected with Nipah F and G receptors. 5 h after transfection, the cells were treated with indicated conditions. The cells were fixed 21 h after transfection and Giemsa stained.
Figure 18:
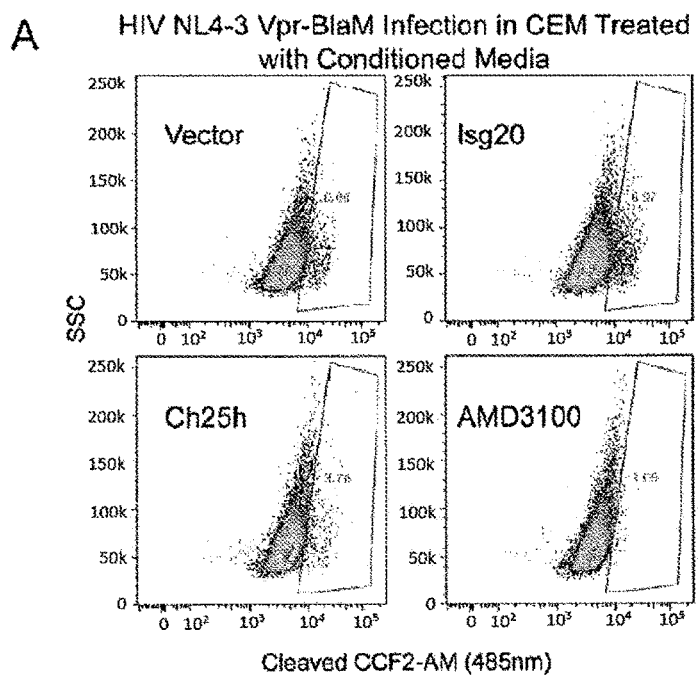
Figure 18:
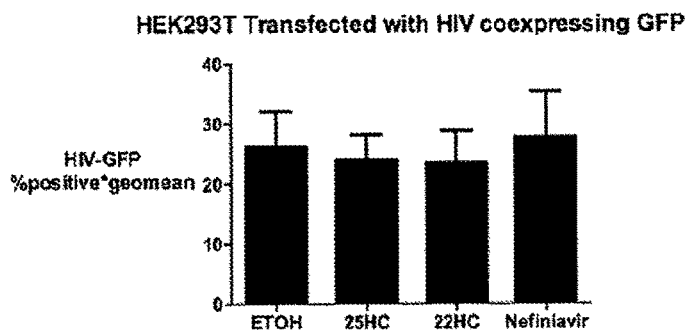
Figure 18:
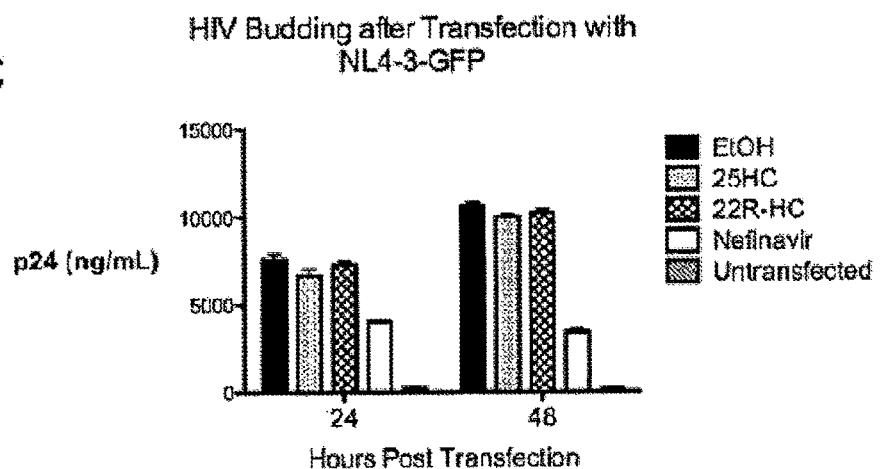

FIG. 18. (A) CEM cells were treated with indicated conditioned media for 8 h and spin-infected with HIV NL4-3 encoding Vpr-BlaM (NL4-3/BlaM) in duplicates for 2 h. CCF2-AM substrate was added and βla activity was measured for 4 h at room temperature as shown in FIG. 6.C. After the kinetic read, CCF2-AM cleavage was confirmed by FACs with gating on percentage cells expressing cleaved form of CCF2AM (blue, 485 nm). (B) HEK293T were transfected with proviral plasmid of HIV coexpressing GFP and treated with indicated agonists 6 h after transfection. HIV-GFP was quantified by FACs after 48 h. Mean±SEM. (C) Viral supernatants from part A were collected after 48 h and p24 was quantified by ELISA. Mean±SD.

DESCRIPTION

The present inventors have found that 25-hydroxycholesterol (25HC) and its derivatives or analogs are useful for antiviral therapy against a broad spectrum of enveloped viruses, both for treatment and for prophylaxis of viral infections. Without wishing to be bound by any particular mechanism, it is suggested that 25HC inhibits viral entry into cells by modification of cellular membranes. 25 HC is disclosed herein to be effective, both in vitro and in vivo (in a subject) for inhibiting, e.g., vesicular stomatitis virus (VSV), herpes simplex virus (HSV), murine gammaherpes virus (MHV68), hepatitis C virus (HCV), human-immunodeficiency virus (HIV), Ebola virus (EBOV), Rift Valley Fever virus (RVFV), Russian Spring-Summer Encephilitis virus (RSSEV) and Nipah viruses. Some of these viruses, such as Ebola and Rift Valley Fever virus, are highly pathogenic.

The Examples herein demonstrate the inhibitory effect of 25HC on a variety of enveloped viruses, including highly pathogenic viruses; and they show that 25HC reduces HIV replication in humanized mouse models.

One advantage of the compounds and methods of the present invention is that the compounds broadly inhibit viral infection, including the viruses noted above and other enveloped viruses. Furthermore, 25HC is an endogenously produced product. Hence, its toxicity is better tolerated than other chemical compounds, such as agents targeted against cellular metabolic functions.

One aspect of the invention is a method for inhibiting the growth and/or proliferation and/or infectivity of a virus in a cell, comprising administering, or causing to be administered, to the cell, 25-hydroxycholesterol (25HC) in an amount sufficient to inhibit the growth and/or proliferation and/or infectivity of the virus in the cell, wherein, if the cell is in vitro, the 25HC is administered to the cell, and the virus is vesicular stomatitis virus (VSV), herpes simplex virus (HSV), murine gammaherpes virus (MHV68), hepatitis C virus (HCV), Ebola virus (EBOV), or Nipah virus; and wherein, if the cell is in a subject, the 25HC is administered or caused to be administered to the subject, and the virus is vesicular stomatitis virus (VSV), herpes simplex virus (HSV), murine gammaherpes virus (MHV68), hepatitis C virus (HCV), human-immunodeficiency virus (HIV), Ebola virus (EBOV), or Nipah virus.

Embodiments of this method include a method for preventing the viral infection of a cell (e.g., a mammalian cell) in vitro or in a subject; and a method for inhibiting entry of the virus into a cell (e.g., a mammalian cell) in vitro or in a subject.

In embodiments in which the 25HC is administered to a subject, it can be administered by a route selected from the group consisting of topical administration, oral administration; nasal administration, rectal administration, vaginal administration, intraperitoneal injection, intravascular injection, subcutaneous injection, transcutaneous administration, inhalation administration, and intramuscular injection. It can be administered topically, vaginally, rectally, or to the buccal cavity. It can be administered to a mucosal surface.

In embodiments in which the 25HC is administered to a subject, it can be formulated as a cream, gel, or foam for rectal delivery or vaginal delivery or topical administration; as a mouthwash for delivery to the buccal cavity; or for oral or intravenous delivery (e.g., the 25HC is solubilized in (2-hydroxy)-beta-cyclodextrin).

In embodiments of the invention, the 25HC is administered to a mammalian cell, and/or to a mammal, wherein the cell or mammal is either a non-human mammal or a human.

In one embodiment of the invention, the subject (e.g. human) to which the 25HC is administered is identified as being at risk for an infection by the virus. In this embodiment, the 25HC is administered prior to viral infection and prevents the viral infection (e.g., prevent entry of the virus into cells in the subject).

In another embodiment of the invention, the subject (e.g. human) to which the 25HC is administered is identified as having an infection by the virus. In this embodiment, the administration of the 25HC treats the viral infection.

Another aspect of the invention is a method for identifying putative inhibitors of viral entry into cells which exhibit lower levels of side effects than does 25HC, comprising testing analogs of 25HC in vitro for their ability to: a) exhibit anti-viral activity; b) exhibit lower levels of cell cytoxicity (statistically significant reductions in the level of cytotoxicity being measured in an assay) than does a suitable control, such as 25HC; and c) inhibit lipid metabolism to a lower level (exhibit a statistically significantly lower level of inhibition) than does a suitable control, such as 25HC. In embodiments of the invention, one can employ basic metabolic assays, such as for cholesterol or triglycerides, or can assay for SREBP processing. For example, if an agent inhibits SREBP processing to a lower level (exhibit a statistically significantly lower level) than does a suitable control, such as 25HC, it is a good candidate for an agent that does not cause undesirable side effects.

Any of a variety of enveloped viruses can be inhibited by a method of the invention. These include, e.g., VSV, HSV, MHV68, HCV, HIV (any of a variety of strains, which will be evident to one of skill in the art), EBOV, RVFV, RSSEV and Nipah virus. Other enveloped viruses that can be inhibited include, e.g., other herpes viruses, Pox virus, Reo virus, Filo virus, Hepatitis D virus, Corona virus, Toga virus, and other Retroviruses.

Viruses for which the inventive method can be used include the following:
DNA Viruses
  Herpesviruses, including HHV-1 to HHV-8
  Poxviruses, including Orthopox (smallpox virus (variola), vaccinia virus, cowpox virus, monkeypox virus); Parapox (orf virus, pseudocowpox, bovine papular stomatitis virus); Yatapox (tanapox virus, yaba monkey tumor virus); Molluscipox (molluscum contagiosum virus (MCV))

Hepadnaviruses, including Hepatitis B

RNA Viruses

Flavivirus, including West Nile virus, dengue virus, tick-borne encephalitis virus, yellow fever virus Togavirus, including Genus Alphavirus: Sindbis virus, Eastern equine encephalitis virus, Western equine encephalitis virus, Venezuelan equine encephalitis virus, Ross River virus, O'nyong'nyong virus, Chikungunya, Semliki Forest virus; and Genus Rubivirus: Rubella virus Coronavirus Hepatitis C and Hepatitis D Orthomyxovirus, including Influenzavirus A, Influenzavirus B, Influenzavirus C, Isavirus, Thogotovirus Paramyxovirus, including mumps, measles, respiratory syncytial virus (RSV), parainfluenza viruses, Human metapneumovirus, canine distemper virus (dogs), phocine distemper virus (seals), cetacean morbillivirus (dolphins and porpoises), Newcastle disease virus (birds), and rinderpest virus (cattle), henipaviruses including Hendra virus (HeV) and Nipah virus (NiV)

Rhabdovirus, including RaV (Rabies virus), VSV (Vesicular stomatitis virus)

Bunyavirus, including Hantavirus (Hantaan virus), Nairovirus (Dugbe virus), Orthobunyavirus (Bunyamwera virus), Phlebovirus (Rift Valley fever virus)

Filovirus, including Cuevavirus, Ebolavirus, and Marburgvirus

Retroviruses, including Alpharetrovirus (Avian leukosis virus, Rous sarcoma virus), Betaretrovirus (Mouse mammary tumour virus), Gammaretrovirus (Murine leukemia virus, Feline leukemia virus), Deltaretrovirus (Bovine leukemia virus, Human T-lymphotropic virus), Epsilonretrovirus (Walleye dermal sarcoma virus), Lentivirus (Human immunodeficiency virus, Simian, Feline immunodeficiency viruses), Spumavirus (Simian foamy virus).

When 25HC is referred to herein, it is to be understood that this term can include stereoisomers thereof, including diastereomers, racemates, enantiomers and other isomers of the compound. Conventional pharmaceutically acceptable salts or solvates of 25HC are also included.

The meanings of some of terms, as used herein, are indicated below.

A "derivative" of a compound, as used herein, refers to a chemically modified compound wherein the chemical modification takes place at one or more functional groups of the compound. The derivative however, is expected to retain, or enhance, the pharmacological activity of the compound from which it is derived.

As used herein, "administering" refers to local and/or systemic administration, e.g., including enteral, parenteral, pulmonary, and topical/transdermal administration. Routes of administration that find use in the methods described herein include, e.g., oral (per os (p.o.)) administration, nasal or inhalation administration, administration as a suppository, topical contact, transdermal delivery (e.g., via a transdermal patch), intrathecal (IT) administration, intravenous ("iv") administration, intraperitoneal ("ip") administration, intramuscular ("im") administration, intralesional administration, or subcutaneous ("Sc") administration, or the implantation of a slow-release device e.g., a mini-osmotic pump, a depot formulation, etc., to a subject. Administration can be by any route including parenteral and transmucosal (e.g., oral, nasal, vaginal, rectal, or transdermal). Parenteral administration includes, e.g., intravenous, intramuscular, intra-arterial, intradermal, subcutaneous, intraperitoneal, intraventricular, ionophoretic and intracranial. Other modes of delivery include, but are not limited to, the use of liposomal formulations, intravenous infusion, topical administration, transdermal patches, etc. 25HC is effective as a topical agent to prevent viral infections in which viruses enter cells by penetration of the skin or transmittal across mucosal surfaces. Such infections include, e.g., Herpes Simplex Infections, HIV, or other sexually-transmitted diseases.

The terms "systemic administration" and "systemically administered" refer to a method of administering the agent (s) described herein or composition to an animal (e.g. mammal) or plant so that the agent(s) or composition is delivered to sites in the body, including the targeted site of pharmaceutical action, via the circulatory system. Systemic administration to animals such as mammals includes, but is not limited to, oral, intranasal, rectal and parenteral (e.g., other than through the alimentary tract, such as intramuscular, intravenous, intra-arterial, transdermal and subcutaneous) administration.

The term "effective amount" or "pharmaceutically effective amount" refer to the amount and/or dosage, and/or dosage regime, of one or more agent(s) sufficient to bring about a measurable or detectable amount of the desired result e.g., prophylaxis or treatment of a viral infection in a subject (e.g. mammal), or lessening the severity or delaying the progression of a viral infection in a subject (e.g. mammal).

In general, 25HC stimulates a therapeutic response (e.g., inhibits growth and/or proliferation and/or infectivity of a virus in a cell, and/or prevents a viral infection of a cell, and/or which inhibits entry of a virus into a cell) to a statistically significant degree compared to a suitable control, such as treatment with a buffer or other solution lacking 25HC. For example, in embodiments of the invention, 25HC can stimulate a therapeutic response, as measured by any of a variety of conventional assays, by about 1%, 5%, 10%, 20%, 30%, 40%, 50% 150%, 200%, 400% or 600% or more of that in an untreated control sample. Intermediate values in these ranges are also included.

One skilled in the art can routinely determine the appropriate dose, schedule, and method of administration for the exact formulation of the composition being used, in order to achieve the desired effective amount or effective concentration of the agent in the individual patient. One skilled in the art also can readily determine and use an appropriate indicator of the "effective concentration" of a compound, for example, 25HC, by a direct or indirect analysis of appropriate patient samples (e.g., blood and/or tissues), in addition to analyzing the appropriate clinical symptoms of the disease, disorder, or condition.

The exact dose of 25HC or composition thereof administered to an animal, such as a human, in the context of the present invention will vary from subject to subject, depending on the species, age, weight and general condition of the subject, the severity or mechanism of any disorder being treated, the particular agent or vehicle used, its mode of administration, other medications the patient is taking and other factors normally considered by an attending physician, when determining an individual regimen and dose level appropriate for a particular patient, and the like. The dose used to achieve a desired concentration in vivo will be determined by the potency of the form of the 25HC, the pharmacodynamics associated with the 25HC in the host, with or without additional agents, the severity of the disease state of infected individuals, as well as, in the case of systemic administration, the body weight and age of the individual. The size of the dose may also be determined by the existence of any adverse side effects that may accompany the particular agent, or composition thereof, employed. It is generally desirable, whenever possible, to keep adverse side effects to a minimum.

For example, a dose can be administered in the range of from about 5 ng (nanograms) to about 1000 mg (milligrams), or from about 100 ng to about 600 mg, or from about 1 mg to about 500 mg, or from about 20 mg to about 400 mg. For example, the dose can be selected to achieve a dose to body weight ratio of from about 0.0001 mg/kg to about 1500 mg/kg, or from about 1 mg/kg to about 1000 mg/kg, or from about 5 mg/kg to about 150 mg/kg, or from about 20 mg/kg to about 100 mg/kg. For example, a dosage unit can be in the range of from about 1 ng to about 5000 mg, or from about 5 ng to about 1000 mg, or from about 100 ng to about 600 mg, or from about 1 mg to about 500 mg, or from about 20 mg to about 400 mg, or from about 40 mg to about 200 mg of 25HC or a composition comprising 25HC.

The phrase "cause to be administered" refers to the actions taken by a medical professional (e.g., a physician), or a person controlling medical care of a subject, that control and/or permit the administration of the agent(s) at issue to the subject. Causing to be administered can involve diagnosis and/or determination of an appropriate therapeutic or prophylactic regimen, and/or prescribing particular agent(s) for a subject. Such prescribing can include, for example, drafting a prescription form, annotating a medical record, and the like.

As used herein, the terms "treating" and "treatment" refer to delaying the onset of, retarding or reversing the progress of, reducing the severity of, or alleviating or preventing either the disease or condition to which the term applies, or one or more symptoms of such disease or condition.

The terms "subject," "individual," and "patient" interchangeably can refer to any organism which contains cholesterol-25-hydroxylase and thus can be treated with 25HC. Suitable subjects include plants (e.g., rice (*Oryza saliva*) or thale cress (*Arabidopsis thaliana*)) or animals, such as, e.g., poultry, the worm *Caenorhabditis*, or a mammal. The type of subject being discussed herein will be evident from the context of the discussion. In many embodiments of the invention, the subject is a mammal, e.g. a human or a non-human primate, but also domesticated mammals (e.g., canine or feline), laboratory mammals (e.g., mouse, rat, rabbit, hamster, guinea pig) and agricultural mammals (e.g., equine, bovine, porcine, ovine). In various embodiments, the subject can be a human (e.g., adult male, adult female, adolescent male, adolescent female, male child, female child) under the care of a physician or other healthworker in a hospital, psychiatric care facility, as an outpatient, or other clinical context. In certain embodiments the subject may not be under the care or prescription of a physician or other healthworker.

The term "formulation" or "drug formulation" or "dosage form" or "pharmaceutical formulation" as used herein refers to a composition containing at least one therapeutic agent or medication for delivery to a subject. In certain embodiments the dosage form comprises a given "formulation" or "drug formulation" and may be administered to a patient in the form of a lozenge, pill, tablet, capsule, suppository, membrane, strip, liquid, patch, film, gel, foam, spray, or other form.

In aspects of the invention, the 25HC is in the form of a pharmaceutical composition comprising 25 HC and a pharmaceutically acceptable carrier. By a "pharmaceutically acceptable carrier" is meant a material that is not biologically or otherwise undesirable, i.e., the material may be administered to a subject without causing any undesirable biological effects or interacting in a deleterious manner with any of the other components of the pharmaceutical composition in which it is contained. The carrier is naturally selected to minimize any degradation of the active ingredient and to minimize any adverse side effects in the subject, as would be well known to one of skill in the art. For a discussion of pharmaceutically acceptable carriers and other components of pharmaceutical compositions, see, e.g., Remington's Pharmaceutical Sciences, 18th ed., Mack Publishing Company, 1990. Some suitable pharmaceutical carriers will be evident to a skilled worker and include, e.g., water (including sterile and/or deionized water), suitable buffers (such as PBS), physiological saline, cell culture medium (such as DMEM), artificial cerebral spinal fluid, or the like.

The term "mucosal membrane" refers generally to any of the mucus-coated biological membranes in the body. In certain embodiments active agent(s) described herein can be administered herein via any mucous membrane found in the body, including, but not limited to buccal, perlingual, nasal, sublingual, pulmonary, rectal, and vaginal mucosa. Absorption through the mucosal membranes of the oral cavity and those of the gut are of interest. Thus, peroral, buccal, sublingual, gingival and palatal absorption are contemplated herein.

In various embodiments the 25-hydroxycholesterol can be incorporated into different therapeutic delivery systems. For example, it can be incorporated as creams, gels, or foams to serve as topical treatment for viral infection or for rectal or vaginal application (e.g. to mucosal surfaces). In certain embodiments oral or intravenous delivery, 25-hydoxycholesterol can be solubilized, e.g., in (2-hydroxy)-beta-cyclodextrin.

In certain embodiments the 25HC is applied primarily for prevention of infection. In certain embodiments the compound (or formulation thereof) is applied directly to a site of viral entry (e.g., to the skin, to the buccal cavity, rectally, vaginally, etc.). As a cream or a solubilized form, the 25HC can be applied directly and prior to infection. In certain embodiments they can be used for various oral or sexually transmitted diseases, such as HSV and HIV.

One aspect of the invention is a screening method to identify agents (such as derivatives, analogs or modifications of 25HC) which can inhibit the growth and/or proliferation and/or infectivity of an enveloped virus in a cell (e.g., which can inhibit entry of the virus into the cell). The assay takes advantage of the findings shown herein that 25HC efficiently inhibits entry of the viruses into the cells, yet does not appear to negatively affect metabolic cellular functions, and thus would be expected to elicit fewer side effects than agents which target such metabolic functions. Putative agents are tested, using conventional methods and/or methods described herein, for three different parameters: 1) cell cytotoxicity; 2) anti-viral properties; 3) inhibitory effects on SREBP processing. Lactate dehydrogenase (LDH) and 3-(4,5-dimethylthiazol-2-yl) 2,5-diphenyl-tetrazolium bromide (MTT) assays are employed to assess cell cytotoxicity. A wide range of primary human cells are used, which are derived from induced pluripotent stem (iPS) cells (e.g., provided by the PSC Scientific Core) including Neuron cells, Astrocytes, Hepatocytes, Endothelial cells, Blood Brain Barrier cells, Lung Epithelial cells, Macrophages and Dendritic cells. These cell lines are treated at different concentrations of test compounds (0 uM-20 uM) and cytotoxic effects are evaluated at 12, 24, 48 and 72 hours post treatment using LDH and MTT assays. Most of the viral infections used in this assay method are completed within 24 hours, but tests are nevertheless performed also at 48 and 72 hours post treatment to obtain better understanding of potential cytotoxic effects of the test compounds. For assessing anti-viral activities, primary human cells are infected (e.g. as described in the Examples herein) with, e.g., RVFV, LCMV, VSV, YFV and/or influenza viruses in the presence of different concentrations of test compounds (e.g. 25HC analogs or derivatives), at 0 uM-20 uM. Viral concentrations in different samples are measured by conventional plaque assays. Furthermore, the anti-viral effects are confirmed to be due to their ability to inhibit viral entry, using conventional methods such as those described herein, including VSV and Influenza J3-lactamase entry assays. Finally, the test compounds are examined for their ability to modulate lipid metabolism. SREBP1 and 2 processing are used as the readout, using western blotting analysis to monitor levels of active/nuclear form of SREBPs after treatment of cells with the test compounds (e.g. new 25HC derivatives). 25HC administration inhibits the cleavage of SREBP1 and 2 to their mature nuclear form. Therefore, compounds are selected which do not inhibit SREBP processing. In embodiments of the invention, putative inhibitory compounds are tested by validation in conventional animal models.

In embodiments of the invention, agents that appear promising in the in vitro assays discussed above are further tested to toxicity in vivo. For example, toxicity as measured by liver damage can be tested in animal models by assaying for Aspartate Aminotransferase (AST) or alanine aminotransferase, using conventional methods.

In the foregoing and in the following examples, all temperatures are set forth in uncorrected degrees Celsius; and, unless otherwise indicated, all parts and percentages are by weight.

EXAMPLES

The following, examples are offered to illustrate, but not to limit the claimed invention.

Example 1—the Interferon-Inducible Cholesterol-25-Hydroxylase Broadly Inhibits Viral Entry by Production of 25-Hydroxycholesterol Highlights Ch25h is an IFN-dependent gene that inhibits virus by production of soluble endogenous antiviral oxysterol 25-hydroxycholesterol (25HC).

Ch25h and 25HC broadly inhibit viruses including VSV, HSV, HIV, MHV68.

25HC inhibits live, highly-pathogenic Ebola, Nipah, Russian Spring-Summer Encephilitis, Rift-Valley Fever Viruses.

25HC inhibits viral entry of VSV and HIV.

25HC inhibits viral mediated membrane fusion.

ch25h-deficient cells and mice have increased susceptibility to acute viral infections.

Administration of 25-hydroxycholesterol in vivo suppresses HIV replication in humanized mouse model.

Abstract of Example 1

Interferons (IFN) are essential cytokine for innate immunity against viral infection and generate the cellular antiviral state through upregulation of interferon-stimulated genes (ISGs). We identified Cholesterol-25 hydroxylase (Ch25h) as an antiviral ISG and demonstrated that it broadly inhibits enveloped viruses including VSV, HSV, HIV, and MHV68. It also inhibits replication of acutely pathogenic EBOV, RVFV, RSSEV, and Nipah under BSL4 conditions. Functional loss of Ch25h in Ch25h-knockdown and Ch25h-deficient cell lines led to increased susceptibility to viral infection in vitro. 25HC inhibits VSV and HIV cellular entry by modification of cellular membrane. We further showed that this modification causes defect in membrane fusion between virus and cell. In vivo, administration of 25HC in humanized mice suppressed HIV replication and rescued T-cell depletion. Moreover, Ch25h-knockout mice demonstrated increased susceptibility to MHV68 lytic infection. Our findings show Ch25h as a unique antiviral ISG that generates a soluble antiviral factor and demonstrate the therapeutic potential of membrane-modifying oxysterols as viral entry inhibitors.

Results

Ch25h is an IFN-Dependent Gene with Antiviral Activity

Figure 1:
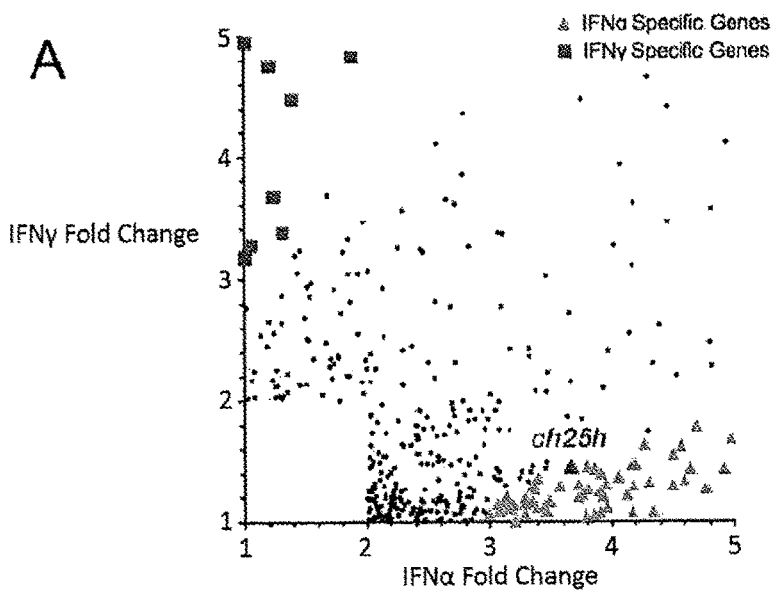
FIG. 1. (A) Ch25h is IFN inducible. Gene expression profile of BMMs treated for 2.5 h with IFNα and IFNγ at 62 U/mL and 1 U/mL, respectively. Axes represent fold change in response to IFNα or IFNγ over untreated cells. IFNα-stimulated genes that were 3-fold higher than induction of IFNγ stimulated genes were categorized as IFNα-specific (green). Similarly, IFNγ stimulated genes were defined this way (blue). Ch25h is highlighted in red. (B) Wildtype, IFNAR-deficient and IL-27R (TCCR/WSX-1) deficient BMMs were stimulated with LipidA (100 ng/mL) or saline control for 4 hr and 12 hr, respectively. CH25 expression values are presented as RKPM values. (C) Ch25h gene expression measured by qRT-PCR of ifnar+/+ and ifnar-/- BMMs stimulated with TLR agonists, Pam-3-Cys (100 ng/mL), polyI:C (25 ug/mL), lipidA (10 ng/mL), CpG-B (100 μM) for 4 hours. (D) HEK293T was co-transfected flourescent red marker (DsRed) and with individual plasmids encoding Tbk1, Ch25h, or vector for 36 h and infected with VSV-GFP (0.01 MOI) for 9 h. Representative contour plots are shown. (E) Effect of overexpression of individual ISGs and Ch25h on VSV-GFP in DsRed-positive population normalized to vector control. VSV-GFP was quantified by the product of percent GFP-positive population and geometric mean of the fluorescence index (MFI). Mean±SEM; *P<0.001.
Figure 1:
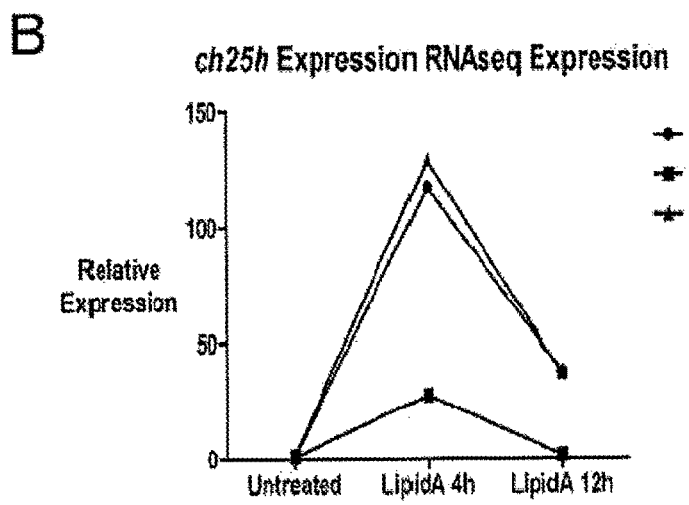
Figure 1:
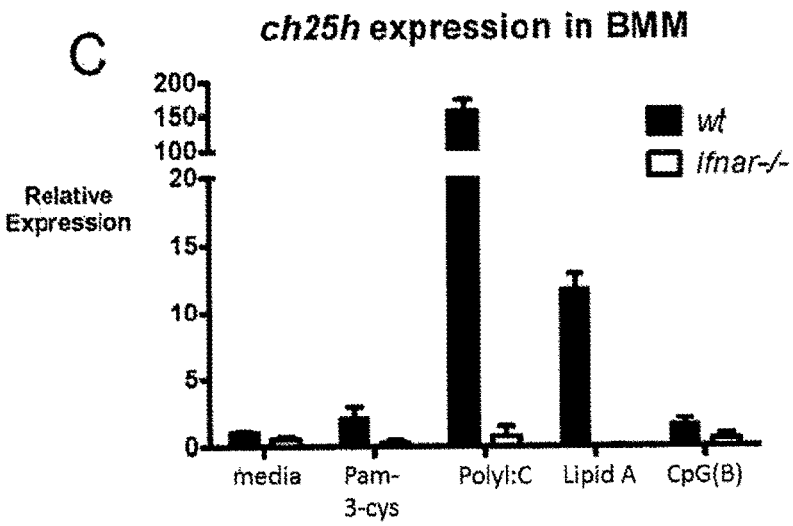

In a microarray analysis of IFNα and IFNγ stimulated murine bone marrow-derived macrophages (BMMs), we found both IFNs induced expression of Ch25h within 3 hrs (FIG. 1A). A subsequent RNAseq analysis showed the TLR4 agonist, lipidA, induced Ch25h expression. This induction was dependent on IFN receptor (IFNAR) but independent of IL-27, a cytokine that mediates IFN secondary gene expression, such as IL-10 (FIG. 1B). We further tested different TLR agonists and found dsRNA mimetic, polyI:C (TLR3 agonist), and lipidA induced Ch25h mRNA expression highly whereas Pam-3-Cys (TLR2 agonist) and CpG (TLR9 agonist) induced it less. IFNAR-deficient BMMs had abrogated Ch25h expression when treated with these agonists showing that Ch25h expression is IFN-dependent (FIG. 1C).

In a previous study, we sought antiviral ISGs against vesicular stomatitis virus (VSV) in a blinded and unbiased functional screen (Liu et al., 2012). Individual ISGs in expression plasmids were co-transfected with red fluorescent construct (DsRed) in HEK293T cells for 36 h and subsequently infected with VSV coexpressing GFP (VSV-GFP) for 9 h and analyzed by FACS. Active viral replication was measured by percentage and geometric mean fluorescence index (% GFP+× Geometric MFI) of GFP-positive cells in the DsRed population. TANK-binding kinase-1 (Tbk1), which is an activator of IFN production, was used as a positive control. The amount of infection was normalized to cells co-transfected with DsRed and control vector. Expression of Ch25h inhibited VSV-GFP replication by ~70% at 9 hpi (FIGS. 1. D and E). IFN activators like Tbk1, Ifih1 (Mda5), and Irf1 strongly inhibited VSV as well as the RNA exonuclease, ISG20.

Figure 2:
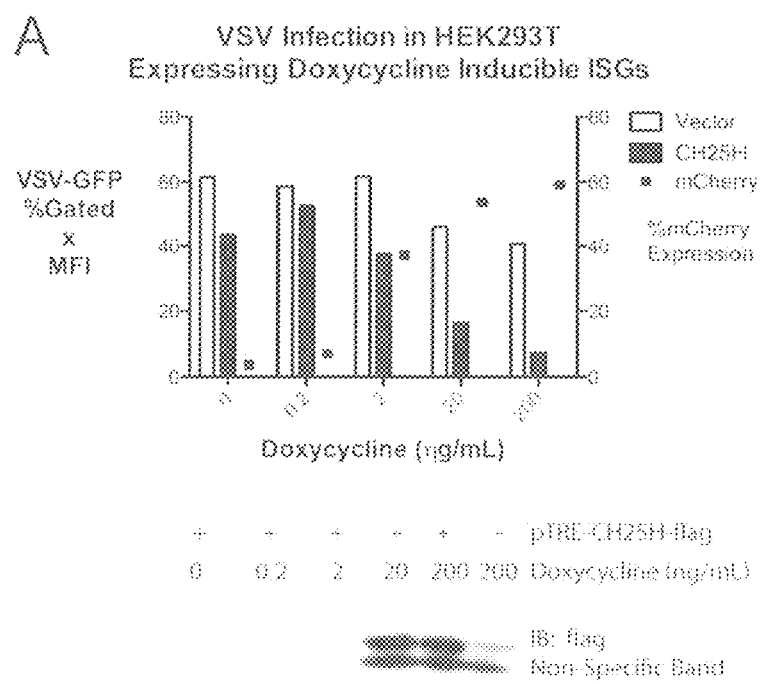
FIG. 2. (A) HEK293T expressing doxycycline-inducible construct coexpressing Ch25h-flag and red flourescent marker mCherry. HEK293T was transfected with vector or Ch25h encoding plasmids for 24 h and doxycycline was added for 12 h at indicated concentrations. Expression of Ch25h-flag was confirmed by western blot (upper panel). After treatment, cells were infected with VSV-GFP (0.01 MOI) for 9 hrs and VSV-GFP was quantified by (% GFP+X GeoMean MFI). Dots represent percent positive mCherry (lower panel). (B) RAW264.7 stably knocked down with shRNA against Ch25h were generated by retro-viral infection. Two shRNA constructs were made (shCh25h-A and shCH25h-B) along with scramble control. Knockdown was confirmed by qRT-PCR. *P<0.01. (C) shCH25h-A, shCH25hB, and scrambled stable RAW264.7 were infected with VSV-GFP (0.1 MOI) and the VSV-GFP was measured by plaque assay 14 hpi. (D) Individual clonal population of BCR-ABL transformed B-cells from ch25h+/+ and ch25h-/- mice were infected with VSV-GFP (0.1 MOI) in biological triplicates and the viral titers were measured by plaque assay at indicated times. *P<0.01. (E) J2 BMM were derived from ch25h+/+ and ch25h-/- mice and passaged for 2 weeks. The cells were infected VSV-GFP (0.1 MOI) and viral titers 14 hpi in the supernatants was quantified by plaque assay. *P<0.01.
Figure 2:
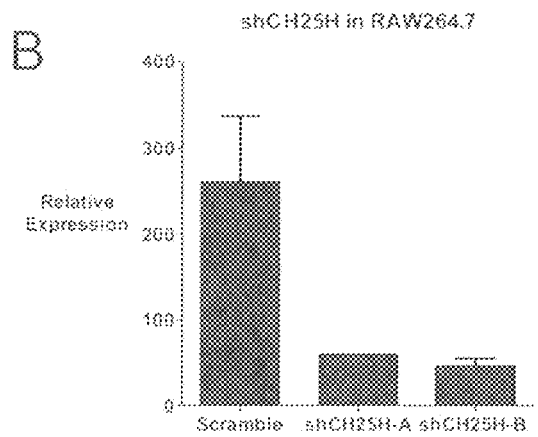

To validate the antiviral effect of Ch25h, we generated a doxycycline-inducible Ch25h-flag construct co-expressing a flourescent-red mCherry (Ch25h-mCherry). Doxycycline addition to HEK293T expressing this construct increased CH25H-flag expression (FIG. 2A top) and mCherry expression in a dose-dependent manner (FIG. 2A, bottom). When infected with VSV-GFP, HEK293T expressing Ch25h-mCherry and treated with doxycycline exhibited a dose-dependent inhibition of VSV-GFP compared to vector control (FIG. 2A, bottom). Taken together, Ch25h is sufficient to inhibit VSV.

Loss of Function of Ch25h Leads to Susceptibility to Viral Infections In Vitro

We sought to determine whether Ch25h might play a necessary role in the viral infection. We generated Ch25h stable knockdown cell lines in murine macrophage cell line RAW264.7 with two distinct shRNA sequences against Ch25h (FIG. 2B). Both knockdown cell lines demonstrated increased VSV replication compared to scramble control (FIG. 2C). To further validate these results, we derived B-Cells and macrophages from Ch25h-deficient (ch25h−/−)

and matching wild-type (ch25h+/+) mice. In our experience, VSV-GFP could not establish infection in primary cells (unpublished). Hence, B-cells were immortalized with BCR-ABL virus and several stable clones were isolated. We observed about 100 fold increase in VSV-GFP replication in 3 different Ch25h−/− B-Cell clones at 48 hpi compared to 2 ch25h+/+B-cell clones (FIG. 2D). In parallel, we performed VSV infection in BMMs immortalized by J2 virus (FIG. 2E). Similarly, ch25h−/− J2 BMMs displayed 5-fold increased susceptibility to VSV infection compared to ch25h+/+J2 BMMs at 14 hpi. These results show that Ch25h may be required for host antiviral immunity.

Ch25h Produces a Soluble Antiviral Factor that is not IFN

Figure 3:
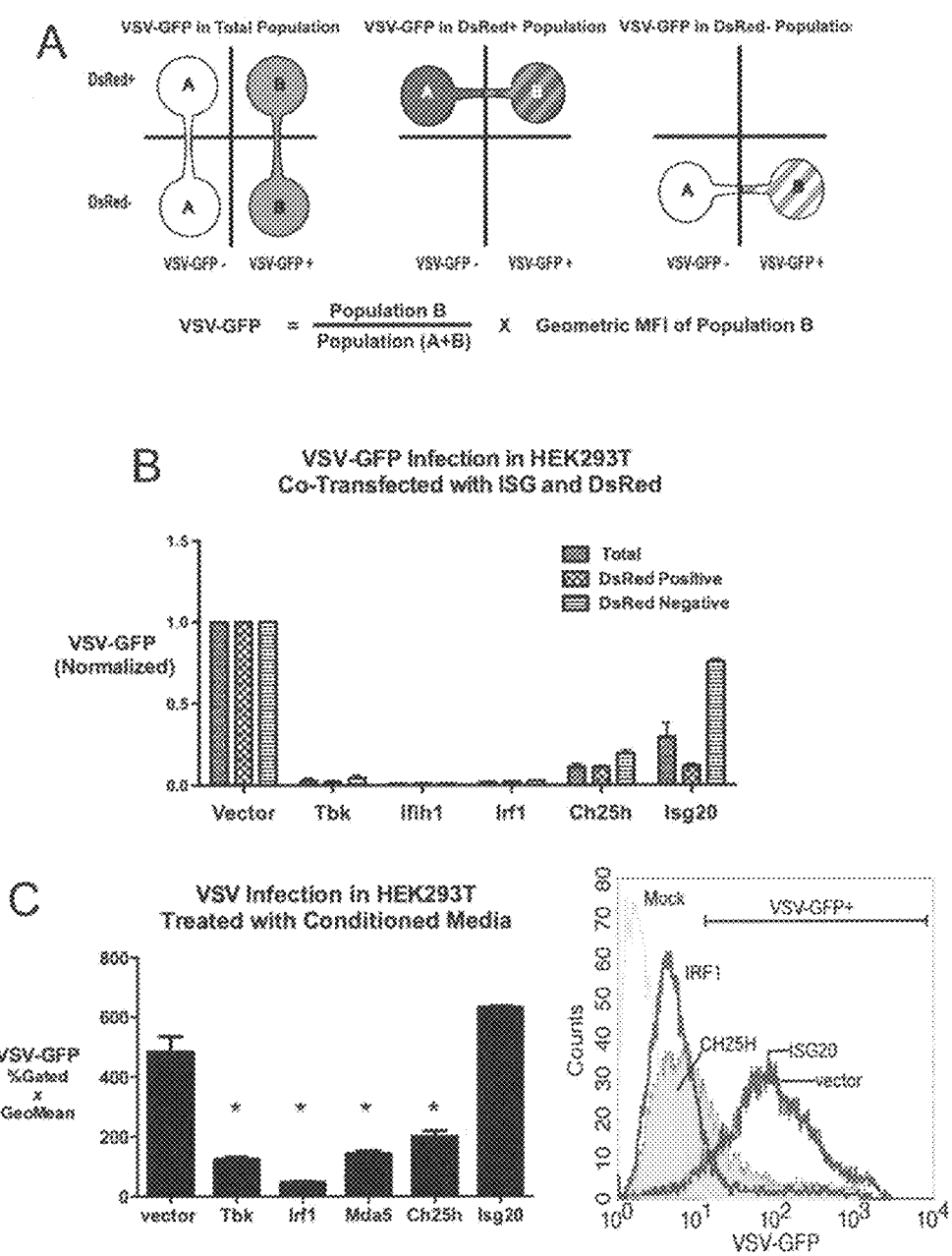
FIG. 3. (A) Schematic of FACs analysis of VSV-GFP in total, DsRed-VSV-GFP was defined as % positive GFP X geometric MFI. DsRed-positive (DsRed+) and DsRed-negative (DsRed−) populations. (B) HEK293T transfected with DsRed and indicated expression vectors were infected with VSV-GFP and analyzed by FACs (% positive GFP X geometric MFI). (C) Media was collected from HEK293T after 48 h transfection with indicated expression vector. Freshly plated HEK293T was treated with conditioned media for 8 h and infected with VSV-GFP (0.01 MOI) for 9 h. VSV-GFP was quantified by FACs (% positive GFP X geometric MFI). Representative histogram of FACs data (right). *P<0.01. (D) Ifnar−/− tail derived fibroblasts were treated with conditioned media for 12 h from HEK293T transfected with indicated expression vector. The fibroblasts were infected with VSV-GFP (0.1 MOI) and the viral titer in the supernatant was measured by plaque assay. *P<0.05. (E) Ifnar−/− derived J2 BMMs fibroblasts were treated with conditioned media for 12 h from HEK293T transfected with indicated expression vector. The cells were infected with VSV-GFP (0.1 MOI) and the viral titer in the supernatant was measured by plaque assay. *P<0.05.

Based on the FACs analyses of HEK293T transfected with ISGs in FIG. 1D, we separated our analyses to examine total, DsRed-positive (DsRed+), and DsRed-negative (DsRed−) populations (FIG. 3A). DsRed+ population should represent cells that highly expressed the ISG, whereas DsRed-population should represent the low expressing population. IFN activators such as Tbk1, Irf1, and Ifih1 inhibited VSV-GFP expression by >95% in all populations suggesting that the high expressers (DsRed+) confer viral resistance to low expressers (DsRed−) (FIG. 3B). This result is consistent with IFN-mediated induction of an antiviral response in naïve cells. In contrast, the cytoplasmic exonuclease ISG20 that degrades viral RNA, only inhibited VSV in DsRed+ population, but could not confer protection to DsRed− population. Overexpression of Ch25h also inhibited virus in both DsRed+ and DsRed− populations suggesting that Ch25h produced a soluble factor that could confer, in trans, antiviral activity onto other cells.

Figure 8:
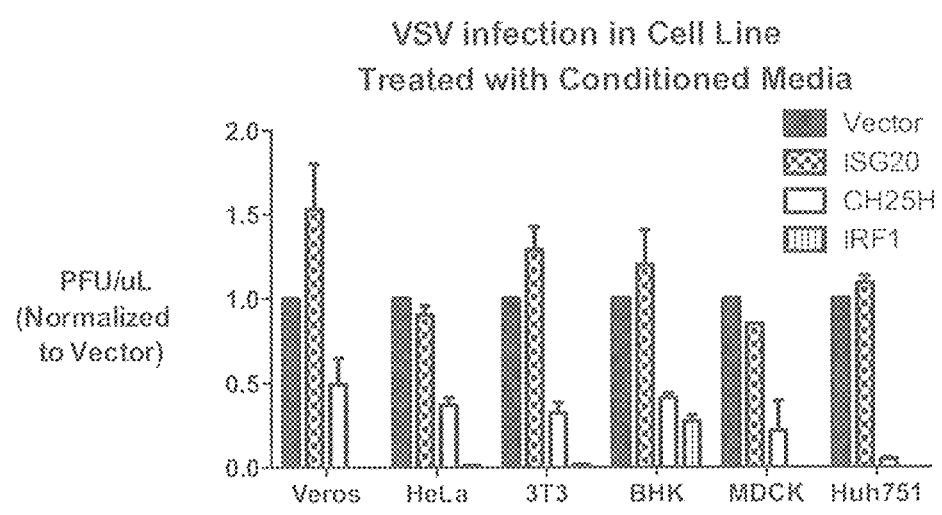
FIG. 8. Indicated cell lines were treated for 8-12 h with conditioned media from HEK293T transfected with indicated expression vectors. They were infected with VSV at 0.01 MOI for 9-14 h, depending on the cell line. VSV-GFP was quantified by FACs (% GFP+ X Geometric MFI) and normalized to VSV-GFP in cell treated with vector-conditioned media.

To determine if Ch25h produced a soluble antiviral factor, we tested whether conditioned media from cells overexpressing Ch25h had antiviral activity. HEK293T cells were transfected with vector, interferon activators (Tbk11, Irf1, and Ifih1) or ISGs, for 48 hours and the conditioned media was filtered and transferred onto freshly plated HEK293T cells for 8 h before infection with VSV-GFP (0.01 MOI) for 9 h. VSV-GFP measured by FACs was significantly less in cells treated with conditioned media from Tbk1, Irf1, Ifih1, because they contain IFN. Compared to vector controls, Ch25h-conditioned media caused ~80% VSV-GFP inhibition (FIG. 3C). On the other hand, conditioned-media from Isg20-transfected cells had no effect on VSV replication. Furthermore, we have observed inhibition of VSV growth by Ch25h conditioned media across several human and murine cell lines including HeLa, 3T3, BHK, Veros, MDCK, and Huh751 (FIG. 8). These results demonstrate that Ch25h produces a soluble antiviral factor.

Figure 9:
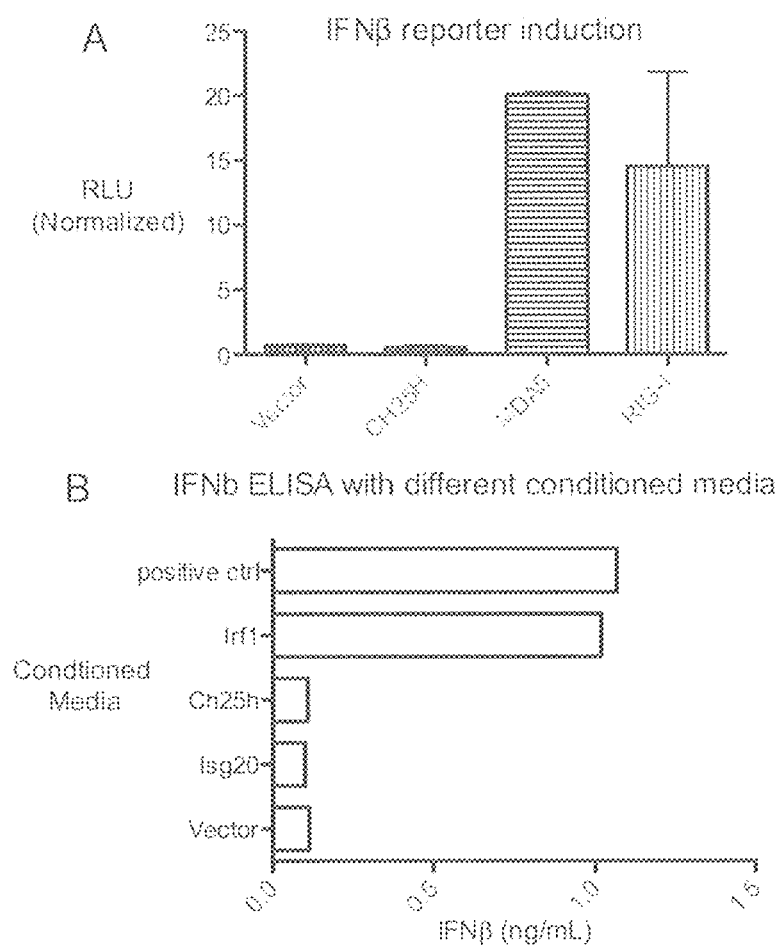
FIG. 9. (A) HEK293T was transfected with indicated expression vector and IFNβ-luciferase reporter. Luciferase activity was measured after 16 h. RLU-relative light units. (B) IFNβ ELISA of conditioned media from HEK293T transfected with indicated expression vectors after 24 h.

IFN is well known to induce many ISGs that positively feedback and amplify IFN itself. Since there have been no soluble antiviral ISGs described aside from IFN, we tested whether Ch25h can induce IFN. Ch25h conditioned media had no detectable IFNβ by ELISA and did not induce an IFN-stimulated responsive element (ISRE) luciferase reporter (FIGS. 9A and 9B). More importantly, Ch25h-conditioned media inhibited VSV replication in both ifnar−/− fibroblasts and J2 BMMs. On the other hand, conditioned media from IFN activators, Irf1, Ifih1, and Rig-1, were unable to confer antiviral activity to ifnar−/− cell lines (FIGS. 3E and 3F). Taken together, Ch25h produces a soluble factor that is not IFN and can confer antiviral activity independent of IFNAR.

25-Hydroxycholesterol, the Cognate Product of Ch25h, has Antiviral Activity

Figure 4:
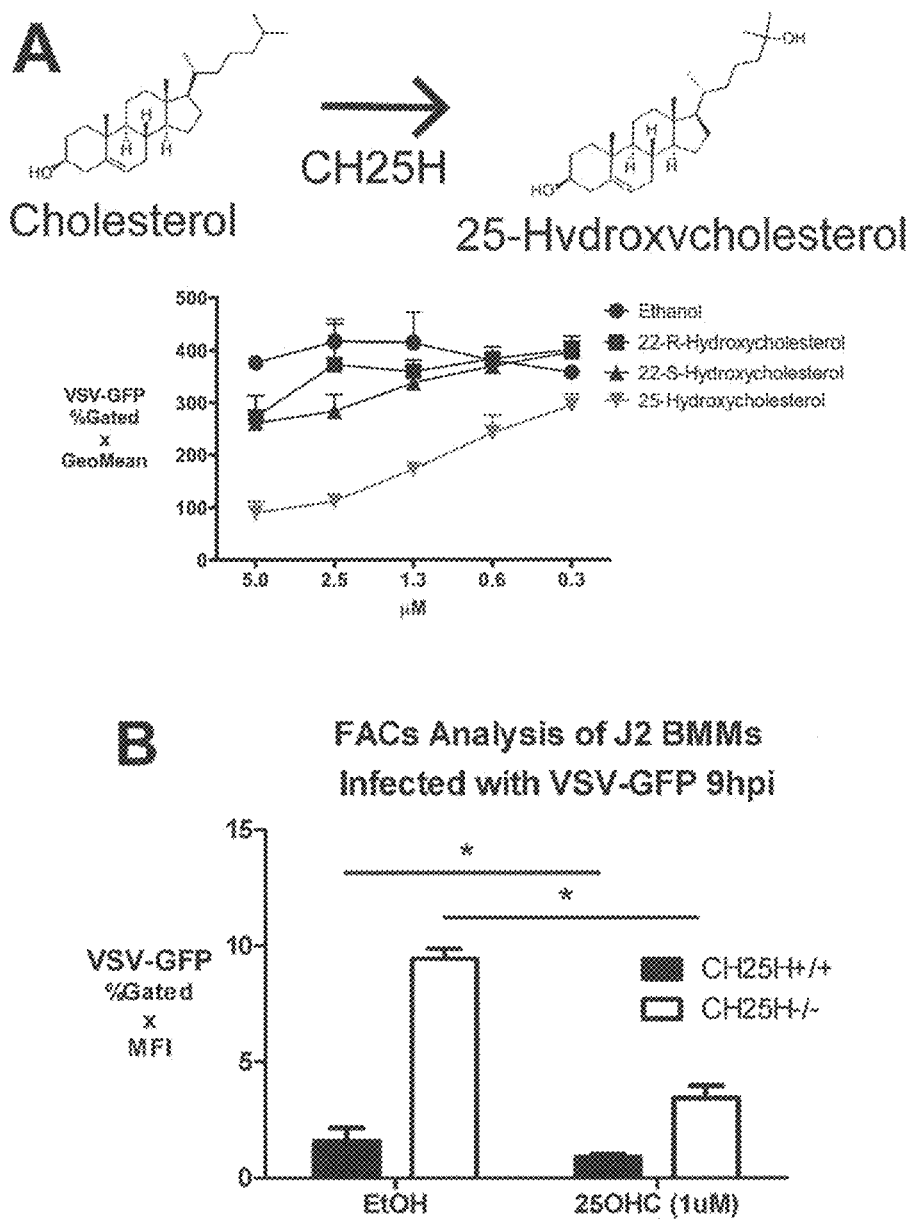
FIG. 4. (A) CH25H converts cholesterol to 25-hydroxycholesterol (25HC, top). HEK293T was treated with 22(S)-HC, 22(R)-HC, 25HC, and the vehicle, ethanol (EtOH) for 8 h at the indicated concentrations and infected with VSV-GFP. VSV-GFP was quantified by FACs (% GFP+X Geometric MFI). (B) Ch25h+/+ and Ch25h−/− J2 BMMs were treated with 25HC (1 µM) or EtOH and infected with VSV-GFP (0.01 MOI). VSV-GFP was quantified by FACs at 12 hpi. Mean±SD; *P<0.02. (C) Costimulated PBMC were pre-incubated for 24 h in conditioned media before infection with HIV NL4-3. At 3 dpi, p24 in triplicate samples were quantified by ELISA. Mean±SEM; *P<0.001. (D) Costimulated PBMC (1×10$^6$) were pre-incubated for 24 h in 22(S)-HC (1 µM), 25HC (1 µM), and vehicle (EtOH) containing media before infection with HIV NL4-3 in triplicates (30 ng of HIV strain NL4-3). At 3 dpi, p24 was quantified by ELISA. Mean±SEM; *P<0.001. (E) HEK293T was treated with indicated conditioned media for 12 h and infected with HSV (0.25 MOI) for 24 h. HSV titer in the supernatant was quantified by plaque assay. Mean±SEM; *P<0.001. (F) HEK293T were transfected with indicated expression plasmids and infected with MHV68 (0.2 MOI) for 24 h. MHV68 titer in the supernatant was quantified by plaque assay. Mean±SEM; *P<0.001. (G) HeLa cells were pretreated with 25HC (1 µM) or EtOH containing media for 5 h and infected with Ebola Zaire-GFP (EBOV) at 0.1 MOI. At the indicated times, combined supernatants from biological triplicates was measured by plaque assay. (H) HeLa cells were pretreated with media containing indicated concentrations of 25HC or EtOH for 12 h and infected with Nipah virus (Bangladesh strain) at 0.1 MOI. At the indicated times, combined supernatants from biological triplicates was measured by plaque assay. (I) HeLa cells were pretreated with media containing indicated concentrations of 25HC or EtOH for 12 h and infected with Russian Spring-Summer Encephalitis Virus (RSSEV) at 0.1 MOI. At the indicated times, combined supernatants from biological triplicates was measured by plaque assay. (J) HeLa cells were pretreated with media containing indicated concentrations of 25HC or EtOH for 12 h and infected with Rift Valley Fever Virus ZH501 (RVFV) at 0.1 MOI. Viral titer at indicated time points was measured by plaque assay. Values represent means of samples from triplicates. (K) HEK293T were treated with EtOH, 22S-HC, and 25HC for 12 h and infected with adenovirus-GFP and VSV-GFP and quantified by FACs (% GFP+X Geometric MFI). Mean±SEM; *P<0.001.

Ch25h catalyzes oxidation of cholesterol to 25-hydroxycholesterol (25HC), which is a soluble oxysterol that modulate cellular functions in an autocrine and paracrine fashion (FIG. 4A, top). We hypothesized that the soluble antiviral factor generated by Ch25h is 25-hydroxycholesterol. Treatment of HEK293T cells with 25HC for 8 h inhibited VSV-GFP expression by FACs in a dose-dependent manner with $IC_{50}$ of ~1 uM (FIG. 4A, bottom). Some studies have shown 25HC as a weak ligand for LXR suggesting this nuclear receptor might play a role in the antiviral activity of 25HC (Janowski et al., 1999). Treatment of HEK293 Ts with 22-(R)-hydroxycholesterol (22R-HC), an oxysterol that strongly activates LXR, however, did not confer antiviral effect and neither did 22-(S)-hydroxycholesterol (22S-HC), an inactive ligand for LXR (FIG. 4. A, bottom). 25HC treatment of ch25h+/+ and ch25h−/− J2 BMMs also reduced VSV replication (FIG. 4B).

Figure 10:
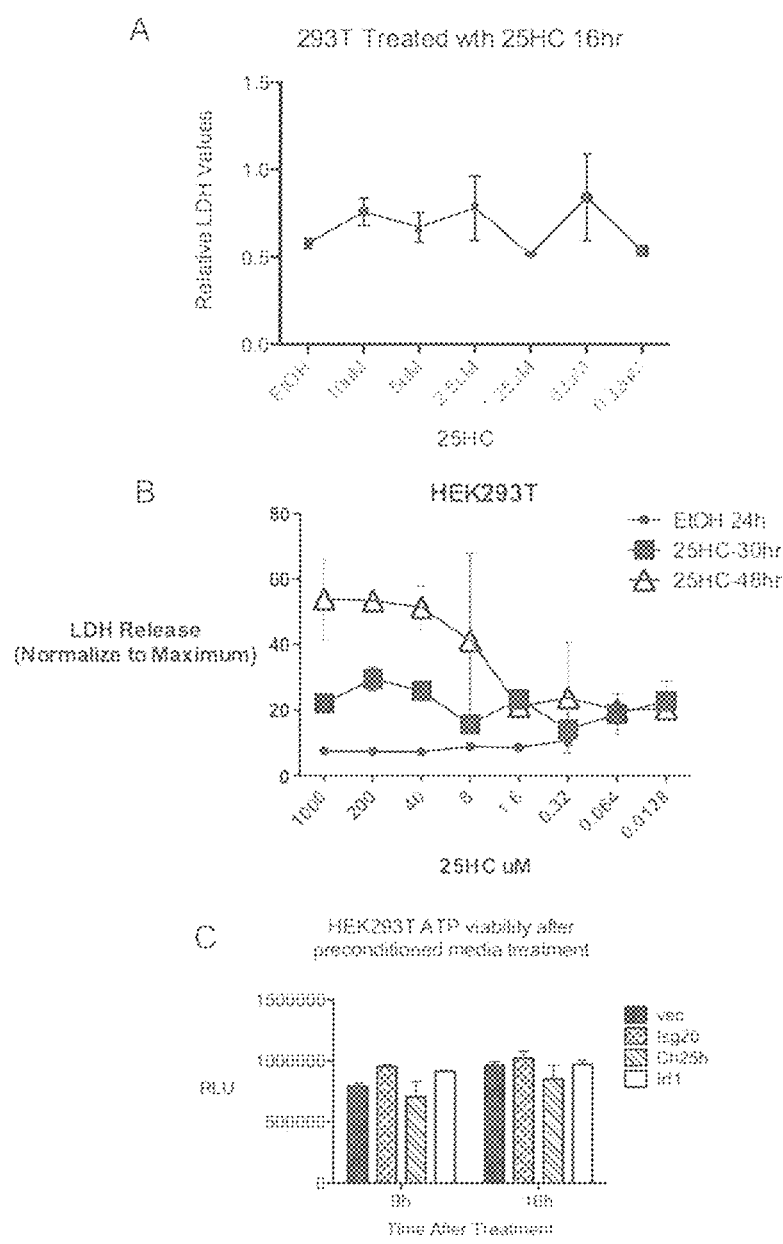
FIG. 10. (A) HEK293T were treated with increasing amount of 25HC and LDH values was measured after 16 h. (B) HEK293T were treated with increasing amount of 25HC and LDH was measured after 30 and 48 h. (C) Measurement of HEK293T ATP viability after preconditioned media treatment and various times after treatment, FIG. 11. (A) HeLa cells were pretreated with media containing indicated concentrations of 25HC or EtOH for 12 h and infected with RVFV (MP12 vaccine strain) at 0.1 MOI. Viral titer at indicated time points was measured by plaque assay. Values represent means of samples from triplicates. (B) HeLa cells were pretreated with media containing indicated concentrations of 25HC or EtOH for 12 h and infected with Nipah virus (Bangladesh strain) at 0.1 MOI. Viral titer at indicated time points was measured by plaque assay. Values represent means of samples from triplicates.

We tested whether the antiviral activity of 25HC was attributed to cellular cytotoxicity. Increasing doses up to 10 uM-10 fold higher than observed $IC_{50}$—of 25HC did not increase LDH in supernatants of cells after 16 h of treatment; LDH level increased only after 30-40 h treatment at 40 uM of 25HC (FIGS. 10A and 10B). Similarly, Ch25h-conditioned media did not alter cell viability as measured by cellular ATP levels (Supp. FIG. 10C). These data show that Ch25h-conditioned media and the effective antiviral dose of 25HC are not cytotoxic. Therefore, these results suggest that the antiviral activity of Ch25h is carried out through its enzymatic product, 25HC. Its antiviral activity is not attributed to LXR function per se and—compared to the oxysterols tested—is specific.

Ch25h-Conditioned Media and 25HC is Broadly Antiviral

To determine the breadth of antiviral activity of Ch25h, we tested the effect of Ch25h-conditioned media and 25HC on various viruses. For HIV, primary peripheral blood mononuclear cells were treated with conditioned media or oxysterol and subsequently infected with HIV NL4-3. At 3 dpi, Ch25h- and Irf1-conditioned media caused ~75% reduction of HIV NL4-3 p24 expression (FIG. 4C). Similarly, 25HC (1 μM) inhibited p24 expression by ~80% at 3 dpi compared to vehicle treatment, whereas 22S-HC had no effect (FIG. 4D). Ch25h-conditioned media also inhibited herpes simplex virus 1 (HSV-1) by plaque assay (FIG. 4E) and expression of Ch25h in HEK293T also inhibited MHV68 infection by plaque assay (FIG. 4F).

Figure 11:
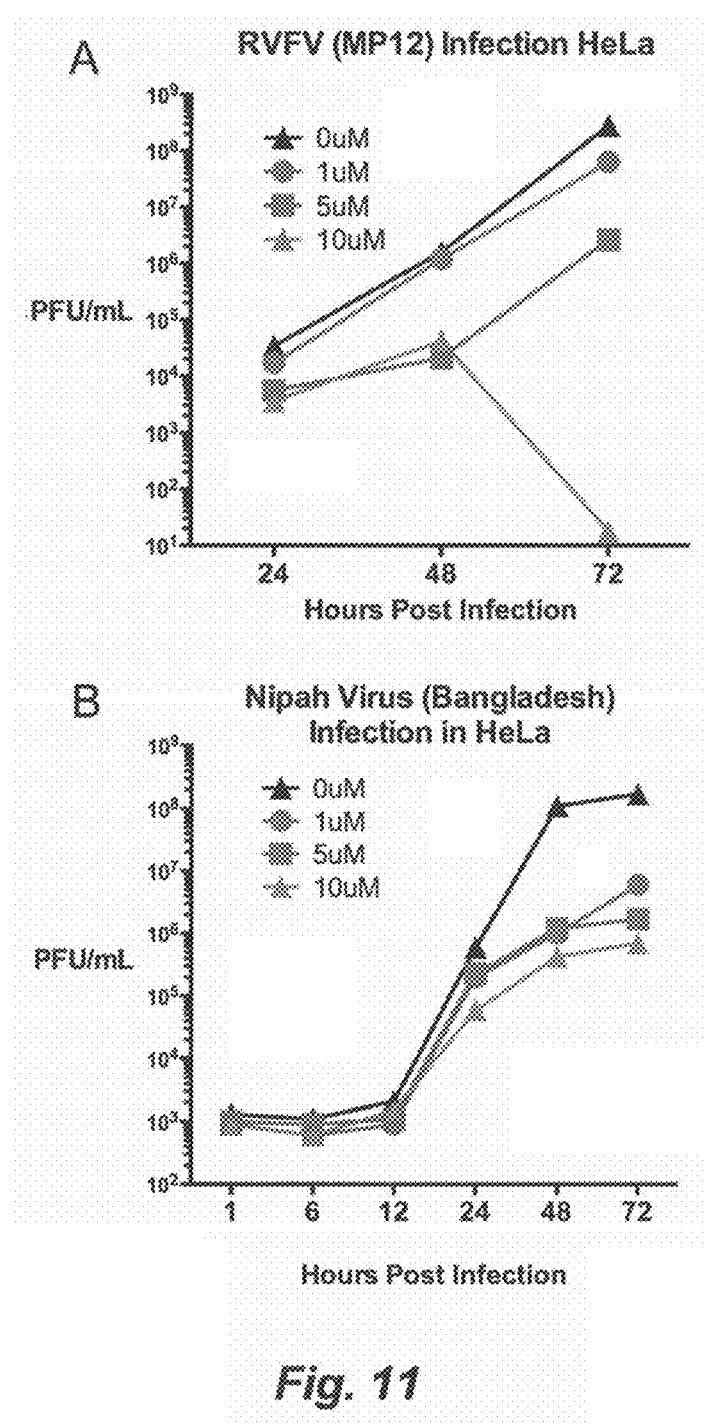

HIV, HSV-1, and MHV68 are viruses that achieve chronically persistent infections. To determine whether Ch25h-induced 25HC can inhibit acutely pathogenic viruses, we tested the effect of 25HC on live Ebola (EBOV-Zaire), Nipah (Bangladesh), Russian Spring-Summer Encephalitis Virus (RSSEV), and Rift Valley Fever Virus RVFV (wild-type strain ZH501 and vaccine strain MP12) under BSL4 conditions. FIGS. 4G, 4H, 4I, and 4J show that 1 uM of 25HC inhibited replication of these live viruses. 25HC also inhibited replication of Nipah and RVFV (MP12) in a dose-dependent manner (FIGS. 11A and 11B). In contrast, a non-enveloped virus, adenovirus coexpressing GFP, was not affected by 25HC as measured by FACS (FIG. 4K). Taken together, Ch25h-induced 25HC has antiviral activity against several types of enveloped DNA and RNA viruses, while they do not have effect on non-enveloped virus.

25HC Inhibits VSV Entry

Figure 5:
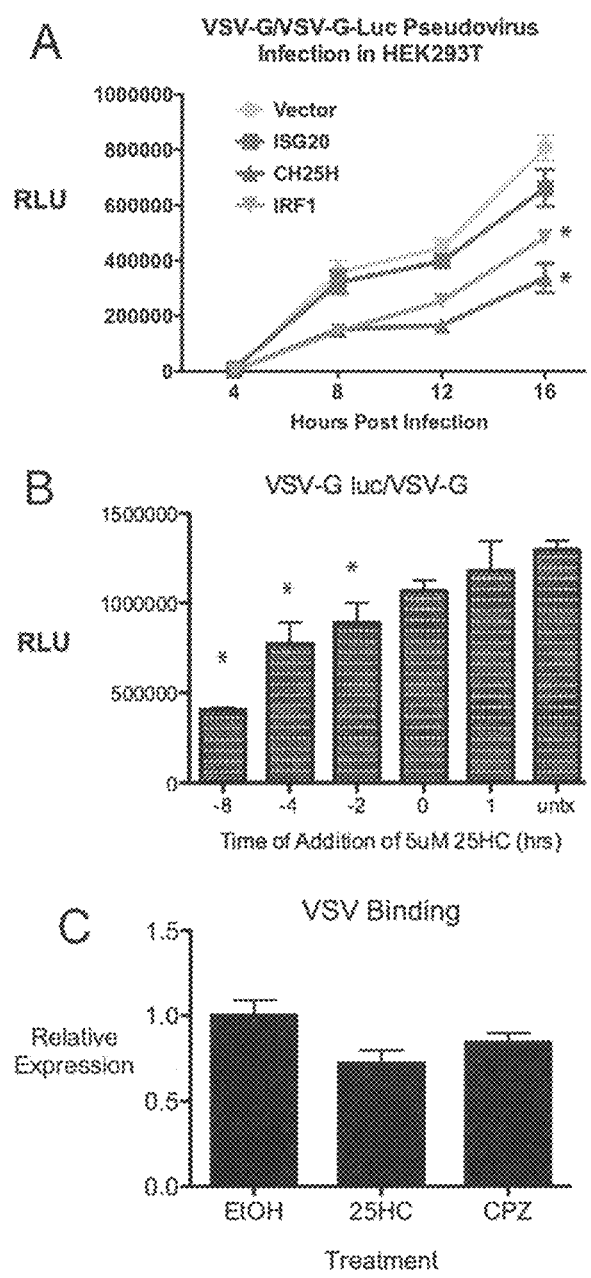
FIG. 5. (A) HEK293 Ts were treated with conditioned media for 12 h and infected with VSV-G pseudovirus encoding VSVΔG-Luciferase (VSVΔG-Luc/G). The cell lysates were collected at indicated times and measured for luciferase activity. (B) HEK293T were treated with 25HC (5 µM) at different times relative to the VSVΔG-Luc/G infection. For time 0, VSVΔG-Luc/G was added together to the cells for 1 h. Negative numbers indicates addition of 25HC before infection, while positive number indicates addition after infection. Relative Light Units (RLU) is represented as Mean±SD *P<0.01. (C) HEK293T were treated with respective agonists for 8 h in triplicates. VSV infection on HEK293 Ts was synchronize at 4 C, washed 3 times with PBS, and shifted to 37 C for 30 min. VSV genomic RNA was quantified by qRT-PCR Mean±SEM; *P<0.05. (D) HEK293T were treated with respective agonists for 8 h in triplicates. VSV infection on HEK293 Ts was synchronize at 4 C and washed 3 times with PBS. VSV genomic RNA was quantified by qRT-PCR. (E) HEK293T was transfected with indicated expression plasmids for 24 h and infected with pseudovirus with encoding NipahM-beta-lactamase inside VSV-G (VSV-G/BlaM) for 1.5 h. β-lactamase activity was measured by the cleavage of CCF2-AM dye. Response ratio is the ratio of the cleaved form (blue 485 nm) to uncleaved (green, 525 nm) CCF2-AM. *P<0.01, **P<0.001. (F) HEK293T was treated with indicated conditioned media for 12 h and infected with VSV-G/BlaM. β-lactamase activity was measured by CCF2-AM response ratio. *P<0.01, **P<0.001. HEK293T was treated with indicated concentration of 22(S)-HC, 25HC, and equivalent volume of vehicle (EtOH) for 12 h and infected with VSV-G/BLaM. β-lactamase activity was measured by CCF2-AM response ratio. *P<0.01, **P<0.001.

We took advantage of tools available for VSV and HIV to study the mechanism of Ch25h inhibition on the viral lifecycle. First, we utilized the pseudotyped VSVΔG-Luc reporter virus system that has the receptor-binding G gene (VSV-G) replaced with a luciferase reporter gene (Negrete et al., 2006). When VSV-G is provided in trans, this pseudotyped VSV reporter virus is only capable of single-round infections because it cannot produce its own VSV-G. Hence, quantification of luciferase activity is indicative of viral lifecycle processes from entry to protein synthesis. We observed that Ch25h and Irf1 conditioned media inhibited virus reporter gene expression at the earliest time-point (8 hpi) we can detect luciferase activity in the infected cell lysate (FIG. 5A), suggesting Ch25h inhibits viral replication at an early stage.

Next, we performed a time-of-addition experiment to better elucidate the mechanism underlying the antiviral activity of 25-HC. HEK293T cells were treated or pretreated with 5 μM 25HC at the indicated time points. For pretreated cells, they were infected with VSVΔG-Luc pseudovirus for 1 h without 25HC; after washing, cells were replaced with regular media. We also added 25HC concurrently with infection (time 0) for 1 h or added it at 1 hpi. Interestingly, longer pre-treatment times correlated with greater inhibition of VSVΔG-Luc expression, compared to the ethanol vehicle treated controls. When 25HC was added concurrently with VSVΔG-Luc pseudovirus or 1 hpi, VSV-G mediated infection was not significantly inhibited (FIG. 5B). These results suggest that 25HC does not inhibit VSV during infection or after infection has taken place. Rather, it is likely that 25HC establishes an antiviral state prior to infection.

Since these data implicate early viral lifecycle steps may be affected, we carried out experiments to determine whether 25HC affects binding (Weidner et al., 2010). HEK293 Ts were treated for 8 h with ethanol (EtOH), 25HC (1 μM), CPZ (10 ug/mL), an endocytosis inhibitor that would have no effect on binding. To measure binding, VSV (1 MOI) was incubated with HEK293T at 4° C. for 1 h to allow for binding but not cell entry. After washing 3 times with cold PBS, total RNA was collected and VSV genomic RNA (gRNA) was reverse-transcribed with gRNA specific primer. 25HC and CPZ did not inhibit binding significantly (P>0.05) (FIG. 5C).

To determine if 25HC affects efficiency of fusion, we established a VSV-G β-lactamase (Bla) entry assay based on the ability of VSV-G to be pseudotyped onto viral-like particles made from the Bla-Nipah virus matrix fusion protein, herein called VSV-G/BlaM (Wolf et al., 2009). VSV-G mediated fusion will result in cytoplasmic delivery of Bla-M; by addition of lipophilic fluorescent CCF2-AM substrate, the β-lactamase activity can be measured by the green (525 nm) to blue (485 nm) fluorescence shift as a result of CCF2-AM cleavage (Zlokarnik et al., 1998). Hence, efficiency of virus-cell fusion can be measured by the increase in the ratio of blue to green (blue:green) fluorescence, which is reflective of the β-lactamase activity associated with BlaM that was been released into the cytoplasm after VSV-G mediated fusion (Cavrois et al., 2002; Wolf et al., 2009). Unlike the VSVΔG-Luc pseudotyped virus, this VSV-G/BlaM entry assay does not require transcription and translation of viral proteins for reporter gene expression.

HEK293T cells were transfected with several ISGs for 48 hours and infected with VSV-G/BlaM. FIG. 5D showed that Ch25h and Irf1 reduced efficiency of VSV fusion. Compared to vector control, BlaM activity from Ch25h- and Irf1-transfected cells proceeded at a slower rate compared to vector-transfected cells (compare the respective slopes for the first 45 min) and plateaued at a lower level (compare blue:green ratio at 120 min). To a lesser extent, Ifitm3 also reduced VSV-G/BlaM entry, consistent with published results that showed it inhibits VSV-pseudovirus infection (Brass et al., 2009). ISG20, a viral RNA exonuclease, had no effect on viral entry. Ch25h-conditioned media similarly inhibited VSV-G/B laM entry, but with a more pronounced effect than Irf1-conditioned-media (FIG. 5E). Finally, we also observed a dose-dependent inhibition on VSV-G/BlaM entry with treatment of 25HC at 1, 2.5, and 5 μM (FIG. 5F). These results demonstrate that the ISG, Ch25h, and its cognate product, 25HC, modulates the target cell membrane in a manner that inhibits efficiency of virus-cell fusion.

Figure 12:
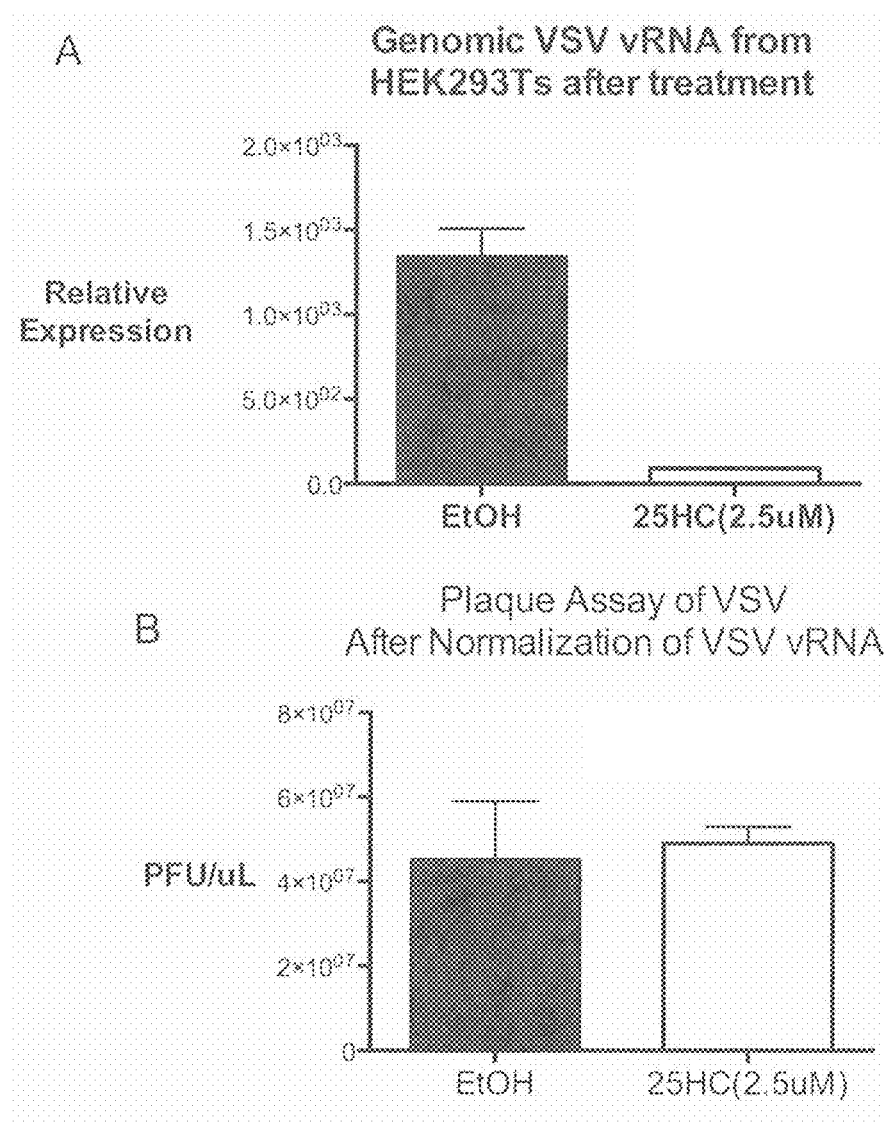
FIG. 12. (A) HEK293T were treated with 25HC (2.5 uM) and vehicle (EtOH) for 8 h and infected with VSV-GFP at 0.01 MOI. The cells were treated against with 25HC after infection. Supernatants were collected 24 hpi and virus was concentrated by centrifugation. For a part of the concentrated virus, VSV genomic RNA (gRNA) was quantified by qRT-PCR. (B) Concentrated virus from part A was normalized based on VSV gRNA and standard plaque assay was performed.

Since viral entry involves interactions between both the viral and cellular membranes, we then asked if the infectivity of the virions are affected when produced from 25HC treated cells. HEK293T were treated with and without 25HC (2.5 uM) for 8 h and infected with replication-competent VSV at 0.01 MOI. After a 1 h infection period, the cells were washed and replaced with media containing 25HC (2.5 uM). The viral supernatants from infected cells were collected at 24 hpi, purified, and concentrated by ultracentrifugation through a 20% sucrose cushion, which also removed any residual 25HC. As expected, 25HC treatment caused >80% reduction in the amount of VSV produced compared to vehicle-treated controls as measured by qRT-PCR for the number of viral genome copies (FIG. 12A). To assess infectivity, we measured the infectious titer of viruses produced from 25HC- or vehicle-treated cells after normalizing for the amount of viral gRNA as determined above. When the titer was quantified on Vero cells, viruses from 25HC treated cells had equivalent plaque forming units as viruses from vehicle-treated cells (Supp. FIG. 11B), demonstrating that while 25HC exerts its antiviral effect by altering target cell membrane properties, this effect is not manifested in virions produced from those cells.

Figure 13:
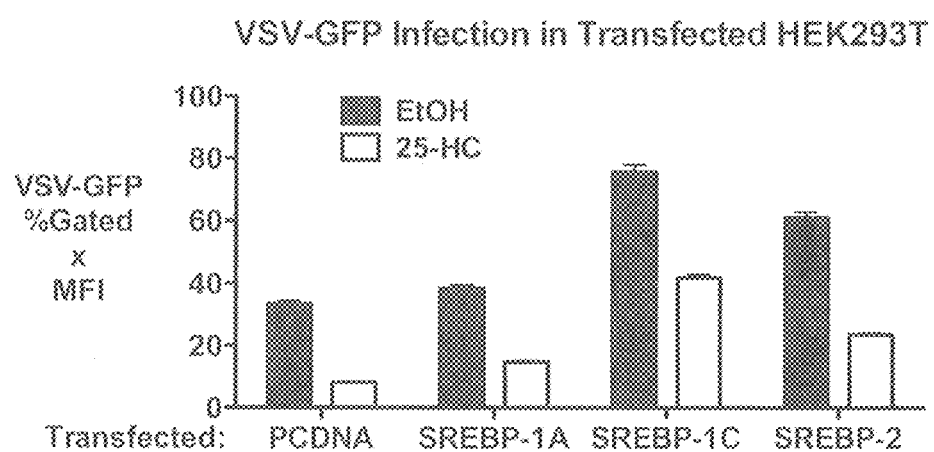
FIG. 13. (A) HEK293T were transfected with mature form of SREBP1a, SREBP1c, and SREBP2 for 24 and treated with 25HC for 12 h. The cells were infected with VSV-GFP (0.01 MOI) and quantified by FACs.

25-hydroxycholesterol is a suppressor of SREBP2, which controls sterol biosynthesis and can alter membrane sterol composition. Hence, we tested the hypothesis that 25HC inhibits viral infection through suppression of SREBP2. We tested whether overexpression of active (cleaved) form of SREBPs in HEK293T would overcome the anti-viral effect of 25HC. 25HC inhibited VSV infection in HEK293T overexpressing active forms of SREBP1-A, SREBP1-B, and SREBP2 (FIG. 13). These data demonstrate that the antiviral effect of 25HC is SREBP independent.

Ch25h and 25HC Inhibits HIV Entry

We sought to validate Ch25h and 25HC antiviral mechanism on HIV. Unlike VSV, HIV is a retrovirus that undergoes pH-independent cellular entry. In CEM cells, 25HC inhibited >50% luciferase expression from single round infection of pseudovirus with HIV-IIIB envelope on a NL4-3 backbone coexpressing luciferase (pNL4-3.Luc.-R-E) (FIG. 6A). AZT, an inhibitor of reverse transcription, served as positive control and inhibited expression by ~70%. Hence, these data also suggest 25HC inhibits viral lifecycle prior to translation.

HIV initiates reverse transcription of its genomic RNA to DNA immediately after entry. Hence, we examined the effect of 25HC on the production of full-length, reverse-transcribed DNA (lateRT). CEM cells were infected with pseudotyped HIV-IIIB and lateRT was measured by qRT-PCR. 25HC inhibited lateRT expression >99% at 2 hpi and ~70% at 6 hpi (FIG. 6B). The HIV entry inhibitor, AMD3100, served as positive control. Elvitegravir inhibits HIV at the step DNA integration into the host genome and served as negative control because it shouldn't inhibit lateRT formation. These results show that 25HC inhibits a stage of HIV before reverse transcription of its genome.

Figure 14:
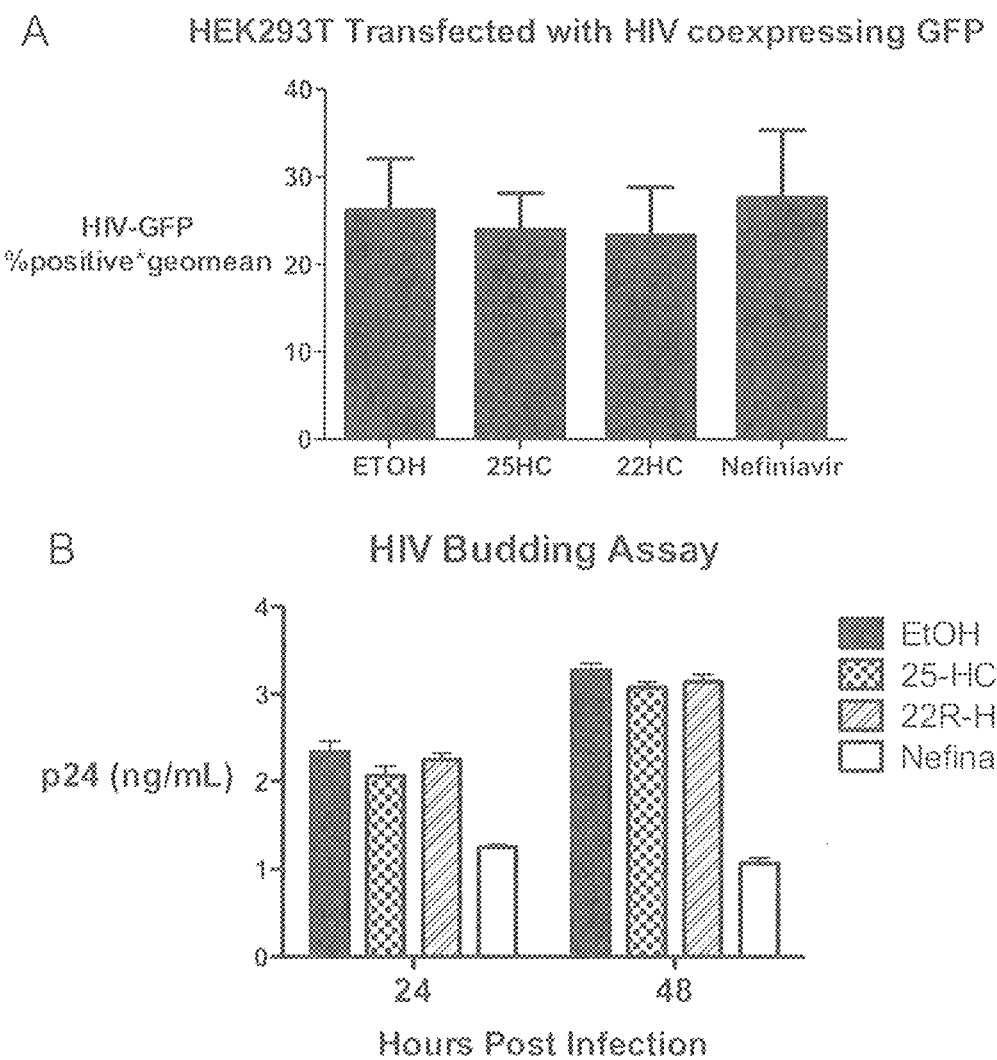
FIG. 14. (A) CEM cells were treated with indicated conditioned media for 8 h and infected with HIV NL4-3 encoding Vpr-BlaM (NL4-3/BlaM) in duplicates. AMD3100 serve as positive control for entry inhibition. CCF2-AM cleavage was confirmed by FACs. Numbers represent percentage cells expressing cleaved form of CCF2AM (485 nm). (B) HEK293T were transfected with proviral plasmid of HIV coexpressing GFP and treated with indicated agonists 6 h after transfection. HIV-GFP was quantified by FACs after 48 h. Viral supernatants from part A was collected after 48 h and p24 was quantified by ELISA.

We next asked whether Ch25h inhibits HIV similar to VSV at the level of entry. We coexpressed pNL4-3 with Bla-VPR fusion gene to produced virions containing Bla-VPR (NL4-3/Bla). CEM cells treated with Ch25h conditioned media exhibited ~60% reduction in viral entry compared to vector- and Isg20-conditioned media. AMD3100 abrogated NL4-3/Bla entry (FIG. 6C). We further confirmed our findings by FACS analysis and observed ~50% decrease in the number of cells expressing cleaved CCF2-AM substrate (blue population) in CEM treated with Ch25h conditioned media compared to control (FIG. 14A). Treatment of CEM cells with 25HC (5 μM) caused ~60% decrease in NL4-3/Bla blue-green ratio at endpoint (FIG. 6D) and >85% reduction in cells expressing cleaved CCF2-AM by FACS analysis (FIG. 6E).

Since 25HC may have diverse cellular effects, we asked whether 25HC might affect other HIV life cycle processes such as transcription, translation, or budding. To assess whether transcription of HIV is inhibited, we transfected HEK293 Ts with pNL4-3 co-expressing GFP (NL4-3-GFP). Addition of 25HC 4 h post transfection did not suppress GFP expression after 24 h suggesting that 25HC does not affect HIV transcriptional and translational processes (Supp. FIG. 14B). Concurrently, we measured the HIV p24 in the supernatants from HEK293T transfected with NL4-3-GFP to assess the amount of viral budding. Compared with ethanol treated controls, 25HC did not affect HIV p24 expression in the supernatants of transfected cells, whereas Nelfinavir, a known budding inhibitor, inhibited p24 expression by >50% at 24 and 48 h post transfection.

Taken together, Ch25h and 25HC inhibits efficiency of HIV membrane fusion, while 25HC treatment does not directly affect HIV transcription, translation, and budding processes.

25HC Inhibits Virus-Cell Membrane Fusion

Although β-lactamase data demonstrate 25HC inhibits viral entry processes up to fusion, we sought to test whether 25HC inhibits the viral fusion process itself. Since we have observed 25HC inhibited live Nipah replication (FIG. 4H), we sought to test whether it would also affect its fusion process. Expression of the Nipah fusion (F) and attachment (G) proteins by themselves induces pH-independent cell membrane fusion and syncytia formation. Hence, vero cells were transfected with recombinant Nipah F and G at equal ratios for 5 h and refreshed with media containing 25HC or ethanol (vehicle). At 21 h post transfection, cells were fixed and stained by Giemsa. Grossly, 25HC treatment led to less syncytia formation and fewer nuclei per syncytial compared to ethanol control (FIG. 6F). In a blinded count of numbers of nuclei per syncytia, a standard measure of fusion, 2 uM of 25HC reduced fusion by ~50% and 10 uM by ~60% relative to ethanol control (FIG. 6G). These data demonstrate that 25HC modifies the cellular membrane to inhibit viral membrane fusion.

25HC Reduces HIV Infection In Vivo

Figure 7:
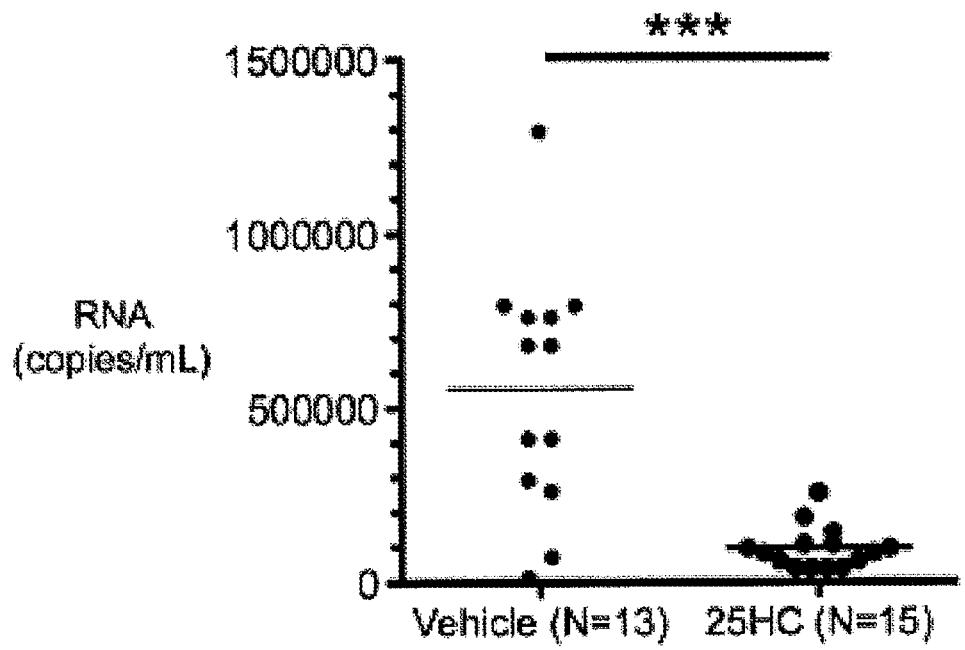
FIG. 7. (A) 25HC (50 mg/kg) or vehicle (2-hydroxypropyl-β-cyclodextrin) was administered 12 h before HIV NL4-3 infection in humanized mice (DKO-hu). Treatment was administered daily after infection. Viral titer in serum was measured by qRT-PCR 7 dpi. Results are combined from 2 experiments. ***P<0.0001. (B) Spleens from DKO-hu mice were harvested 14 dpi and quantified by FACs after HIV p24 intracellular staining. (C) Percent CD4+ T-cells was compared by FACs in 25HC and EtOH treated group. Representative FACs plots are shown (right). (D) ch25h+/+ and ch25h−/− mice were infected with MHV68-Luc (500 pfu) and the amount of infection was quantified everyday by bioluminescence imaging. Average total intensity from ventral, right, left, and dorsal sides were measured for all mice. *P<0.05. (E) Average intensity from ventral, right, left, and dorsal side of each mice were averaged for ch25h+/+ and ch25h−/− mice. *P<0.05. MHV68 genomic DNA from ch25h+/+ and ch25h−/− infected mice 9 dpi was quantified by qRT-PCR and normalized to a genomic promoter of cc12 gene. *P<0.01. (F) Representative bioluminescent images of ch25h+/+ and ch25h−/− mice 9 dpi.
Figure 7:
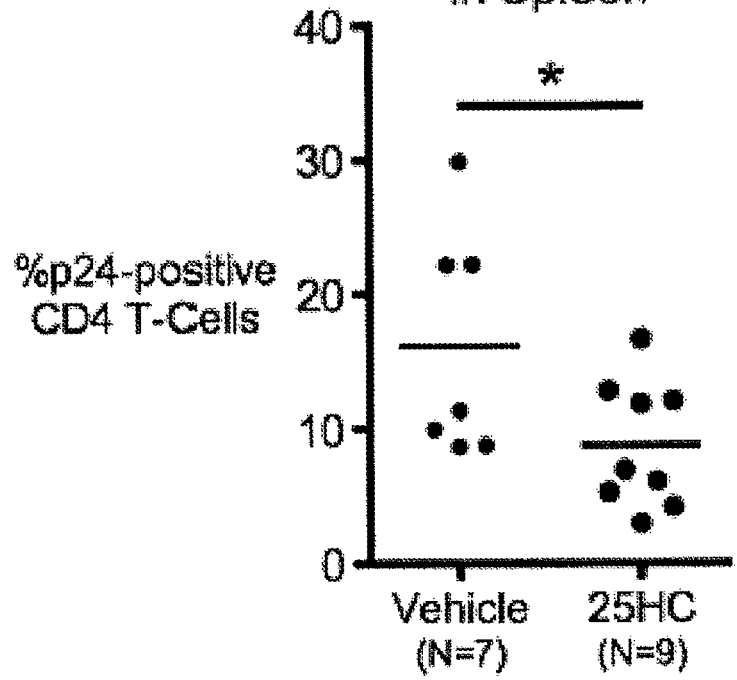

To further determine the efficacy of 25HC against viral infection in vivo, we took advantage of HIV infection in humanized mouse model. Humanized mice were administered 25HC (50 mg/kg) 12 h prior to infection with HIV NL4-R3A by intraperitoneal (i.p) injection. 25HC or the vehicle, 2-hydroxypropyl-β-cyclodextrin (HβCD), was administered by i.p. every day and the serum was collected 7 dpi. Quantification HIV RNA in the serum from 2 combined experiments showed >80% reduction of HIV RNA (copies/mL) in 25HC-treated mice compared to vehicle-treated mice ($P<0.0001$) (FIG. 7A). At termination of the experiment on 14 dpi, HIV p24 was significantly lower in CD4 T-cells from spleens of 25HC treated mice than control (FIG. 7B). In CD3+ T-cell population, which reflects live T-cells, 25HC prevented HIV-mediated CD4 T-cell depletion compared to vehicle control in peripheral blood leukocytes ($P<0.05$); this effect was less significant in the spleen ($P=0.06$) (FIG. 7C). These data show that administration of 25HC can cause antiviral effect against HIV in vivo.

Ch25h-Deficient Mice are More Susceptible to Viral Infections

To determine whether Ch25h has a physiological role in host defense against viral infection, we tested whether ch25h−/− mice had increased susceptibility to matching wild-type mice (ch25h+/+). Since Ch25h expression inhibited MHV68 in vitro, we used MHV68 coexpressing luciferase (MHV68-Luc) to infect mice so that viral lytic growth kinetics could be measured in real time by bioluminescence. Eight-week old female ch25h+/+ and ch25h−/− mice (N=4 in each group) were infected with 500 pfu of MHV68-Luc i.p. and imaged every day after 3 dpi. Average luminescence intensities from ventral, right, left, and dorsal side of every mouse were measured. We observed significantly higher MHV68-Luc activity in ch25h−/− mice over ch25h+/+ mice starting 5 dpi and maximal difference by day 7 (FIG. 7D). MHV68-Luc activity began to wane in both groups by 9 dpi with significantly higher activity in Ch25h−/− mice. To validate the imaging results, Ch25h−/− spleens had approximately ~3.5 fold higher MHV68 genomic DNA than spleens of Ch25h−/− mice at 10 dpi (FIGS. 7E and 7F). These results show that Ch25h is a physiologically important antiviral factor.

Discussion

We have identified the antiviral activity of an IFN-inducible gene, Ch25h, through a systematic, functional screen. Distinct from known IFN-mediated antiviral mechanisms, Ch25h inhibits growth of a wide range of enveloped viruses by production of a soluble oxysterol, 25-hydroxycholesterol. It also exemplifies the only soluble antiviral ISG that is not IFN itself. Independent of its known regulatory effect on metabolism, 25HC impairs viral entry at the step virus-cell fusion by inducing cellular membrane changes. In animal models, administration of 25HC reduces HIV infection in humanized mice. Moreover, immune response against viral infections requires Ch25h in vivo. These findings illustrate an essential function of Ch25h in immunity.

Ifitm proteins are the only ISGs that have been described to inhibit viral entry, after endocytosis and before primary transcription (Brass et al., 2009; Weidner et al., 2010). The transmembrane protein inhibits only certain viruses, suggesting it has specific protein interactions with viral components. In contrast, 25HC is broadly inhibitory against enveloped viruses because it modifies host cellular membrane and perturbs the fusion process with virus. Moreover, in our β-lactamase assays, overexpression of Ch25h inhibited VSV entry >2-fold higher than Ifitm3 (FIG. 5D). Taken together, IFN induces these two ISGs to block viral entry likely by disparate mechanisms.

Oxysterols have multi-faceted physiological roles. Their permeability and solubility make them ideal rapid signaling regulators. Many oxysterols, like 7β-, 22-, 24-, 25-, and 27-hydroxycholesterol, redundantly regulate of sterol biosynthesis through suppression SREBP2 activity (Radhakrishnan et al., 2007). 25HC also increases cellular cholesterol accessibility by directly mobilizing cholesterol from membranes (Lange et al., 2004). While microbial effects of some oxysterols have been appreciated in chemistry, our study highlights the relationship of host antiviral response and the oxysterol 25HC—illustrating that Ch25h-induced 25HC also acts as rapid, soluble viral fusion inhibitors (Moog et al., 1998; Pezacki et al., 2009). Therefore, 25HC has multiple functions in metabolism and in immunity.

Viruses enter cells with different types of fusion machinery, classified structurally and biochemically. 25HC's inhibition on virus is not specific to particular class of fusion proteins because HIV and Ebola have class-I fusion peptides, RVFV and RSSEV use class-II peptides, whereas VSV and HSV belong to class III (Kielian and Rey, 2006; Vaney and Rey, 2011). It also inhibits viruses that undergo either pH-dependent or pH-independent fusion as exemplified by VSV and HIV, respectively. These findings suggest that 25HC affect a more basic fusion process involving the viral and cellular membrane. Indeed, 25HC causes membrane expansion, increases solvent exposure of phospholipids, and prevents the membrane condensing effect of cholesterol in bilayers (Gale et al., 2009; Olsen et al., 2011). These changes can perturb viral fusion, which is fundamentally dependent on membrane properties such as spacing of lipid head groups, receptor accessibility, membrane curvature, and fluidity (Pécheur et al., 1998; Teissier and Pécheur, 2007). Studies on viral entry have predominantly focused on viral fusion components and their interactions with specific cellular receptors. How membrane properties modulate viral fusion remains subject of further research.

We have shown the important role of Ch25h in the context of IFN induced antiviral state. Although 25HC have been associated with pathological conditions like atherosclerosis and Alzheimers, our studies suggest that it has a beneficial role in innate immunity during viral infections. The co-morbidity association of different chronic disease and 25HC would not warrant the possibility of 25HC as a long-term therapeutic for viral infections. Short-term 25HC treatment, however, suppressed HIV in vivo and 25HC inhibited highly pathogenic Ebola and RVFV, which can cause lethality within days.

Materials and Methods

Cells and Reagents:

RAW and HEK293T cells were obtained from ATCC and grown in standard DMEM with 5% FBS, 1% Penicillin/Streptomycin (GIBCO). CEM cells were cultured in RPMI media supplemented with 10% fetal calf serum (Hyclone) and 1% Pen/Strep (Invitrogen). Dr. Glen Barber (University of Miami, Fla.) provided VSV-GFP. MHV68-Luc was provided by Dr. Ren Sun in MIMG in UCLA. Luciferase activity was measured using firefly luciferase substrate kit (Promega). LDH Assay and ATP cell viability (Promega) were done on cells treated with Ch25h-conditioned media and 25HC according to manufacturer's instructions.

To make bone marrow derived macrophages (BMMs), bone marrow was harvested from 6-8 week C57B/L6 mice (Jackson Labs) and differentiated with 10 ng/mL of M-CSF in DMEM+10% FBS for 7 days. On day 6 the media was replaced and on day 7 the cells were stimulated with IFNα or IFNγ (PBL Interferon Source). The cells were treated for 2.5 hours and harvested in Trizol (Invitrogen). The RNA was isolated by isopropanol precipitation for microarray analyses. For J2 immortalized macrophages, bone marrow was infected with J2 retrovirus. A retrovirus expressing v-raf and c-myc expressing cell line was established (called GG2EE) and grown in RPMI (10 mM Hepes ph7.8, 10% FBS, 1% Pen/strep). Virus containing supernatant was harvested and filtered through 0.45 μM filter (Palleroni et al., 1991). For BCR-ABL transformed B-cells were derived by infecting bone marrow with BCR-ABL retrovirus as described previously (Scherle et al., 1990). Stable knockdown in RAW264.7 were generated using pSiren shRNA knockdown system (Clonetec) according to the published protocol. Knockdown primers sequences are available by request. Tail-derived fibroblasts were derived by skinning the tails of mice and incubating them directly in culture dishes in DMEM 10% FBS. Cells were scraped and re-plated after 7 days.

Expression plasmids were obtained from Genecopoeia, Inc. Doxycycline inducible expression system was purchased from Clonetec. SREBP2 expression plasmids were gifts from Dr. Elizabeth Tarling and Dr. Peter Edwards (UCLA). SREBP1 expression plasmids were gifts from Dr. Steven Bensinger (UCLA).

VSV, HSV, and MHV68 Viral Plaque Assay

HEK293T and RAW264.7 were infected with VSV-GFP at 0.01 MOI for 1 h and the media was changed with fresh media. For J2 BMMs and BCR-ABL B-cells, 1 MOI VSV-GFP was used. Approximately 150 uL of supernatants were collected at various timepoints between 8-16 hpi for plaque assay. For HSV and MHV68, 0.25 MOI was used for infection and supernatants were collected at 24 hpi.

Plaque Assays were done on Vero cells in 12-well plates at $2\times10^5$ and $2\times10^4$ cells per well for VSV and MHV68 plaque assay, respectively. Supernatants from infected cells were serially diluted and infected on Veros for 1 hr. The cells were then covered with growth medium containing 0.6% low-melting point agarose. Plaques stained with crystal violet 0.5% (m/v) in 20% ethanol (v/v) and were counted after 16 hrs or 6 days for VSV and MHV68, respectively.

VSV Screening and Flow-Cytometry:

HEK293T cells were plated 12 wells on collagen coated plates 0.5 mg/mL rat-tail collagen I (BD Biosciences) in PBS. Individual ISGs expression plasmid was transfected with DsRed construct (Clontech) at 3:1 ratio Fugene 6 (Roche) transfection reagents. After 36 hours, the cells were infected as described above. At 9 hpi, cells were collected in 2% paraformaldehyde solution in PBS. FACS was done with standard compensation (FACSCaliber, BDBiosciences) and the data was analyzed using CeliQuest (BDBiosciences).

Ebola, RSSEV, and RVFV Infections

HeLa cells were pre-treated with 25HC (1 μM) or EtOH containing medium for 5 hrs prior infection with Ebola-Zaire-GFP (EBOV) or Rift Valley fever virus (RVFV) wild type strain ZH501 (MOI 0.1), respectively. Cell culture supernatant aliquots were harvested at the indicated time points and pooled from biological triplicates, prior virus titration by plaque assay. For infection with RVFV vaccine strain MP-12 or Russian Spring-Summer encephalitis virus Sofjin strain (RSSEV), HeLa cells were pre-treated with 25HC (1 μM) or EtOH containing medium for 18 hrs prior infection. Plaque Assays were performed on Vero cells (for EBOV, and RVFV) in 12-well plates or BHK-SA cells (for RSSEV) in 6 well plates. Cells were infected for 1 hr at 37° C. with serial 10-fold dilutions of supernatant aliquots from infected cells. The cells were then overlain with growth medium containing 0.6% methyl cellulose (for EBOV and RVFV) or 0.5% tragacanth gum (for RSSEV). After 3 days (RVFV), 4 days (RSSEV) and 10 days (EBOV), cells were fixed with 10% buffered formalin, stained with crystal violet and plaques counted. All work involving EBOV, RSSEV and wild-type RVFV, were performed at the Robert E. Shope BSL-4 laboratory at UTMB.

HIV Infections in hPBMCs

Human peripheral blood mononuclear cells (PBMC) were obtained from the UCLA Virology Core. These cells were cultured in RPMI Medium 1640 (Invitrogen) containing 10% FBS, 100 units/ml of Penicillin+100 μg/ml of Streptomycin (Pen/Strep, Invitrogen), and 20 units/ml of interleukin-2 (Roche). PBMC were costimulated for 3 days with plate-bound anti-CD3 and soluble anti-CD28 antibodies as previously described (Korin and Zack, 1999). Costimulated PBMC were pre-incubated for 24 h at a density of $3\times10^6$ cells/ml in conditioned media before infection with HIV. Infections were set-up in 200 µl volumes of conditioned media containing $10^6$ cells, 30 ng of HIV strain NL4-3 (as determined by p24 antigen ELISA [Beckman Coulter]), and 10 µg/ml of polybrene. The mixture was incubated for 2 h at 37° C. on a rocking platform. Following infection, cells were washed twice with media and then split into triplicate 2 ml cultures in conditioned media, each containing $3.3\times10^5$ cells. At various post-infection timepoints, 100 µl of cell-free supernatant was removed and added to 2% Triton-x-100 in PBS for storage at 4° C. before quantitation of p24 concentration by ELISA.

VSV-G Pseudotyped VSV-G Luciferase Pseudovirus Production

VSV-G pseudotyped VSV-G luciferase pseudo-virus (VSVΔG-Luc/G) was generated by methods previously described (Takada et al., 1997) and concentrated by ultracentifugation on 20% sucrose cusion. The VLPs were resuspended in NTE buffer (100 mM NaCl; 10 mM Tris-HCl, pH 7.5; 1 mM EDTA) and stored in –80 C. The concentrations used to generate linear range of luciferase signal were determined empirically.

VSV-G/BlaM Production

A previously described construct encoding NipahM1 fusion with beta-lactamase (BlaM) was used to package inside VSV-G (Wolf et al., 2009). HEK293 Ts were transfected with constructs encoding BlaM and VSV-G or BlaM alone (bald) at 3:1 ratio in 10 cm dishes by PEI transfection reagent. The viral supernatants were collected, clarified, and concentrated by ultracentrifugation at >75,000 g on 20% sucrose cushion, HIV IIIB Pseudotvped Virus Production Envelopes and backbone were obtained through the NIH AIDS and Research and Reference Reagent Program. Pseudovirons were generated by cotransfection of 293T cells with envelope deleted LucRE-vector and envelope expressing vector at a 3:1 µg ratio with Bioline Bio T transfection reagent. 72 hours post transfection viral supernatant was collected, clarified by low speed centrifugation and stored at –80 c. The number of infectious virus particles was determined by serial dilution assay on Ghost HI-X4 cells, cells that express GFP controlled by a HIV LTR promoter. Briefly, $4\times10^4$ Ghost HI-X4 cells were seeded into a 48 well dish. 24 hour later, cells are infected with 2 fold serially diluted psuedovirons. 48 hours later, cells were collected and percent positive cells were determined using flow cytometry.

CEM Infection with Pseudotyped IIIB Virus

CEMs cells were treated with 25HC, 22HC or EtOH for a minimum of six hours. Prior to infection previously untreated cells were incubated with AMD3100, AZT, Elvitegravir or Nelfinavir at a concentration of 10 um or 20 um for a minimum of 15 minutes. IIIB pseudovirus was used to infect treated and untreated CEM cells at 0.1 MOI. Infections were spin inoculated for 60 minutes at 2,000 RPM, at 37 C. After spin inoculation, cells were transferred into a 37 C incubator. 48 hours post infection cells were lysed with 1% triton-X 100 and assayed for luciferase activity. P24 Assay was done in with PerkinElmer's HIV-1 P24 Elisa kit (NEK050B). Accompanied protocol was followed.

Generation of VPR-BlaM Fusion Gene

VPR-BlaM was generated by overlapping per and cloned into PCDNA3.1. VPR was amplified from SG3Δ. Catalytically optimized beta lactamase described previously in (cite) was amplified with primers (3,4). The two per products were used in the overlapping per using primers (1,4) to generate VPR-BlaM. VPR-BlaM per product was cloned into pcdna3.1 expression vector previously cut with BamHI and XhoI using the Infusion system (CloneTech).

NL4-3 VPR-BlaM Virus Production

NL4-3 VPR-BlaM was produced in according to the methods outlined previously (Cavrois et al., 2002). Briefly, 2 ug of VPR BlaM, 1 ug of padvantage (Promega) and 8 ug of NL4-3 were cotransfected into 293 Ts in 10 cm plate with PEI reagent. 48 hours post transfection viral supernatant was collected, clarified by low speed centrifugation, and concentrated on 20% sucrose cushion. VLPs were resuspended in small volume of NTE and stored at –80° C.

NL4-3 VPR-BlaM Infection of CEM Cells

CEMs cells were treated with 25HC or EtOH for a minimum of six hours. Prior to infection previously untreated cells were incubated with AMD3100 at a concentration of 20 um for a minimum of 15 minutes. Concentrated NL4-3 BlaM or Bald virus was added to treated CEM cells. Infections were spin inoculated for 60 minutes at 2,000 RPM, at 37 degrees Celsius. After spin inoculation, cells were transferred into a 37 degree incubator for 2 hours. Free floating virus was inactivated and CEM cells were washed twice. CCF2-AM (Invitrogen) was added according to manufacture's protocol. Kinetic readings were taken for 1-3 hours. After the kinetic reading the cells were washed with FACS Buffer, fixed with 2% paraformaldehyde and examined by flow cytometry. Data was analyzed using FlowJo (Tree Star Inc.).

Nipah Fusion Assay

Vero cells were plated in 6-well dish at $5\times10^5$ per well overnight and transfected with 0.5 ug of expression plasmids encoding Nipah F and G in OptiMEM (Invitrogen). At 5 h post transfection, media was changed to DMEM (10% FBS) with or with out 25HC at the indicated concentrations. The cells were fixed by methanol 21 h after transfection for 10 min, stained with Giemsa stain for 2 h, and decolorized with 95% ethanol. Nuclei inside syncytia were counted under light microscopy. Syncytia were defined as four or more nuclei within a common cell membrane. Relative fusion was defined by normalizing the number of nuclei per syncytia formed under the experimental conditions to that formed by in vehicle (ethanol) treated cells, which was set at 100%.

PCR

Cells were collected in trizol and RNA was isolated by standard isopropanol precipitation. RNA was quantitated and 1 µg of RNA was reversed transcribed using IScript (BioRad) according to the manufacturer's instructions with either random hexamer as primers. Q-PCR analysis was done using the iCycler thermocycler (Bio-Rad). Q-PCR was conducted in a final volume of 20 µL containing: Native Taq polymerase (Invitrogen), 1× Taq buffer (Stratagene), 125 µM dNTP, SYBR Green I (Molecular Probes), and Fluoroscein (Bio-Rad), and 1% cDNA. Amplification conditions were: 95° C. (3 min), 40 cycles of 95° C. (20 s), 55° C. (30 s), 72° C. (20 s). Expression values were normalized to L32 control and fold induction was normalized to untreated control. qRT-PCR of Ch25h was done with primers: Ch25h fwd: 5'-TGCTACAACGGTTCGGAGC-3' (SEQ ID NO:1). Ch25h rev: 5'-AGAAGCCCACGTAAGTGATGAT-3' (SEQ ID NO:2). L32 fwd: 5'-AAGCGAAACTGGCGGAAAC-3' (SEQ ID NO:3); L32 rev: 5'-TAACCGATGTTGGG-CATCAG-3'(SEQ ID NO:4).

For detection of VSV genomic RNA, cells infected with VSV was collected in Trizol and RNA was isolated and reverse transcribed with VSV specific primer N1-5' GATAGTACCGGAGGATTGACGACTA (SEQ ID NO:5) using Superscript II (Invitrogen) according to manufacturer's protocol. Real time PCR with Taqman probe with conditions described above. VSV fwd: 5'-GATAGTACCG-GAGGATTGACGACTA-3' (SEQ ID NO:6); VSV rev: 5'-TCAAACCATCCGAGCCATTC-3 (SEQ ID NO:7); VSV Probe: 5' (FAM)-TGCACCGCCACAAGGCAGAGA-(TAMRA)-3' (SEQ ID NO:8).

CEM cells were infected with HIV IIIB expressing GFP and or Luciferase. After spinoculation, the cells were collected at indicated time and total DNA was extracted with DNAeasy Blood &Tissue Kit (Qiagen). Full length LateRT was measured by Taqman qRT-PCR as described previously (Butler et al., 2001) and normalized to mitochondria DNA. Primers used: late RT forward: 5'-TGTGTGCCCGTCTGTTGTGT-3' (SEQ ID NO:9); late RT reverse: 5'-GAGTCCTGCGTCGAGAGAGC-3' (SEQ ID NO:10); late RT probe, 5'-(FAM)-CAGTGGCGCCCGAACAGGGA-(TAMRA)-3' (SEQ ID NO:11); Mitochondrial forward primer, 5'-ACC-CACTCCCTCTTAGCCAATATT-3' (SEQ ID NO:12); mitochondrial reverse primer, 5'-GTAGGGCTAGGCC-CACCG-3' (SEQ ID NO:13).

RNA Isolation and RNAseq of Bone Marrow Derived Macrophage Stimulation $5 \times 10^5$ BMMs from wildtype (C57BL/6), IFNAR-deficient and IL-27R (TCCR/WSX-1) deficient mice were stimulated with Lipid A (100 ng/mL) or saline control for 4 hr and 12 hr, respectively. Cells were harvested in Trizol (Invitrogen) and RNA was isolated via chloroform extraction.

Prior to cDNA library construction for RNA-Seq analyses, RNA was quantified and assessed for quality (RNA Integrity Value) using an Agilent 2100 Bioanalyzer (Santa Clara, Calif.). 1 ug of RNA per condition was used for library construction using TruSeq SBS Kit v3 (Fc-401-3001) according to the manufacturers guidelines (Illumina, San Diego, Calif.). Multiplex Sequence Analysis was performed using a Illumina HiSeq2000 Single End 100 bp read parameters according to the manufacturers guidelines (www.illumina.com). Sequencing was performed by the Southern California Genotyping Consortium (SCGC) in the Epigenetics and Genetics Core at UCLA. Sequence reads from each cDNA library (100 bp, single-read) were trimmed to 80 bp long and mapped onto the mouse genome build NCBI37/mm9 using Bowtie (bowtie-0.12.1, http://bowtie-bio.source-forge.net/index.shtml) with setting '-v 2-k 11-m 10-t-best-strata'. The mappable data were then processed by the ERANGE v. 3.3 RNA-seq analysis program (Mortazavi et al., 2008). Assuming total transcriptional activity is comparable between different cell types, the obtained data (data units in RPKM, reads per kilobase exon model per million mapped reads) were first $\log_2$ transformed and linearly normalized between individual samples, then averaged among biological replicates or triplicates. At the same time, in order to find genes that were changed in expression between two populations to a statistically significant degree, ERANGE processed data were analyzed by the Bioconductor DEGseq program (Wang et al., 2010) (http://www.bioconductor.org/packages/2.6/bioc/html/DEGseq.html) (data units in RPM, reads per million mapped reads, method="MARS," p<0.001). Data is presented using RPKM values.

Construction of DKO-Hu Mice

DKO-hu mice were constructed as previously reported (Zhang et al., 2006). Briefly, human CD34+ cells were isolated from 17-20 weeks old fetal liver tissues. The cell suspension released from the liver was filtered through a 70-um cell strainer (BD Falcon) centrifuged at 150×g for 5 min to get rid of hepatocytes. The mononuclear cells were purified through Ficoll gradient (GE Healthcare Bioscience AB). Cells were labeled with CD34 MicroBead Kit from Miltenyi Biotec, then CD34+ cells were positive selected with autoMACS followed the vendor's instruction (Miltenyi Biotec, Germany). 1-5×105 CD34+ HSPC cells were injected into the liver of each DKO mouse at 1 to 3 days old, which has been previously irradiated at 400 rad. Transplanted mice were bled through tail vein at 3-4 months after transplant to check human cell reconstitution by flow cytometry. All animal experiences were reviewed and approved by the University of North Carolina—Chapel Hill Institutional Animal Care and Use Committee.

HIV Infection in DKO-Hu Mice

We used an HIV molecular clone with a highly pathogenic dual tropic envelope, R3A in NL4-3 Backbone for infection. HIV-1 viral stocks were produced in 293T cells and expanded in PHA activated PBMC, and titered on Hela-CD4-LTR-gal cells (NIH AIDS Research and Reference Reagent Program, Division of AIDS, NIAID). DKO-hu mice with stable human leukocyte reconstitution were administered 50 mg/kg of 25HC or the vehicle control (2-hydroxypropyl)-β-cyclodextrin (HBCD) intraperitonial (i.p.) injection for 12 h before infection with HIV NL4-R3A at 5 ng of p24/mouse by intravenously injection (i.v.). Mice were administered 50 mg/kg of 25HC or HBCD control every day. DKO-hu mice infected with mock supernatant were included as control groups. HIV replication (genome copy/ml in the plasma) was measured by the Roche Amplicor Monitor v.1.5 qRT-PCR assay (Roche Diagnostics Corporation, Indianapolis, Ind.), or by p24 intracellular staining. Intracellular staining and FACs analysis were done as previously described (Zhang et al., 2011).

Mouse Infections and Bioluminescence Imaging

C57BL/6 and ch25h−/− mice were purchased from Jackson. Mice were first anaesthetized by intraperitoneal (i.p.) injection with 200 mg/kg ketamine, 4 mg/kg xylazine in PBS. MHV68 (500 pfu) in 200 uL of PBS was administered by i.p. On days 3 following infection, mice were imaged using the in vivo imaging system (IVIS, Xenogen). Briefly, mice were anaesthetized by intraperitoneal injection with 200 mg/kg ketamine, 4 mg/kg xylazine in PBS, followed by intraperitoneal injection of 3 mg D-luciferin/mouse prior to imaging. Grayscale photographs and color images of imaged mice were superimposed with LivingImage (Xenogen) and Igor (Wavemetrics) programs, similar to that previously described. The mice were imaged on dorsal, ventral, right, and left side until the maximal luminescence has passed. The average and maximum photon flux value was measured for each mouse at every angle and expressed as photons/sec/$cm^2$/steradian. These values were averaged for all the mice. At 9 dpi, mice were euthanized the spleens were extracted and homogenized in DMEM. Total DNA was extracted using DNeasy Blood & Tissue Kit (Qiagen) and MFIV68 DNA was quantified by qRT-PCR.

In vivo analysis of 25HC-mediated inhibition of other enveloped viruses, including viruses disclosed herein, is conducted using conventional assays, in established animal models. The animal models differ for various viruses being tested. For example, suitable mouse, rat, chicken and non-human primate models are available. It is expected that these viruses, too, will be inhibited by 25HC, in a similar manner as shown herein for HIV.

References for Example 1

Andrew J, and Jessup, W. (1999). Oxysterols and atherosclerosis. Atherosclerosis 142, 1-28.

Bauman, D. R., Bitmansour, A.D., McDonald, J. G., Thompson, B. M., Liang, G., and Russell, D. W. (2009). 25-Hydroxycholesterol secreted by macrophages in response to Toll-like receptor activation suppresses immunoglobulin A production. Proceedings of the National Academy of Sciences 106, 16764-16769.

Brass, A. L., Huang, I.-C., Benita, Y., John, S. P., Krishnan, M. N., Feeley, E. M., Ryan, B. J., Weyer, J. L., van der Weyden, L., Fikrig, E., et al. (2009). The IFITM Proteins Mediate Cellular Resistance to Influenza A H1N1 Virus, West Nile Virus, and Dengue Virus. Cell 139, 1243-1254.

Butler, S. L., Hansen, M. S. T., and Bushman, F. D. (2001). A quantitative assay for HIV DNA integration in vivo. Nat Med 7, 631-634.

Cavrois, M., de Noronha, C., and Greene, W. C. (2002). A sensitive and specific enzyme-based assay detecting HIV-1 virion fusion in primary T lymphocytes. Nat Biotech 20, 1151-1154.

Degols, G., Eldin, P., and Mechti, N. (June). ISG20, an actor of the innate immune response. Biochimie 89, 831-835.

Gale, S. E., Westover, E. J., Dudley, N., Krishnan, K., Merlin, S., Scherrer, D. E., Han, X., Zhai, X., Brockman, H. L., Brown, R. E., et al. (2009). Side Chain Oxygenated Cholesterol Regulates Cellular Cholesterol Homeostasis through Direct Sterol-Membrane Interactions. Journal of Biological Chemistry 284, 1755-1764.

García, M. A., Gil, J., Ventoso, I., Guerra, S., Domingo, E., Rivas, C., and Esteban, M. (2006). Impact of Protein Kinase PKR in Cell Biology: from Antiviral to Antiproliferative Action. Microbiology and Molecular Biology Reviews 70, 1032-1060.

Holmes, R., VandeBerg, J., and Cox, L. (2011). Genomics and proteomics of vertebrate cholesterol ester lipase (LIPA) and cholesterol 25-hydroxylase (CH25H). 3 Biotech 1, 99-109.

Janowski, B. A., Grogan, M. J., Jones, S. A., Wisely, G. B., Kliewer, S. A., Corey, E. J., and Mangelsdorf, D. J. (1999). Structural requirements of ligands for the oxysterol liver X receptors LXRα and LXRβ. Proceedings of the National Academy of Sciences 96, 266-271.

Kandutsch, A., Chen, H., and Heiniger, H. (1978). Biological activity of some oxygenated sterols. Science 201, 498-501.

Kielian, M., and Rey, F. A. (2006). Virus membrane-fusion proteins: more than one way to make a hairpin. Nat Rev Micro 4, 67-76.

Korin, Y. D., and Zack, J. A. (1999). Nonproductive Human Immunodeficiency Virus Type 1 Infection in Nucleoside-Treated GO Lymphocytes. Journal of Virology 73, 6526-6532.

Lange, Y., Ye, J., and Steck, T. L. (2004). How cholesterol homeostasis is regulated by plasma membrane cholesterol in excess of phospholipids. Proceedings of the National Academy of Sciences of the United States of America 101, 11664-11667.

Liu, S.-Y., Sanchez, D. J., Aliyari, R., Lu, S., and Cheng, G. (2012). Systematic identification of type I and type II interferon-induced antiviral factors. Proceedings of the National Academy of Sciences 109, 4239-4244.

Moog, C., Aubertin, A., Kim, A., and Luu, B. (1998). Oxysterols, but not cholesterol, inhibit human immunodeficiency virus replication in vitro. Antiviral Chemistry & Chemotherapy 9, 491-496.

Mortazavi, A., Williams, B. A., McCue, K., Schaeffer, L., and Wold, B. (2008). Mapping and quantifying mammalian transcriptomes by RNA-Seq. Nat Meth 5, 621-628.

Negrete, O. A., Wolf, M. C., Aguilar, H. C., Enterlein, S., Wang, W., Mithlberger, E., Su, S. V., Bertolotti-Ciarlet, A., Flick, R., and Lee, B. (2006). Two Key Residues in EphrinB3 Are Critical for Its Use as an Alternative Receptor for Nipah Virus. PLoS Pathog 2, e7.

Olsen, B. N., Schlesinger, P. H., Ory, D. S., and Baker, N. A. (2011). 25-Hydroxycholesterol Increases the Availability of Cholesterol in Phospholipid Membranes. Biophysical Journal 100, 948-956.

Palleroni, A. V., Varesio, L., Wright, R. B., and Brunda, M. J. (1991). Tumoricidal alveolar macrophage and tumor infiltrating macrophage cell lines. Int. J. Cancer 49, 296-302.

Park, K., and Scott, A. L. (2010). Cholesterol 25-hydroxylase production by dendritic cells and macrophages is regulated by type I interferons. Journal of Leukocyte Biology 88, 1081-1087.

Pécheur, E.-I., Sainte-Marie, J., Bienvenüe, A., and Hoekstra, D. (1998). Lipid Headgroup Spacing and Peptide Penetration, but Not Peptide Oligomerization, Modulate Peptide-Induced Fusion †. Biochemistry 38, 364-373.

Perez-Caballero, D., Zang, T., Ebrahimi, A., McNatt, M. W., Gregory, D. A., Johnson, M. C., and Bieniasz, P. D. (2009). Tetherin Inhibits HIV-1 Release by Directly Tethering Virions to Cells. Cell 139, 499-511.

Pezacki, J., Sagan, S., Tonary, A., Rouleau, Y., Belanger, S., Supekova, L., and Su, A. (2009). Transcriptional profiling of the effects of 25-hydroxycholesterol on human hepatocyte metabolism and the antiviral state it conveys against the hepatitis C virus. BMC Chemical Biology 9, 2.

Radhakrishnan, A., Ikeda, Y., Kwon, H. J., Brown, M. S., and Goldstein, J. L. (2007). Sterol-regulated transport of SREBPs from endoplasmic reticulum to Golgi: Oxysterols block transport by binding to Insig. Proceedings of the National Academy of Sciences 104, 6511-6518.

Scherle, P. A., Dorshkind, K., and Witte, O. N. (1990). Clonal lymphoid progenitor cell lines expressing the BCR/ABL oncogene retain full differentiative function. Proceedings of the National Academy of Sciences 87, 1908-1912.

Takada, A., Robison, C., Goto, H., Sanchez, A., Murti, K. G., Whitt, M. A., and Kawaoka, Y. (1997). A system for functional analysis of Ebola virus glycoprotein. Proceedings of the National Academy of Sciences 94, 14764-14769.

Teissier, É., and Pécheur, E.-I. (2007). Lipids as modulators of membrane fusion mediated by viral fusion proteins. European Biophysics Journal 36, 887-899.

Vaney, M.-C., and Rey, F. A. (2011). Class II enveloped viruses. Cellular Microbiology 13, 1451-1459.

Wang, F., Xia, W., Liu, F., Li, J., Wang, G., and Gu, J. (2012). Interferon regulator factor 1/retinoic inducible gene I (IRF1/RIG-I) axis mediates 25-hydroxycholesterol-induced interleukin-8 production in atherosclerosis. Cardiovascular Research 93, 190-199.

Wang, L., Feng, Z., Wang, X., Wang, X., and Zhang, X. (2010). DEGseq: an R package for identifying differentially expressed genes from RNA-seq data. Bioinformatics 26, 136-138.

Weidner, J. M., Jiang, D., Pan, X.-B., Chang, J., Block, T. M., and Guo, J.-T. (2010). Interferon-Induced Cell Membrane Proteins, IFITM3 and Tetherin, Inhibit Vesicular Stomatitis Virus Infection via Distinct Mechanisms. Journal of Virology 84, 12646-12657.

Wolf, M., Wang, Y., Freiberg, A., Aguilar, H., Holbrook, M., and Lee, B. (2009). A catalytically and genetically optimized beta-lactamase-matrix based assay for sensitive, specific, and higher throughput analysis of native henipavirus entry characteristics. Virology Journal 6, 119.

Zhang, L., Jiang, Q., Li, G., Jeffrey, J., Kovalev, G. I., and Su, L. (2011). Efficient infection and impairment of pDC in the bone marrow and peripheral lymphoid organs during early HIV-1 infection in humanized rag2−/−γC−/− mice in vivo. Blood.

Zhang, L., Kovalev, G. I., and Su, L. (2006). HIV-1 infection and pathogenesis in a novel humanized mouse model. Blood.

Zlokarnik, G., Negulescu, P. A., Knapp, T. E., Mere, L., Burres, N., Feng, L., Whitney, M., Roemer, K., and Tsien, R. Y. (1998). Quantitation of Transcription and Clonal Selection of Single Living Cells with β-Lactamase as Reporter. Science 279, 84-88.

Zou, T., Garifulin, O., Berland, R., and Boyartchuk, V. L. (2011). *Listeria monocytogenes* Infection Induces Prosurvival Metabolic Signaling in Macrophages. Infection and Immunity 79, 1526-1535.

Example 2—Supplemental Information

Figure 15:
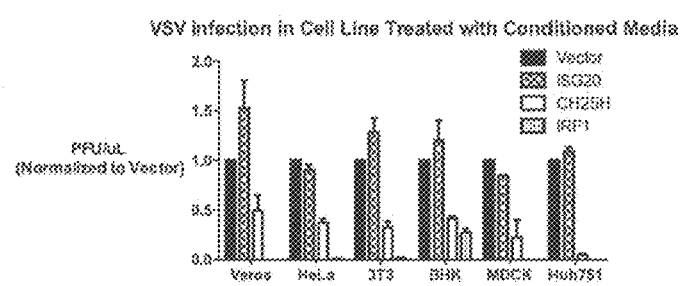
FIG. 15. (A) Indicated cell lines were treated for 8-12 h with conditioned media from HEK293T transfected with indicated expression vectors. They were infected with VSV at 0.01 MOI for 9-14 h, depending on the cell line. VSV-GFP was quantified by FACs (% GFP+X Geometric MFI) and normalized to VSV-GFP in cell treated with vector-conditioned media. Mean±SEM. (B) HEK293T was transfected with indicated expression vector and IFNβ-luciferase reporter. Luciferase activity was measured after 16 h. RLU-relative light units. Mean±SEM (C) IFNβELISA of conditioned media from HEK293T transfected with indicated expression vectors after 24 h.
Figure 15:
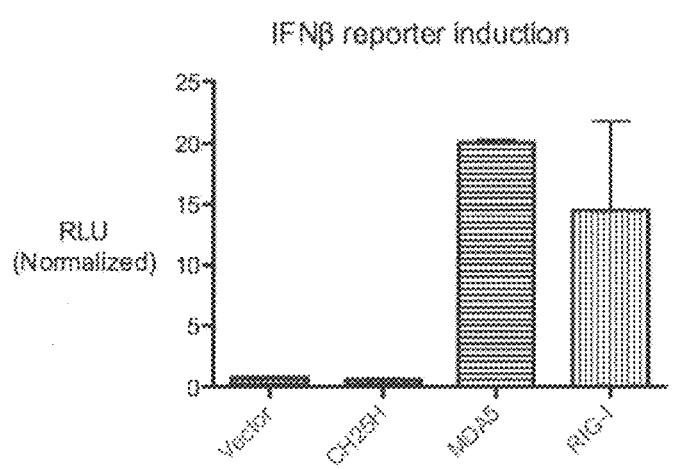
Figure 15:
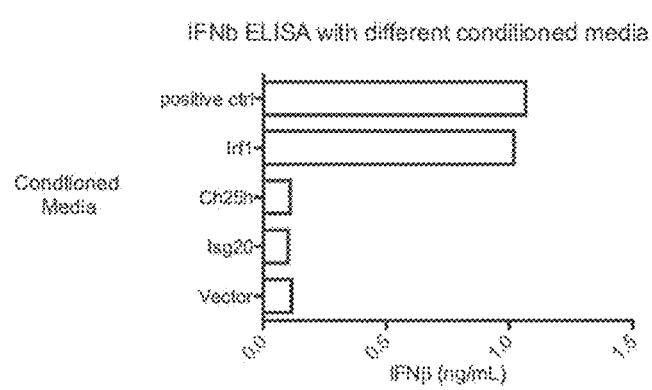
Figure 16:
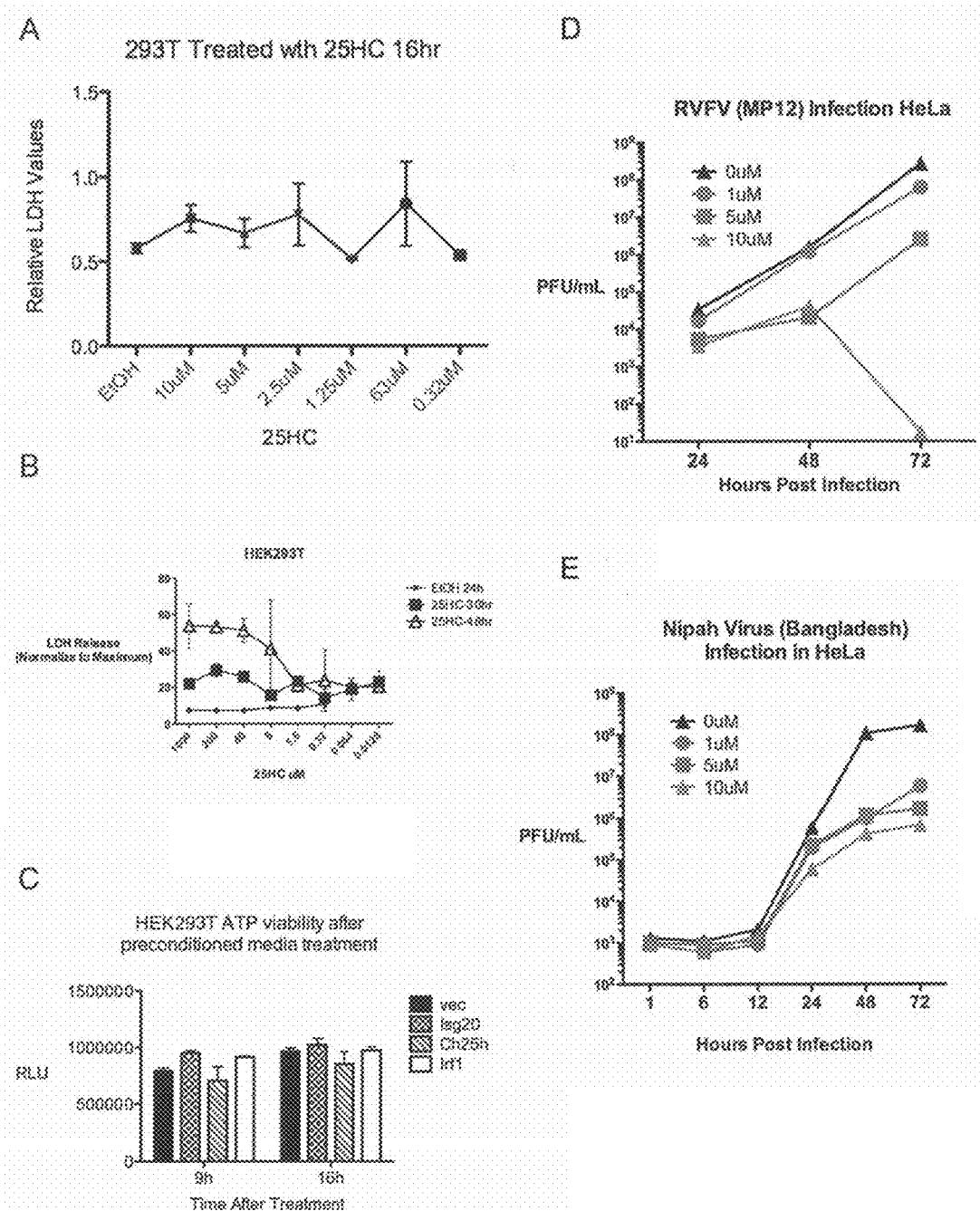
FIG. 16. (A) HEK293T were treated with increasing amount of 25HC and LDH values was measured after 16 h. Mean±SD. (B) HEK293T were treated with increasing amount of 25HC and LDH was measured after 30 and 48 h. Mean+SD. (C) HEK293T was treated with indicated conditioned media for 16 h. Cell viability was measured by quantitation of ATP present in the cell by luminescent substrate. Mean±SD. (D) HeLa cells were pretreated with media containing indicated concentrations of 25HC or EtOH for 18 h and infected with RVFV (MP12 vaccine strain) at 0.1 MOI. Viral titer at indicated time points was measured by plaque assay. Values represent means of samples from triplicates. (E) HeLa cells were pretreated with media containing indicated concentrations of 25HC or EtOH for 18 h and infected with Nipah virus (Bangladesh strain) at 0.1 MOI. Viral titer at indicated time points was measured by plaque assay. Values represent means of samples from triplicates.
Figure 17:
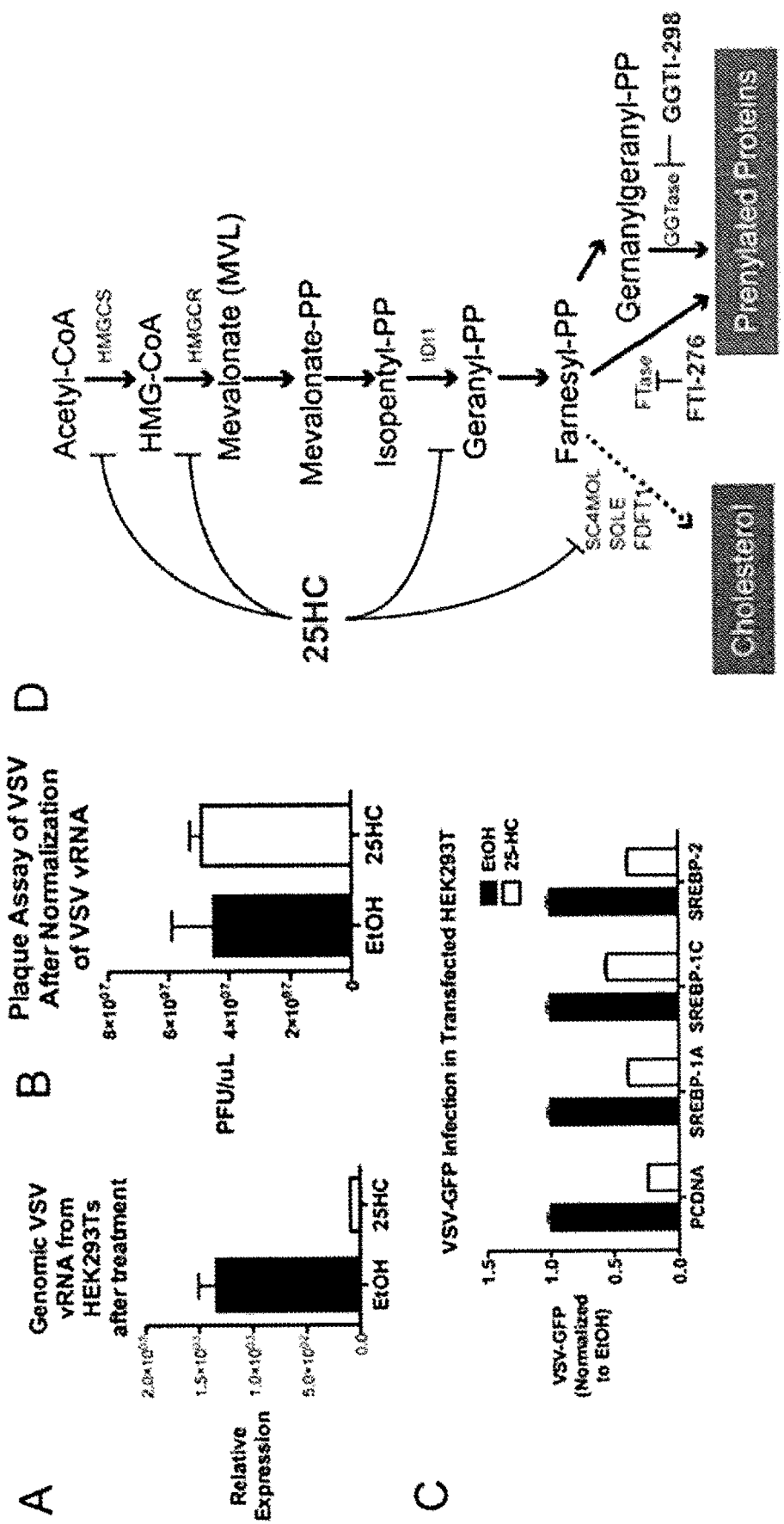
FIG. 17. (A) HEK293T were treated with 25HC (2.5 μM) and vehicle (EtOH) for 8 h and infected with VSV-GFP at 0.01 MOI. The cells were treated against with 25HC after infection. Supernatants were collected 24 hpi and virus was concentrated by centrifugation. For a part of the concentrated virus, VSV genomic RNA (gRNA) was quantified by qRT-PCR. Mean±SEM. (B) Concentrated virus from part A was normalized based on VSV gRNA and standard plaque assay was performed. Mean±SEM. (C) HEK293T were transfected with mature form of Srebp1a, Srebp1c, and Srebp2 for 24 and treated with 25HC for 12 h. The cells were infected with VSV-GFP (0.01 MOI) and quantified by FACs. Mean±SEM. (D) Schematic of sterol synthesis and isopentyl-PP pathway. 25HC inhibit several enzymes within the pathway (purple): HMG-CoA Reductase (HMGCR1), 3-hydroxy-3-methylglutaryl-CoA synthase (HMGCS1), sterol-C4-methyl oxidase (SC4MOL), squalene epoxidase (SQLE), acetyl-CoA acetyltransferase (ACAT), farnesyl-diphosphate farnesyltransferase (FDFT), isopentenyl-diphosphate isomerase (IDI1). Two inhibitors of prenylation, FTI-276 and GGTI-298, are also shown. (E) HEK293 Ts were treated with 25HC, mevalonic acid (300 uM), or both for 12 h and infected with VSV-GFP (0.01 MOI). VSV-GFP was quantified by FACs at 9 hpi. Mean±SEM. (F) HEK293T was treated as indicated for 12 h and infected with VSV-GFP (0.01 MOI). VSV-GFP was quantified by FACs at 9 hpi. (G) Cytotoxicity of treatments in part. C were measured by ATP content and normalized to respective control (DMSO for GGTI-298 and FTI-276, EtOH for 25HC). Mean±SEM, *P<0.05. (H) HEK293T were treated with FTI-276 at indicated concentration and respective concentrations for 12 h and infected with VSV-G-13laM. 13-lactamase activity was measured by blue:green ratio of the cleaved CCF2-AM. Mean±SEM. (I) HEK293T were treated with GGTI-298 at indicated concentration and respective concentrations for 12 h and infected with VSV-G-13laM. 13-lactamase activity was measured by blue:green ratio of the cleaved CCF2-AM. Mean±SEM.

The data shown in Example 1 are extended as shown in FIGS. 15-18 and as described in the Descriptions of those figures. FIG. 15 is related to FIG. 3; FIG. 16 is related to FIG. 4; FIG. 17 is related to FIG. 5; and FIG. 18 is related to FIG. 6.

Experimental procedures were the same as in Example 1, except for the following:

Cells and Reagents

RAW264.7 (ATCC), Vero, HeLa, 3T3, BHK, MDCK, Huh751, and HEK293T cells were grown in standard DMEM with 10% FBS, 1% Penicillin/Streptomycin (GIBCO). CEM cells were cultured in RPMI media supplemented with 10% fetal calf serum (Hyclone) and 1% Pen/Strep (Invitrogen). Dr. Glen Barber (University of Miami, Fla.) provided VSV-GFP. MHV68-Luc was provided by Dr. Ren Sun in MIMG in UCLA. Luciferase activity was measured using firefly luciferase substrate kit (Promega). LDH Assay and ATP cell viability (Promega) were done on cells treated with Ch25h-conditioned media and 25HC according to manufacturer's instructions. FTI276 and GGTI-298 (Sigma) were used at 5-20 µM, consistent with published doses of prenylation inhibition (Wilson et al., 1998; Liu et al., 2012; Miller et al., 2012).

Expression plasmids were obtained from Genecopoeia, Inc. Doxycycline inducible expression system was purchased from Clonetec. SREBP2 expression plasmids were gifts from Dr. Elizabeth Tarling and Dr. Peter Edwards (UCLA). SREBP1 expression plasmids were gifts from Dr. Steven Bensinger (UCLA).

Primary Cells and Cell Lines

Bone marrow was harvested from 6-8 week C57B/L6 mice (Jackson Labs) and differentiated in DMEM+10% FBS for 7 days with 10 ng/mL of M-CSF or GM-CSF for macrophage (BMM) or dendritic cells (BMDC), respectively. On day 6 the media was replaced and on day 7 the cells were stimulated with TEM or IFNs (PBL Interferon Source). The cells were treated for 2.5 hours and harvested in Trizol (Invitrogen). The RNA was isolated by isopropanol precipitation for microarray analyses. For J2 immortalized macrophages, bone marrow was infected with J2 retrovirus. A retrovirus expressing v-raf and c-myc expressing cell line was established (called GG2EE) and grown in RPMI (10 mM Hepes ph7.8, 10% FBS, 1% Pen/strep). Virus containing supernatant was harvested and filtered through 0.45 µM filter (Palleroni et al., 1991). For BCR-ABL transformed B-cells were derived by infecting bone marrow with BCR-ABL retrovirus as described previously (Scherle et al., 1990). Stable knockdown in RAW264.7 were generated using pSiren shRNA knockdown system (Clonetec) according to the published protocol. Knockdown primer sequences are available by request. Tail-derived fibroblasts were derived by skinning the tails of mice and incubating them directly in culture dishes in DMEM 10% FBS. Cells were scraped and re-plated after 7 days.

Human peripheral blood mononuclear cells (PBMC) were obtained from the UCLA Virology Core. These cells were cultured in RPMI Medium 1640 (Invitrogen) containing 10% FBS, 100 units/ml of Penicillin+100 µg/ml of Streptomycin (Pen/Strep, Invitrogen), and 20 units/ml of interleukin-2 (Roche). PBMC were costimulated for 3 days with plate-bound anti-CD3 and soluble anti-CD28 antibodies as previously described (Korin and Zack, 1999).

Ebola, Nipah, RVFV, RSSEV Plaque Assay

Plaque Assays were performed on Vero cells (for EBOV, Nipah, and RVFV) in 12-well plates or BHK-SA cells (for RSSEV) in 6 well plates. Cells were infected for 1 hr at 37° C. with serial 10-fold dilutions of supernatant aliquots from infected cells. The cells were then overlaid with growth medium containing 0.6% methylcellulose (for EBOV, Nipah, and RVFV) or 0.5% tragacanth gum (for RSSEV). After 3 days (RVFV, Nipah), 4 days (RSSEV) and 10 days (EBOV), cells were fixed with 10% buffered formalin, stained with crystal violet and plaques counted. All work involving EBOV, Nipah, RSSEV and wild-type RVFV, were performed at the Robert E. Shope BSL-4 laboratory at UTMB.

HIV IIIB Pseudotyped Virus Production

HIV-IIIB pseudovirus were made of HIV-IIIB envelope on a NL4-3 backbone coexpressing luciferase (pNL4-3.Luc.-R-E). Plasmids were obtained through the NIH AIDS and Research and Reference Reagent Program. Pseudovirus were generated by cotransfection of 293T cells with envelope deleted LucRE-vector and envelope expressing vector at a 3:1 µg ratio with Bioline Bio T transfection reagent. 72 hours post transfection viral supernatant was collected, clarified by low speed centrifugation and stored at −80 c. The number of infectious virus particles was determined by serial dilution assay on Ghost HI-X4 cells, cells that express GFP controlled by a HIV LTR promoter. Briefly, 4×10$^4$ Ghost HI-X4 cells were seeded into a 48 well dish. 24 hour later, cells are infected with 2 fold serially diluted pseudovirions. 48 hours later, cells were collected and the percentage of positive cells were determined using FACs.

Liposome Competition Experiment with 25HC and LJ001

Recombinant unilamillar liposomes with a composition of 7:3 phosphatidylcholine:cholesterol (Encapsula Inc.) was added to HEK293T with or without 25HC (1 uM) for 8 h. Cells were washed with PBS and infected with VSV-GFP for 1 h and quantified by FACs at 9 hpi. LJ001 treatment was described previously (Wolf et al., 2010). Briefly, LJ001 was mixed with liposomes and VSV-GFP for 10 min prior to infection because it intercalates into viral membrane to inhibit fusion.

References for Example 2

Butler, S. L., Hansen, M. S. T., and Bushman, F. D. (2001). A quantitative assay for HIV DNA integration in vivo. Nat Med 7, 631-634.

Cavrois, M., de Noronha, C., and Greene, W. C. (2002). A sensitive and specific enzyme-based assay detecting HIV-1 virion fusion in primary T lymphocytes. Nat Biotech 20, 1151-1154.

Korin, Y. D., and Zack, J. A. (1999). Nonproductive Human Immunodeficiency Virus Type 1 Infection in Nucleoside-Treated G0 Lymphocytes. Journal of Virology 73, 6526-6532.

Liu, X. V., Ho, S. S. W., Tan, J. J., Kamran, N., and Gasser, S. (2012). Ras Activation Induces Expression of Raet1 Family NK Receptor Ligands. The Journal of Immunology 189, 1826-1834.

Miller, B. T., Ueta, C. B., Lau, V., Jacomino, K. G., Wasserman, L. M., and Kim, B. W. (2012). Statins and Downstream Inhibitors of the Isoprenylation Pathway Increase Type 2 Iodothyronine Deiodinase Activity. Endocrinology 153, 4039-4048.

Mortazavi, A., Williams, B. A., McCue, K., Schaeffer, L., and Wold, B. (2008). Mapping and quantifying mammalian transcriptomes by RNA-Seq. Nat Meth 5, 621-628.

Palleroni, A. V., Varesio, L., Wright, R. B., and Brunda, M. J. (1991). Tumoricidal alveolar macrophage and tumor infiltrating macrophage cell lines. Int. J. Cancer 49, 296-302.

Scherle, P. A., Dorshkind, K., and Witte, O. N. (1990). Clonal lymphoid progenitor cell lines expressing the BCR/ABL oncogene retain full differentiative function. Proceedings of the National Academy of Sciences 87, 1908-1912.

Takada, A., Robison, C., Goto, H., Sanchez, A., Murti, K. G., Whitt, M. A., and Kawaoka, Y.

(1997). A system for functional analysis of Ebola virus glycoprotein. Proceedings of the National Academy of Sciences 94, 14764-14769.

Wang, L., Feng, Z., Wang, X., Wang, X., and Zhang, X. (2010). DEGseq: an R package for identifying differentially expressed genes from RNA-seq data. Bioinformatics 26, 136-138.

Wilson, A. L., Erdman, R. A., Castellano, F., and Maltese, W. A. (1998). Prenylation of Rab8 GTPase by type I and type II geranylgeranyl transferases. Biochem. J. 333, 497-504.

Wolf, M., Wang, Y., Freiberg, A., Aguilar, H., Holbrook, M., and Lee, B. (2009). A catalytically and genetically optimized beta-lactamase-matrix based assay for sensitive, specific, and higher throughput analysis of native henipavirus entry characteristics. Virology Journal 6, 119.

Wolf, M. C., Freiberg, A. N., Zhang, T., Akyol-Ataman, Z., Grock, A., Hong, P. W., Li, J., Watson, N. F., Fang, A. Q., Aguilar, H. C., et al. (2010). A broad-spectrum antiviral targeting entry of enveloped viruses. Proceedings of the National Academy of Sciences 107, 3157-3162.

Zhang, L., Jiang, Q., Li, G., Jeffrey, J., Kovalev, G. I., and Su, L. (2011). Efficient infection and impairment of pDC in the bone marrow and peripheral lymphoid organs during early HIV-1 infection in humanized rag2-/-γC-/- mice in vivo. Blood.

From the foregoing description, one skilled in the art can easily ascertain the essential characteristics of this invention, and without departing from the spirit and scope thereof, can make changes and modifications of the invention to adapt it to various usage and conditions and to utilize the present invention to its fullest extent. The preceding preferred specific embodiments are to be construed as merely illustrative, and not limiting of the scope of the invention in any way whatsoever. The entire disclosure of all applications, patents, and publications cited above, including U.S. Provisional application 61/643,110, filed May 4, 2012, are hereby incorporated by reference in their entirety, particularly with regard to the subject matter for which they are cited.

---

We claim:

1. A method for inhibiting, comprising administering, or causing to be administered, to a cell, 25-hydroxycholesterol (25HC) in an amount sufficient to inhibit the growth and/or proliferation and/or infectivity of a virus in vivo in the cell, wherein the cell is in a subject, and the 25HC is administered or caused to be administered to the subject, and the virus is herpes simplex virus (HSV).

2. The method of claim 1, wherein the method is a method for preventing a viral infection of a mammal, and the method comprises administering, or causing to be administered, to the mammal, 25HC in an amount sufficient to inhibit infectivity of the virus in the mammal.

3. The method of claim 1, wherein the method is a method for inhibiting entry of the virus into a cell in a mammalian subject, and the method comprises administering, or causing to be administered, to the mammal, 25HC in an amount sufficient to inhibit entry of the virus into the cell.

4. The method of claim 3, wherein said 25HC is administered by a route selected from the group consisting of topical administration, oral administration, nasal administration, rectal administration, vaginal administration, intraperitoneal injection, intravascular injection, subcutaneous injection, transcutaneous administration, inhalation administration, and intramuscular injection.

5. The method of claim 3, wherein the 25HC is administered topically, vaginally, rectally, or to the buccal cavity.

6. The method of claim 3, wherein the 25HC is administered to a mucosal surface.

7. The method of claim 3, wherein the 25HC is formulated as a cream, gel, or foam for rectal delivery or vaginal delivery or topical administration.

8. The method of claim 3, wherein the 25HC is formulated as a mouthwash for delivery to the buccal cavity.

9. The method of claim 3, wherein the 25HC is formulated for oral or intravenous delivery.

10. The method of claim 9, wherein the 25HC is solubilized in (2-hydroxy)-beta-cyclodextrin.

11. The method of claim 3, wherein the mammal or mammalian cell is a non-human mammal.

12. The method of claim 3, wherein the mammal or mammalian cell is human.

13. The method of claim 12, wherein the human is identified as being at risk for an infection by the virus.

14. The method of claim 12, wherein the human is identified as having an infection by the virus.

* * * * *